(12) United States Patent
Jacobs

(10) Patent No.: US 9,317,652 B1
(45) Date of Patent: *Apr. 19, 2016

(54) COMPUTER IMPLEMENTED SYSTEM FOR QUANTIFYING STABILITY AND FLEXIBILITY RELATIONSHIPS IN MACROMOLECULES

(75) Inventor: Donald J. Jacobs, Charlotte, NC (US)

(73) Assignee: THE UNIVERSITY OF NORTH CAROLINA AT CHARLOTTE, Charlotte, NC (US)

( * ) Notice: Subject to any disclaimer, the term of this patent is extended or adjusted under 35 U.S.C. 154(b) by 728 days.

This patent is subject to a terminal disclaimer.

(21) Appl. No.: 13/540,917

(22) Filed: Jul. 3, 2012

Related U.S. Application Data

(63) Continuation of application No. 12/344,192, filed on Dec. 24, 2008, now Pat. No. 8,244,504.

(60) Provisional application No. 61/016,551, filed on Dec. 24, 2007.

(51) Int. Cl.
*G01N 33/48* (2006.01)
*G01N 33/50* (2006.01)
*G06F 19/12* (2011.01)
*G06F 19/26* (2011.01)

(52) U.S. Cl.
CPC ............... *G06F 19/12* (2013.01); *G06F 19/26* (2013.01)

(58) Field of Classification Search
None
See application file for complete search history.

(56) References Cited

U.S. PATENT DOCUMENTS

| 6,014,449 | A  | 1/2000  | Jacobs et al.   |
| 6,832,162 | B2 | 12/2004 | Floudas et al.  |
| 8,244,504 | B1 | 8/2012  | Jacobs          |
| 8,374,828 | B1 | 2/2013  | Jacobs et al.   |
| 2003/0130827 | A1 | 7/2003 | Bentzien et al. |

FOREIGN PATENT DOCUMENTS

| EP | 1 025 521 A1 | 8/2000 |
| WO | 98/54665 A1  | 12/1998 |

OTHER PUBLICATIONS

Foster EAD. A Distance Constraint Model for the prediction of protein tertiary structure. Can. J. Fish. Aquat. Sci., vol. 43, 1986, pp. 1035-1044.*
U.S. Appl. No. 12/344,512, filed Dec. 27, 2008 for "Computer Implemented System for Protein and Drug Target Design Utilizing Quantified Stability and Flexibility Relationships to Control Function".
Pierce et al., Protein design is NP-hard; Protein Eng (2002), 15:779-782.
Viogt et al., Trading accuracy for speed: A quantitative comparison of search algorithms in protein sequence design; J Mol Biol (2000), 299:789-803.

(Continued)

*Primary Examiner* — Russell S Negin
(74) *Attorney, Agent, or Firm* — Additon, Higgins & Pendleton, P.A.

(57) ABSTRACT

A computer-implemented system and method is provided for analyzing thermodynamic and mechanical properties and relationships between these properties for a molecule or collection of molecules within a chemical environment under given thermodynamic conditions. The system is based on user-defined rules for a free energy decomposition and its reconstitution, explicit solute and implicit solvent specifications, and a selection of thermodynamic condition.

20 Claims, 31 Drawing Sheets

(56) References Cited

OTHER PUBLICATIONS

Benson et al., Converting a maltose receptor into a nascent binuclear copper oxygenase by computational design; Biochemistry (2002), 41:3262-3269.
Bolon, et al., Enzyme-like proteins by computational design; Proc Natl Acad Sci U S A (2001), 98:14274-14279.
Dahiyat et al., De novo protein design: fully automated sequence selection; Science 1997, 278:82-87.
Kuhlman et al., Design of a novel globular protein fold with atomic-level accuracy; Science (2003), 302:1364-1368.
Tuchscherer et al., Protein design: on the threshold of functional properties; Biopolymers (1998), 47:63-73.
Kraemer-Pecore et al., Computational Protein Design, J Mol Biol (2001), 690-695.
Bornscheuer et al., Improved biocatalysts by directed evolution and rational protein design; Curr Opin Chem Biol (2001), 5:137-143.
Pokala et al., Review: Protein Design—Where We Were, Where We Are, Where We're Going; Journal of Structural Biology (2001), 134:269-281.
Park et al., Advances in computational protein design; Curr Opin Struct Biol (2004), 14:487-494.
Cozzetto et al., Ten years of predictions . . . and counting; FEBS J (2005), 272:881-882.
Schueler-Furman et al., Progress in modeling of protein structures and interactions; Science (2005), 310:638-642.
Korkegian et al., Computational thermostabilization of an enzyme; Science (2005), 308:857-860.
Kortemme et al., Computational redesign of protein-protein interaction specificity; Nat Struct Mol Biol (2004), 11:371-379.
Shukla et al., A designed protein interface that blocks fibril formation; J Am Chem Soc (2004), 126:13914-13915.
Daniel et al., The role of dynamics in enzyme activity; Annu Rev Biophys Biomol Struct (2003), 32:69-92.
Beadle et al., Structural bases of stability-function tradeoffs in enzymes; J Mol Biol (2002), 321:285-296.
Hollien et al., A thermodynamic comparison of mesophilic and thermophilic ribonucleases; H. Biochemistry (1999), 38:3831-3836.
Desjarlais et al., Side-chain and backbone flexibility in protein core design; J Mol Biol (1999), 289:305-318.
Su et al., Coupling backbone flexibility and amino acid sequence selection in protein design; Protein Sci (1997), 6:1701-1707.
Butterfoss et al., Computer-based design of novel protein structures; Annu Rev Biophys Biomol Struct (2006), 35:49-65.
Jacobs DJ, Predicting protein flexibility and stability using network rigidity: a new modeling paradigm. In Recent Research Developments in Biophysics. vol. 5. Trivandrum, India: Transworld Research Network; (2006): 71-131.
Jacobs et al., Protein thermodynamcis modeled by network rigidity; In Progress in Biopolymer Res. Hauppauge NY: Nova Science Publishers; (2008); 1-40.
Jacobs et al., Understanding the alpha-helix to coil transition in polypeptides using network rigidity: predicting heat and cold denaturation in mixed solvent conditions; Biopolymers (2004), 75:1-31.
Livesay et al., A flexible approach for understanding protein stability; FEBS Lett (2004), 576:468-476.
Carlson, H: Protein flexibility and drug design: how to hit a moving target; Curr Opin Chem Biol (2002), 6:447-452.
Carlson, H: Protein flexibility is an important component of structure-based drug discovery; Curr Pharm Des (2002), 8:1571-1578.
McCammon JA: Target flexibility in molecular recognition; Biochim Biophys Acta (2005), 1754:221-224.
Zavodsky et al., Modeling correlated main-chain motions in proteins for flexible molecular recognition; Proteins (2004), 57:243-261.
Celej et al., Protein stability induced by ligand binding correlates with changes in protein flexibility; Protein Sci (2003), 12:1496-1506.
Shrake et al., Origins and consequences of ligand-induced multiphasic thermal protein denaturation; Biopolymers (1992), 32:925-940.

Rosso et al., Evidence of a strong interaction of 2,4-dichlorophenoxyacetic acid herbicide with human serum albumin; Life Sci (1998), 63:2343-2351.
Perozzo et al., Thermodynamics of protein-ligand interactions: history, presence, and future aspects; J Recept Signal Transduct Res (2004), 24:1-52.
Eisenmesser et al., Intrinsic dynamics of an enzyme underlies catalysis; Nature (2005), 438:117-121.
Das, et al., Balancing energy and entropy: a minimalist model for the characterization of protein folding landscapes; (2005) PNAS, 102: 10141-46.
Lindorff-Larsen et al., Simultaneous determination of protein structure and dynamics; (2005) Nature, 433: 128-32.
Scheraga et al., Protein-Folding Dynamics: Overview of Molecular Simulation Techniques; (2007) Annu. Rev. Phys. Chem., 58, 57-83.
Freire E., Thermodynamcis of protein folding and molecular recognition; Pure & Appl. Chem. (1997) 69, 2253-2261.
Tai, K., Conformational sampling for the impatient; (2004) Biophysical Chem, 07, p. 213-220.
Cheluvaraja et al., Simulation method for calculating the entropy and free energy of peptides and proteins; (2004) PNAS, 101, 9241-46.
Munoz, V., What can we learn about protein folding from Ising-like models?; (2001) Curr. Opin. Struct. Biol, 11, 212-16.
Vendruscolo, M., Energetics of enzyme stability; (2002) Trends in Biotechnology, 20, 1-2.
Mark et al., Decomposition of the free energy of a system in terms of specific interactions. Implications for theoretical and experimental studies; (1994) J. Mol. Biol., 240, 167-176.
Dill, K.A., Additivity principles in biochemistry; (1997) J. Biol. Chem., 272, 701-704.
Jacobs et al., Elucidating quantitative stability-flexibility relationships within thioredoxin and its fragments using a distance constraint model; (2006) Journal of Molecular Biology; 358, 882-904.
Andricioaei et al., On the calculation of entropy from covariance matrices of the atomic fluctuations; (2001) J. Chem. Phys. 115, 6289-6292.
Hilser et al., Structure-based calculation of the equilibrium folding pathway of proteins. Correlation with hydrogen exchange protection factors; (1996) J. Mol. Biol., 262, 756-772.
Kamisetty et al., Free energy estimates of all-atom protein structures using generalized belief propagation; (2008) J. Comput. Biol. 15, 755-66.
Zhiyoung et al., Coarse-Graining Protein Structures With Local Multivariate Features from Molecular Dynamics; (2008) J. Phys. Chem. B 112, 14026-14035.
Jacobs et al., Protein flexibility predictions using graph theory; (2001) Proteins: Structure, Function, and Genetics, 44, 150-165.
Livesay et al., Conserved quantitative stability/flexibility relationships (QSFR) in an orthologous RNase H pair; (2006) Proteins 62, 130-43.
Wells et al., Constrained Geometric Simulation of Diffusive Motion in Proteins; (2005) Physical Biology, 2, S127-S136.
Jacobs et al., Network rigidity at finite temperature: relationships between thermodynamic stability, the nonadditivity of entropy, and cooperativity in molecular systems; (2003) Phys. Rev. E., 68, 061109, pp. 1-22.
Jacobs et al., Elucidating Protein Thermodynamics from the Three Dimensional Structure of the Native State Using Network Rigidity; (2005) Biophys. J., 88, 903-15.
Lee et al., Pebble Game Algorithms and (k,l)-Sparse Graphs; (2005) EuroComb, DMTCS proc. AE, 181-186.
Jacobs et al., Thermodynamics of a beta-hairpin to coil transition elucidated by Constraint Theory, Biopolymer Research Trends Ed: Pablo C. Sánchez. Nova Publishers, NY ISBN: 1-60021-984-5 45-76 (2007).
Mottonen et al., Unifying mechanical and thermodynamic descriptions across the thioredoxin protein family, (2008) Proteins 2009, 75:610-627.
Livesay et al., Hydrogen bond networks determine emergent mechanical and thermodynamic properties across a protein family; (2008) Chemistry Central Journal 2:17 1-20.
Vorov et al., Conformational entropy of an ideal cross-linking polymer chain; (2008) Entropy, 10, 285-308.

(56) References Cited

OTHER PUBLICATIONS

Zhang et al., Scoring function for automated assessment of protein structure template quality; Proteins: Structure, Function and Bioinformatics, vol. 57, 2004, pp. 702-710.

Kolinski et al., Assembly of protein structure from sparse experimental data: An efficient Monte Carlo model; Proteins: Structure, Function, and Genetics, vol. 32, 1998, pp. 475-494.

Definition of Monte Carlo simulation; Dictionary of Economics, Wiley, 1995, one page. Obtained online on Jun. 2, 2011 from <<http.//www.credorference.com/entry/wileyecon/monte_carlo_simulation>>.

Definition of Gibbs energy; The Penguin Dictionary of Science, 2009, one page. Obtained online on Jun. 3, 2011 from <<http.//www.credoreference.com/entry/penguinscience/gibbs_energy_free_energy_gibbs_function>>.

Beroza et al., Protonation of interacting residues in a protein by a Monte Carlo method: Application to lysozyme and the photosynthetic reaction center of Rhodobacter sphaeroides. PNAS, vol. 88, 1991, pp. 5804-5808.

Hydrogen bond, 2003, two pages, The Macmillan Encyclopedia. Retrieve online on Jun. 8, 2012 from <<http://www.credoreference.com/entry/move/hydrogen_bond>>.

\* cited by examiner

Before Bundling:

| List of clathrate disordered bars | | | List of native-like bars | | | List of mobile disordered bars | | |
|---|---|---|---|---|---|---|---|---|
| k | $\gamma$ | p | k | $\gamma$ | p | k | $\gamma$ | p |
| | | | | | | 23 | $\gamma'\cdot\gamma$ | p' |
| | | | | | | 22 | $\gamma'\cdot\gamma$ | p' |
| | | | | | | 21 | $\gamma'\cdot\gamma$ | p' |
| | | | | | | 20 | $\gamma'\cdot\gamma$ | p' |
| | | | | | | 19 | $\gamma'\cdot\gamma$ | p' |
| | | | 13 | $\gamma'\cdot\gamma$ | p' | 18 | $\gamma'\cdot\gamma$ | p' |
| | | | | | | 17 | $\gamma'\cdot\gamma$ | p' |
| | | | | | | 16 | $\gamma'\cdot\gamma$ | p' |
| | | | 12 | $\gamma'\cdot\gamma$ | p' | | | |
| | | | 11 | $\gamma'\cdot\gamma$ | p' | | | |
| | | | 10 | $\gamma'\cdot\gamma$ | p' | 15 | $\gamma'\cdot\gamma$ | p' |
| | | | 9 | $\gamma'\cdot\gamma$ | p' | | | |
| | | | 8 | $\gamma'\cdot\gamma$ | p' | | | |
| | | | 7 | $\gamma'\cdot\gamma$ | p' | | | |
| | | | 6 | $\gamma'\cdot\gamma$ | p' | | | |
| 4 | $\gamma'\cdot\gamma$ | p' | 5 | $\gamma'\cdot\gamma$ | p' | 14 | $\gamma'\cdot\gamma$ | p' |
| 3 | $\gamma'\cdot\gamma$ | p' | | | | | | |
| 2 | $\gamma'\cdot\gamma$ | p' | | | | | | |
| 1 | $\gamma'\cdot\gamma$ | p' | | | | | | |

After Bundling:

| Bundles of bars | | Capacity of bundles |
|---|---|---|
| b | $\gamma_b$ | $c_b$ = sum over occupation probabilities of all bars with same $\gamma_b$ |
| 1 | $\gamma_1$ | $c_1 = p$ |
| 2 | $\gamma_2$ | $c_2 = p'$ |
| 3 | $\gamma_3$ | $c_3 = p' + p'' + p''' + p''''$ |
| 4 | $\gamma_4$ | $c_4 = p' + p'' + p'''$ |
| 5 | $\gamma_5$ | $c_5 = p' + p'' + p''' + p'''' + p'''''$ |
| 6 | $\gamma_6$ | $c_6 = p' + p'' + p''' + p'''' + p'''''$ |
| 7 | $\gamma_7$ | $c_7 = p' + p'' + p'''$ |

Figure 23

COMPUTER IMPLEMENTED SYSTEM FOR QUANTIFYING STABILITY AND FLEXIBILITY RELATIONSHIPS IN MACROMOLECULES

CROSS-REFERENCE TO PRIORITY APPLICATIONS

This application is a continuation of commonly assigned U.S. application Ser. No. 12/344,192 for a "Computer Implemented System for Quantifying Stability and Flexibility Relationships in Macromolecules" (filed Dec. 24, 2008), now U.S. Pat. No. 8,244,504, which claims the benefit of U.S. Patent Application No. 61/016,551 for a "Computer Implemented System for Quantifying Stability and Flexibility Relationships in Macromolecules" (filed Dec. 24, 2007). Each of the foregoing patent applications is hereby incorporated by reference in its entirety.

STATEMENT REGARDING FEDERALLY SPONSORED RESEARCH

This invention was developed under National Institute of Health Grant No. 5R01GM073082. The Federal Government has certain rights in the invention.

FIELD OF THE INVENTION

The present invention is a computer-implemented system to reconstitute emergent thermodynamic and mechanical properties, and analyze their relationships in molecular systems based on network rigidity. The network rigidity is determined from constraints that model the interactions extracted from a free energy decomposition applied to the atomic structure. This invention has applicability to the fields of Computational Biology, Biotechnology, Chemistry, Material Science and Nanotechnology. The technical aspects of this invention derive from methods found in the fields of Mathematics, Physics, Chemistry, and Computer Science.

BACKGROUND

A long-standing objective in Computational Biology has been to accurately calculate free energy and other thermodynamic properties of a protein under specified chemical and thermodynamic conditions [1]. Furthermore, there is a desire to predict regions within a protein that are flexible and rigid, and locate the correlated motions important to biological function [2]. A fundamental problem that must be overcome by any computational method is to provide ample sampling over the accessible configuration space of a protein, or other molecular system of interest, in thermodynamic equilibrium. Computational methods used to solve these two problems can be classified into either dynamic [3] or thermodynamic [4] approaches. For all but the smallest of systems, computational time required to calculate thermodynamic properties is impractical, using a dynamic approach based on a molecular mechanics force field. Due to the inability of achieving statistically significant predictions of thermodynamic equilibrium properties of proteins, application of force fields remain untrustworthy, as their accuracy cannot be adequately tested.

The dynamic approach typically invokes molecular dynamics to propagate the equations of motion to simulate the evolution of a system to sample its configuration space [5]. Configuration space can be explored more effectively using efficient sampling methods, and by employing simplified force fields that involve coarse-graining. Coarse-graining reduces the number of degrees of freedom (hereinafter, "DOF") within a system that need to be dynamically considered, but also reduces accuracy of the simulation. Both techniques are routinely used in computational methods available in the field to advance understanding of myriad molecular systems, ranging from bulk water, polymers, nucleotides, proteins and membranes. The dynamic approach also uses Monte Carlo sampling to explore configuration space [6]. In the Monte Carlo method, each configuration is assigned an energy based on the molecular mechanics force field. From a Gibbs ensemble of generated configurations, thermodynamic and other physical properties can be readily calculated. Nevertheless, whether the equations of motion are propagated using molecular dynamics or Monte Carlo sampling is used, predictions of physical properties in thermodynamic equilibrium have not been possible for almost all practical purposes due to incomplete sampling of configuration space.

The thermodynamic approach identifies local conformation states that consist of a sub-ensemble of atomic configurations [7]. A free energy is assigned to these local conformation states, which is split into an enthalpy and entropy contribution based upon a corresponding molecular partition function. For any given conformation of a protein, or other system of interest, the total free energy is estimated as the sum of free energies over all free energy contributions that derive from each local conformation state. This procedure assumes enthalpy and entropy are additive [8]. Although additivity is commonly invoked, this assumption is generally incorrect [9,10] unless all local conformation states are non-interacting.

It is common to transform many interacting particles into a set of collective motions of particles, each with their own identity, and each acting independently. For example, a system of coupled springs between atoms is an excellent model for a solid. This collection of coupled interactions can be transformed into a collection of normal modes of vibration describing small oscillations about equilibrium. Unfortunately, this approach does not work well for macromolecules that are not completely rigid. As the conformation of a flexible molecular system varies over its accessible ensemble of configurations, the transformation into orthogonal normal modes depends on the conformation state [11]. Methods along these lines have been implemented within a dynamic approach, but still have limited ability to explore configuration space. In principle, the best free energy decomposition would be expressed in terms of independent variables to ensure that the assumption of additivity is a good approximation for conformational entropy [12].

Some thermodynamic approaches include explicit conformation dependence by expressing local free energy contributions in terms of local accessibility to solvent [13]. Generalized coordinates are used to keep the free energy contributions additive. The free energy contributions from implicit solvent molecules should be additive, however, because those molecules define the thermodynamic reservoir. Working only with solvent contributions to the free energy is incomplete. The source of non-additivity derives from intramolecular interactions related to conformational entropy. The assumption of additivity applied to just the enthalpy components appears not to pose problems. Non-additivity of conformational entropy enters because configuration space volume is overestimated when there is no account for overlap in the nominal configuration space volume associated with each isolated interaction. The additivity assumption breaks down in applications of proteins, and other biological polymers, because many competitive interactions couple to one another. Unfortunately, it is hard to separate the most important interactions because it is the collection of many weak interactions that is responsible for the observed emergent properties of interest. Consequently, the thermodynamic approach based on an additive free energy decomposition scheme will generally not be accurate, and predictions from these models remain untrustworthy.

Despite the intrinsic problems associated with a thermodynamic approach, it is frequently cast into a coarse-grained statistical mechanics problem, where all accessible conformation states of the molecular system are considered. The free energy of each conformation is estimated by adding the free energy contributions of each local conformation state. In these models, the initial atomic structural details are lost in exchange for a coarse-grained description. As a result, coverage of configuration space to account for the flexibility in protein structure is much better than the dynamic approach. However, the procedure to account for the diversity in configuration space is non-trivial, requiring summing a partition function. In general, it is not possible to sum a partition function exhaustively, even for coarse-grained (or reduced) models. Common techniques for estimating a partition function based on a thermodynamic approach are Monte Carlo sampling, various mean-field approximations or transfer matrix methods for special cases. Another common approximation scheme is to limit the type of configuration states by assuming native-like interactions can break or form, but all other non-native interactions are simply ignored. Using various techniques or combinations thereof, partition functions can be calculated with reasonable accuracy.

Unfortunately, even when a method is used to accurately calculate the partition function for a model using the thermodynamic approach [14], it still returns poor predictions because the additivity assumption of free energy is fundamentally flawed. These models are usually defined in terms of variables that classify local conformations into discrete states void of atomic coordinate information. These models, referred to as Ising-like models, are intrinsically less accurate due to their simplifying approximations. The advantage of these methods is that they provide relatively fast practical computations while giving good coverage of the accessible configuration space. For this reason, a thermodynamic approach is often referred to as an ensemble-based approached. Although the thermodynamic approach has undoubtedly been the most successful way to assess thermodynamic properties of proteins, it remains untrustworthy.

The mechanical properties of a protein that are of particular interest is to determine which parts are flexible and rigid, and which parts influence other parts through cooperative motions [15]. Determination of this type of mechanical information is routinely obtained by using a dynamic approach. The root mean squared deviation in atom positions indicates which regions are flexible or rigid. Principal component analysis of a covariance matrix of atomic motions identifies correlated motions. These results are limited to short time correlations, however, because the statistics are generally not sufficient to be consistent with thermodynamic equilibrium averages. The thermodynamic approach is generally inadequate to describe these mechanical attributes, since they typically employ binary coarse-graining into native-like or disordered states of an entire residue. Correlations at the residue level are readily determined, as well as the average degree that a residue is disordered (locally unfolded) or native-like. The residue-state measures of native-like and disordered are often treated as analogous to the mechanical property of rigid and flexible respectively. Common thermodynamic approaches have no direct connection to mechanics.

A third method exists that models protein structure as a network of distance constraints, from which rigid and flexible regions are identified using network rigidity [16,17]. Although this method provides precise calculation of rigid and flexible regions and correlated motions, it does not account for constraints breaking and new ones forming due to thermodynamic fluctuations. Rather, the distance constraints are determined based on a static protein structure in the native state. Unfortunately this restriction is severe, because proteins undergo many fluctuations in conformation, meaning that an ensemble-based approach is essential to describe thermal equilibrium properties. This mechanical a-thermal modeling of a protein as a fixed distance constraint topology has limited applicability in describing proteins in their native state. This method has been combined with a dynamic approach actively and passively for post-analysis. The former hybrid combination has been implemented as a Monte Carlo geometric simulation [18]. The efficiency in exploring the native state ensemble dramatically increases. Because native constraints do not break and new constraints do not form, however, equilibrium properties cannot be obtained.

A Distance Constraint Model (DCM) is an innovative type of thermodynamic approach that combines free energy decomposition with constraint counting [19,20]. Atomic interactions are modeled by distance constraints, each assigned an enthalpy and entropy value. As the conformation of a protein changes, different sets of constraints will be present. An ensemble of constraint topologies represents all accessible conformations. For a given constraint topology within the ensemble, network rigidity is used to determine which distance constraint is independent or redundant. Total enthalpy is taken to be the sum of enthalpy contributions from all constraints within the network. The sum of entropy contributions from independent constraints gives an upper bound estimate for the conformational entropy. Although the total numbers of independent and redundant constraints are unique, identification of which constraint is independent or redundant is not unique. Therefore, many upper bound estimates for conformational entropy are possible.

Graph algorithms that calculate generic properties of network rigidity, such as identifying independent and redundant constraints, are commonly called pebble games [21]. The operational procedure to identify independent constraints requires recursively placing distance constraints in the network one at a time until all constraints are placed. Giving preference to constraints with lower entropy to be placed in the network before those with greater entropy ensures the lowest possible upper bound estimate for conformational entropy. The pebble game algorithm combined with this preferential rule must be applied to each distinct constraint topology within the ensemble. Finally, the partition function is obtained by summing over all accessible constraint topologies within the ensemble, and there are various ways to solve this. This algorithm is set forth in part in U.S. Pat. No. 6,014,449 (Jacobs et al.) which is incorporated by reference in its entirety.

The DCM was solved using an exact transfer matrix method for the alpha helix to coil transition [19], but this method is not general. The DCM was also solved using Maxwell constraint counting, which is formally a Mean-Field Approximation (MFA) applied to the density of constraints within a network [22]. For proteins, a minimal DCM (mDCM) was solved using a MFA combined with Monte Carlo sampling [20]. This hybrid method exhibits a good balance between calculation speed and accuracy. In this method, the occupation probability of a bar is pre-calculated within a MFA using Lagrange multipliers that enforce certain numbers of native torsion constraints, $N_{nt}$, and hydrogen bonds (H-bonds), $N_{hb}$, within the protein. Given a set of occupation probabilities, $\{p_b\}$, for all bars in the network, Monte Carlo sampling is employed, which requires playing the pebble game to place the bars preferentially in the network per Monte Carlo move. A pseudo uniform random number generator on the interval [0,1] is used to determine if a bar is present or not by comparing the random numbers to the occupation probabilities. By repeating the process of building up a constraint network hundreds of times, an ensemble of constraint topologies is generated for different macrostates characterized by ($N_{nt}$, $N_{hb}$). For each macrostate, average enthalpies and entropies are calculated. Note that the probability for a bar to be independent depends on occupation probabilities of all bars in the network, $\{p_b\}$. Within this MFA, the set of bar occupation probabilities, $\{p_b\}$, are assumed not to depend on whether these bars are independent or redundant.

The mDCM is a crude model because it treats all residues in the same way, meaning all residues are considered to have identical properties irrespective of chemical composition and location in the protein. To capture essential effects of network rigidity from the hydrogen bond network, the mDCM employs three empirical parameters determined by fitting the DCM predictions for excess heat capacity against experimentally measured heat capacity. This fitting procedure works well, and the mDCM proves to be the only all-atom model that can successfully reproduce measured heat capacity curves for protein folding while providing a QSFR analysis [23,24,25,26,27]. Although the mDCM has established the fundamental premise that non-additivity of entropy is intrinsically related to network rigidity, predictions are limited in utility and are untrustworthy due to its oversimplifications. Presumably, at the expense of computational efficiency, significant flaws and drawbacks can be eliminated as the DCM becomes more sophisticated. Compared to the state of current art in the field, the unconventional paradigm employed in the DCM for simultaneously calculating emergent thermodynamic and mechanical properties shows much promise.

It appears one can choose between two options. Construct a simple model and solve it well with good coverage in conformation space, but then accept inaccurate predictions due to errors caused by underlying flawed assumptions. Alternatively, apply an accurate model that cannot be solved without simulation, and make inaccurate predictions because not enough conformation space is explored. This invention provides the means for a third option. A computer-implemented system within a DCM is described that removes oversimplifications related to free energy decomposition by; a) improving detailed all-atom representation of intramolecular interactions, b) includes solvent interactions, c) strain energy, d) effect of vibrations, e) more accurately calculates the partition function, and f) does calculations faster than previously possible.

In terms of prior patent publications related to the invention herein, European Patent 1,025,521 (Freire 2007) uses the free energy minima for identifying target binding sites on a molecule of interest and methods for designing ligands which bind to a molecule of interest. Binding targets in the protein are identified and classified according to their optimal affinities. In calculating the Gibbs free energy, a computer program accepts the three-dimensional coordinates of each of the atoms. The computer program then determines the difference between the Gibbs free energy of the complex of the ligand and the macromolecule and the uncomplexed ligand and the uncomplexed macromolecule. The Gibbs energies of all the partially folded states are calculated using the structural parameterization of the energetics in conjunction with a set of structural parameters optimized for the unfolded states. The partially folded state with the highest probability is the one with the lowest Gibbs energy.

BRIEF SUMMARY OF THE INVENTION

Proteins are macromolecules consisting of many noncovalent interactions that determine their three-dimensional structure and stability. A critical link between structure and stability is conformational flexibility, also important for function. For example, enzymes must be flexible enough to mediate a reaction pathway, yet rigid enough to achieve molecular recognition. A difficult challenge is to accurately predict protein flexibility and stability under a given thermodynamic and solvent condition, and be fast enough for high throughput applications. To this end, a computer-implemented system and method is described to carry out efficient calculations within a Distance Constraint Model (DCM). The DCM is based on a paradigm that combines constraint counting with free energy decomposition. The problem of non-additivity in contributions to conformational entropy is resolved by regarding network rigidity as an underlying interaction. Many different mechanical and thermodynamic properties and their relationships are readily calculated, which define Quantitative Stability/Flexibility Relationships (QSFR). The layout shown in FIG. 1 depicts the major elements that compose the computer-implemented system and method.

The computer-implemented system and method provides a Flexibility And Stability Test (FAST) on a template structure or a set of template structures, for which pertinent details are contained in the explicit solute specification provided by the user. The user also provides the implicit solvent specification, which defines parameters that describe the chemical nature of the solvent and the thermodynamic condition. The user requests various types of QSFR output to perform queries, consisting of different types of measures to characterize equilibrium properties concerning global and local thermodynamic and mechanical response. User inputs of these types are required during routine application of the computer-implemented system. In addition, the FAST calculation is based on user-defined specifications for the Free Energy Decomposition (FED) and Free Energy Reconstitution (FER).

The FED specifies how a molecular structure is partitioned into distinct types of interactions that have enthalpy and entropy contributions, and how intra-molecular interactions map to distance constraints. The FER specifies primary order parameters, and the method for constraint counting. Combining the FED and FER rules define different distance constraint models in an analogous way molecular dynamics simulation can be based upon different mechanical force fields. The computer-implemented system and its methods provide a general purpose DCM solver that delivers a FAST calculator. That is, different FED and FER schemes can be selected in different combinations using a schema of universal character. It is expected that a given DCM may be better than another in some attributes, but not as good in other attributes.

The FED specifies how local solvent states are assigned to each residue, and defines the nature of the solvent interaction to account for chemical diversity. The presence of an intramolecular interaction will generally depend on the local solvent states of the residues. Atomic structural information is mapped onto a constraint network involving rigid bodies. Intramolecular interactions will generally depend on local solvent states within a template structure, and are modeled as constraints between rigid bodies.

In general, an intramolecular interaction is represented by $n_c$ constraints, where $n_c \geq 1$. Each constraint is allowed to absorb one DOF when it is independent. When only two rigid bodies are involved in the interaction, a constraint reduces to a distance constraint, which was the original basis for the DCM. A generalized form of the DCM now allows multiple bars to represent one distance constraint. Furthermore, a constraint can be distributed over a region, such that multiple bars are placed between many distinct pairs of rigid bodies.

Local molecular partition functions are expressed in terms of various types of constraints, and the set of bars that comprise those constraints. In practice, a distributed constraint is associated with correlated motions of atoms that can be identified using methods such as normal mode or principle component analysis applied to subsystems of interest in defining the FED. A constraint network defines a multigraph composed of vertices connected by edges that generally consist of multiple bars. See U.S. Pat. No. 6,014,449 (Jacobs 2000). The multiple bar representation of a distance constraint and the distributed constraint embodiments require assigning to each bar a capacity for how many DOF it can absorb. The preferred embodiment of the computer-implemented system and method will manifest universal characteristics, and as such, the mDCM can be recapitulated as a special case.

The molecular partition function, $Z_{int}$, for an intramolecular interaction is represented as a factored product of $n_c$ partition functions, such that $Z_{int} = Z(1)Z(2) \ldots Z(n_c)$ where $Z(j)$ corresponds to the partition function of the j-th constraint. Enthalpy contributions are typically assigned to an interaction but can be assigned to constraints or bars. Each bar is assigned conformational entropy. When an interaction is hypothetically isolated, its total free energy contribution is given by the sum of enthalpies and entropies initially assigned as bare values. Additivity follows because $Z_{int}$ has a factorized form. However, when the interaction couples to other interactions, the constraint network and FER rules renormalize the enthalpy and entropy values. The preferred embodiment preserves the mathematical form of the equations that describe bar occupation probabilities, which involve local enthalpies and entropies. Local enthalpies and entropies renormalize to new values depending on the coupling of interactions through network rigidity within the constraint network. A canonical form of the equations to calculate the total free energy of a protein is expressed in terms of the set of bar occupation probabilities, $\{p_b\}$, and conditional probabilities for bars to be independent, $\{q_b\}$, and a collection of renormalized local enthalpy and entropy values. In the claims one occupation probability or the set thereof, $\{p_b\}$, is referred to as P, and one conditional probability for a bar to be independent, or set thereof, $\{q_b\}$, is referred to as Q.

The FER rules determine how individual free energy components within a constraint network are to be combined to obtain the total enthalpy and entropy of a protein. Solvent entropy is additive over all contributing constituents, while conformational entropy is additive only over independent bars. A self-consistent MFA is implemented to construct an ensemble of constraint topologies. In relation to constraint counting, this approach will henceforth be referred to as Self Consistent Constraint Theory (SCCT). Application of SCCT provides greater accuracy than mean-field theory. In SCCT, the set of conditional probabilities for bars to be independent, $\{q_b\}$, are used to renormalize local enthalpies and entropies, which in return affect the set of occupation probabilities, $\{p_b\}$. Implementation of SCCT has the generic form: Initially guess $\{q_b\}$ and from the FED provide initial bar values for component enthalpies and entropies. At an iterative step, calculate $\{p_b\}$ based on the current component enthalpies and entropies. Perform network rigidity calculations to obtain the resulting $\{q_b\}$ based on the given $\{p_b\}$. Using $\{q_b\}$, renormalize component enthalpies and entropies for new current values. Repeat the iterative step until convergence within a pre-defined acceptable tolerance is achieved in $\{p_b\}$ and $\{q_b\}$.

Within SCCT, the method used to calculate network rigidity properties can be varied. For example, the hybrid method that involves Monte Carlo sampling can be applied. However, due to the increased complexity of the DCM when expressed in a canonical universal form, and because of statistical errors due to random and incomplete sampling, Monte Carlo sampling will generally be slow and undesirable. Therefore, other methods to calculate network rigidity properties in terms of probability functions for the DOF within a constraint network are incorporated in this computer-implemented system as selectable embodiments. The advantage of directly using probabilities is that no statistical errors are present. The calculations retain only numerical error from machine precision limitations, which are well below error levels required to achieve high accuracy. The computation time is dramatically reduced by a factor equal to the minimum number of samples required in the Monte Carlo method to obtain sufficiently small error bars to converge without sacrificing accuracy due to noise. Each of these advantages individually outweighs the disadvantage that the probability distribution functions for DOF within the network are calculated within a MFA. A MFA is accurate when applied to long-range interactions, which is the case for network rigidity. Since a MFA will invariably be made in some form, the preferred embodiment is to work directly with probability functions describing DOF. Within a pebble game, a pebble locates where a DOF is present in the network. The probability for a DOF is henceforth referred to as a virtual pebble that has a fractional weight ranging from [0,1] corresponding to the probability that the pebble is present.

The most efficient but crudest approximation to constraint counting is to apply Maxwell Constraint Counting (MCC). In MCC, as constraints are placed in the network, they are assumed to be independent until the network has the minimum number of constraints necessary to make it globally rigid. This critical minimum number of constraints is referred to as the Maxwell level. Constraints placed after the Maxwell level is reached are assumed to be redundant. The MCC neglects fluctuations that allow some regions to be rigid and over-constrained while other regions flexible and under-constrained. The MCC is included as the preferred embodiment when calculation speed for thermodynamic properties is more important than obtaining high accuracy during high throughput screening applications. However, when higher accuracy is desired, or when mechanical properties are desired, the user must switch to a more accurate constraint counting method within the FER, such as one implemented as a Virtual Pebble Game (VPG).

The VPG translates the Standard Pebble Game (SPG) that tracks DOF in terms of pebbles within a network into tracking the probability for a DOF (i.e. virtual pebble) to be absorbed by bars. The VPG is interpreted as moving pebbles around similar to the SPG except bars are assigned capacities and fractional pebbles are allowed. One play of the VPG is equivalent to an average of multiple plays of the SPG over all accessible constraint topologies. For example, if there are 1,000 fluctuating constraints within a network that may or may not be present, then there are $2^{1000}$ accessible constraint topologies. In this case, the VPG is about $2^{1000}$ times faster than finding the exact average for the SPG. In practice, the number of Monte Carlo samples generated using the SPG was a few million in applications employing the mDCM. However, when applying SCCT to a more sophisticated FED, the number of Monte Carlo samples to produce usable estimates will surely increase by large factors to keep statistical error bars low. Since one play of the VPG takes nearly the same time to play as the SPG, the VPG will yield computational savings that are at least a factor of 200, while factors of more than 200,000 would not be surprising. Besides increase in speed, the VPG has no error bars due to statistical sampling.

For a given template structure, the computer-implemented system and method accounts for four effects using the preferred embodiments related to the FED and the iterative self-consistent FER. The first effect is that as additional constraints are added to a rigid region, this invention can account for reduction in conformational entropy as the region stiffens. Simultaneously, the second effect relates to an increase in number of redundant constraints with concomitant increase in energy due to strain propagating through the over-constrained region. The third effect is that the frequency spectrum of normal modes throughout a structure shifts to higher frequencies as regions stiffen. A preferred embodiment for the FED includes a vibration contribution to the free energy based on network rigidity properties after they are calculated. The fourth effect is to include solvent interactions in many different ways that have additive entropies, and probabilities of solvent states are related to the type of constraint topology. This fourth feature allows for consideration of a complete set of interaction types as either being additive or nonadditive in nature.

BRIEF DESCRIPTION OF THE FIGURES

FIG. 23: An example of how sets of bars constitute different interaction types, and how they get bundled together.

DETAILED DESCRIPTION

Glossary

Figure 1:
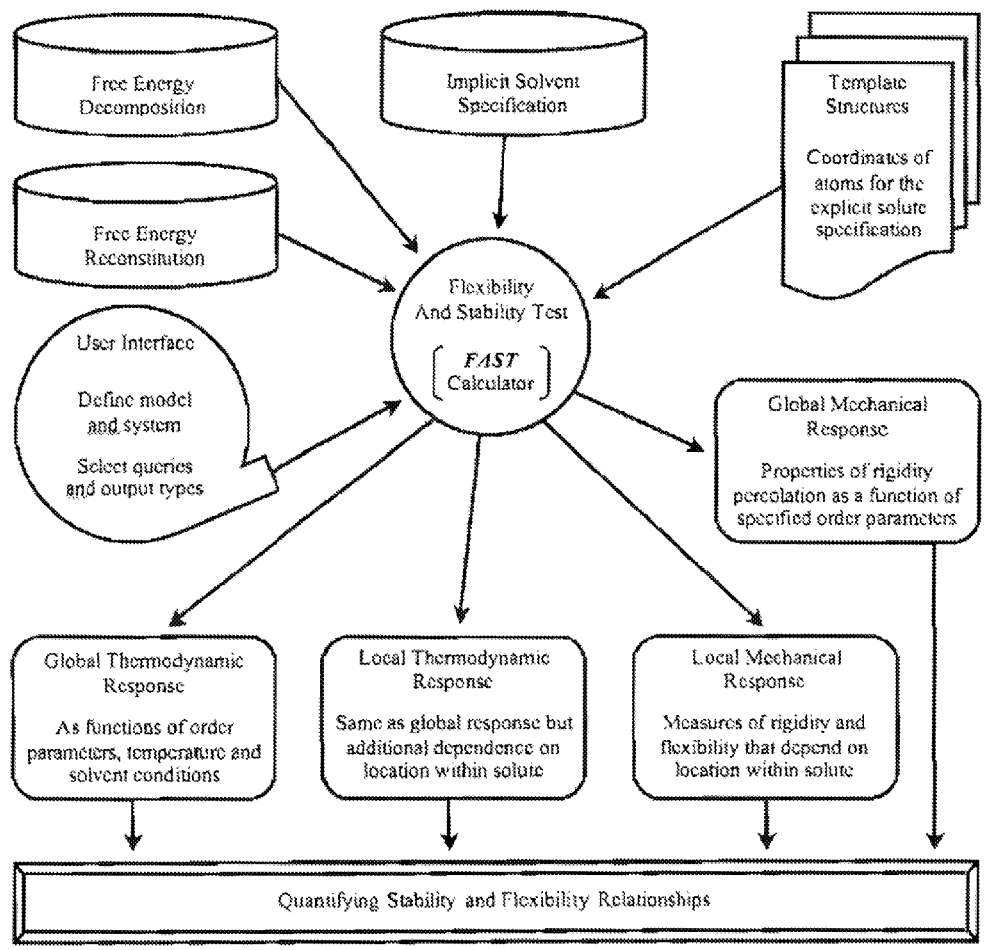
FIG. 1: Schematic diagram showing major elements of the computer-implemented system and method.

Accessible microstate: An allowed state of a system that can be reached as the system evolves over an observation time. The term "accessible" is used when considering a particular macrostate. For example, diamond and graphite define two different macrostates of carbon material. The macroscopic properties of graphite and diamond differ as a result of the difference in the ensemble of microstates each substance explores. At standard temperature and pressure, graphite is more stable than diamond, yet, it is said that diamonds last forever. Diamond is in a metastable state, meaning that its atoms cannot rearrange to form graphite. Microstates of graphite and diamond are not accessible at standard pressure and temperature conditions over a geological time scale. A similar effect occurs in proteins. The microstates of a folded protein can be inaccessible to an unfolded protein or vice-versa depending on how big the free energy barrier is between the two thermodynamic states. The partition function can be calculated using only accessible microstates to account for metastable macrostates.

Additive free energy contribution: The free energy of the i-th component part of a system is given by $G_i=H_i-TS_i$ and the total free energy over all component parts is just the sum of $G_i$. That is $H_{total}=\Sigma_i$ Hi and $S_{total}=\Sigma_i$ Si.

Atomic configuration: A specific realization of all atomic coordinates within a system.

Atomic packing interaction: A localized type of interaction that tends to keep pairs of atoms an optimal distance apart, and prevents atoms from passing through one another.

Bars: Provide strict distance constraints between objects such as atoms or rigid bodies.

Body-bar multigraph: A graph for which vertices represent objects, and edges in the graph connecting pairs of vertices represent bars. More than one edge can connect between two vertices.

Boltzmann factor: The mathematical form $\exp(-\beta E)$ with $\beta=1/(RT)$ where R is the universal gas constant and T is temperature in units of Kelvin, and E can be energy or enthalpy. A partition function is a sum over Boltzmann factors over an ensemble of microstates.

Bundle of bars: A collection of bars that all span the same pair of vertices in the body-bar multi-graph, and all have the same assigned conformational entropy are converted to a single bar.

Buried solvent state: A macrostate of a molecular constituent that defines a hydrocarbon-like chemical environment that is typically found in the interior of aqueous globular proteins.

Coarse-graining: When a continuous variable is partitioned into a collection of bins so that the state of a system is described by the occupation of bins, losing the details of the original variables.

Component parts: A system is sub-divided into molecular constituents and interaction types based on a free energy decomposition scheme in terms of a group of atoms. The interactions between these atoms are assigned a free energy contribution based on the geometry of the atoms.

Compound phase transfer: Transferring a molecule from one chemical environment to another creates a change in thermodynamic response due to solvation effects. As a result, the free energy of a molecule in a buried environment will be different than when it is exposed to solvent. Also see hydrophobic interaction.

Conformational entropy: The entropy contributions that are related to the degeneracy in geometrical motions for a given set of mechanical constraints. This portion of entropy is nonadditive, and is estimated from the properties of network rigidity using constraint theory.

Degeneracy: Number of microstates, $\Omega$, sharing the same global properties of a system. Usually one of the global properties is energy or enthalpy, where all microstates have the same Boltzmann factor. Conformational degeneracy deals with the number of distinct atomic configurations consistent with all imposed mechanical constraints present.

Degrees of freedom: The set of variables needed to specify all atom coordinates within a system, denoted as DOF.

Electrostatic interaction: Interactions involving Coulomb's law in dielectric media. Some short-range electrostatic interactions are not counted as such, but rather built into other interaction types.

Emergent properties: Properties exhibited by a system due to collective contributions from molecular constituents and interaction types that cannot be predicted based solely on the intrinsic properties of individual molecular constituents and interaction types.

Exposed clathrate-solvent state: A macrostate of a molecular constituent representing local interactions of solvent molecules that from a clathrate structure. As a result, the conformation of the molecular constituent is severely confined. In aqueous solution, this effect is commonly related to hydration, sometimes referred to as iceberg-like water.

Exposed mobile-solvent state: A macrostate of a molecular constituent characterizing a local chemical environment typical of interacting solvent molecules that are mobile, not restricting the intrinsic accessible conformation space of the molecular constituent.

Free energy decomposition: Complete specification of how a system is sub-divided into component parts, and the assignment of a free energy function for each of these component parts. The free energy function is based on the solvent state of a given component part, the determination of its number of degrees of freedom, its geometrical characterization that may be used to define multiple states, the constraint type used to assign an entropy to each degree of freedom, the number of bars used to represent each constraint, and the assignment of enthalpy and entropy values for each of these bars. Although, a free energy decomposition is model dependent and not unique, it must be applicable to an arbitrary template structure within the range of application of interest.

Free energy landscape: Is the free energy of a system when it processes properties that define a specific macrostate, which is expressed in terms of D variables. Plotting free energy against these D variables provides a D-dimensional landscape. In this context, the macrostates are order parameters. For one order parameter, a "1-D free energy landscape" can be plotted on a 2D graph. For two order parameters, it is possible to provide a three-dimensional perspective picture. When more than 2 order parameters are involved, only cross sections can be viewed.

Hydration interaction: A local interaction type involving water molecules that form clathrate structure. The affect of the clathrate structure is modeled using a variety of local distance constraints. For generality purposes, this is also referred to the clathrate conformation interaction. In aqueous solution, it is just a hydration interaction.

Hydrogen bonds: A specific type of bond in chemistry where there is sharing of a proton between a donor and acceptor atom. The hydrogen bond has partial nature as a covalent bond, but is greatly influenced by local electrostatic interactions. Like all bonds, their property is only properly understood using quantum mechanics. Hydrogen bonds are modeled as a specific interaction type that is modeled in terms of constraints and bars. Note that salt bridges are treated as a special type of hydrogen bond.

Hydrophobic interactions: A many body interaction responsible for the tendency of hydrocarbon-like molecules to aggregate in an aqueous solvent, which exhibits an apparent repulsion between water and hydrocarbons. This interaction is modeled as an additive free energy of solvation. The process of transferring water molecules from a buried region in a protein to aqueous solution models the additive part of the hydrophobic interaction. See Compound phase transfer. In addition, when water is expelled to the bulk solvent, there is potential contact between the molecular constituents within the system. These contacts are modeled with an inter-residue interaction that involves nonadditive conformational entropy contributions.

Implicit solvent specification: Defines all chemical properties of the solvent that the solute is placed in. This would include pH, ionic strength, concentrations of all co-solvents and other solutes.

Interaction types: Interactions between a group of atoms in local proximity are classified into types, such as covalent bonds, hydrogen bonds, hydration, and the hydrophobic interaction. Each interaction type is assigned a free energy contribution based on the geometry of the atoms as part of the free energy decomposition scheme.

Kinetic trap: A stable thermodynamic state of a system with a free energy that is not as low as that of another stable thermodynamic state, and there is a high free energy barrier that makes this metastable state extremely difficult to escape out of.

Lagrange multiplier: Enforces certain global properties of a system described by order parameters that define a macrostate.

Macrostates: Observed properties of a system based on a sub-ensemble of accessible microstates that reflect these properties.

Mechanical constraint: Fixes the distance between a point on one object to a point on a second object. More generally, it removes a degree of freedom as it sets a variable to be a specific value, or to be limited to within a window of allowed values using a coarse-grained description.

Mechanical linkage: The ensemble average properties of network rigidity that reflect fluctuations of constraints breaking and forming. The probabilities for constraints to be present or not are determined by Boltzmann factors that themselves depend on the network rigidity properties.

Molecular conformation: Coarse-grained set of an infinite number of related atomic configurations.

Molecular constituents: A system is decomposed into numerous groups of atoms that define building blocks or interaction types. Often groups of atoms define molecules, but not necessarily.

Molecular free energy function: A free energy function is related to the partition function, Z, such that $G=-RT \ln(Z)$ where Z=sum over all Boltzmann factors for all accessible microstates of a given system. A molecular free energy function describes a specified molecular constituent and its local chemical environment, and is well-defined using the coarse-graining process.

Native interactions: Interactions form when the local atomic geometry and environment are suitable. The interactions identified based on a template structure are classified as native.

Node free energy: The free energy of a particular macrostate expressed as a multi-variable function using order parameters that characterize global properties of the system. Macrostates are represented as nodes in a D-dimensional grid to represent the free energy and any other physical property of interest.

Order parameter: A global property of a system is identified and its thermodynamic average calculated over an ensemble of accessible microstates that all share the same global property. The value of this global property can change continuously, and defines the order parameter. Usually the global property is selected to discern whether a system is in an ordered or disordered state. For example, the number of hydrogen bonds within a protein can serve as an order parameter. The greater the number of hydrogen bonds implies a more ordered structure.

Partition function: Is a standard term to denote a series of Boltzmann factors. A partition function can be constructed over different ensembles of accessible microscopic states, and a variety of constraints on the system, such as fixed energy, temperature, pressure, volume, etc.

Pebble capacity: The maximum number of degrees of freedom a bar or a bundle of bars can remove from a network.

Proximity configuration: Provides the geometrical aspects of the molecular constituents within a given template structure which are used to define native-like states, and specifies all accessible geometrical and solvent states that will generally not be native-like.

Solvent entropy: Additive entropy contributions related to the degeneracy of accessible configurations of solvent molecules interacting with molecular constituents within the system.

Statistical Mechanics: The field of physics that describes emergent properties of systems of particles.

Statistical weight: Partial sums of Boltzmann factors define the weight of accessible states that define a group, divided by the partition function, which is given by a sum over all Boltzmann factors. This ratio defines the probability of finding an accessible state to be one of those identified in the group. Usually the groups are constructed based on well-defined common properties.

Template structure: A particular atomic configuration of a system, which can be used to identify native interactions. Different native interactions are associated with different template structures.

Thermodynamic environment: Specifies temperature, pressure, volume and possibly other external conditions such as magnetic and electric field strength.

Thermodynamic properties: A generic term that includes all possible response functions found in the field of thermodynamics, such as free energy, enthalpy, entropy, heat capacity, pressure, and an endless variety of susceptibility functions. From statistical mechanics, thermodynamic properties are statistical averages of a well-defined property over accessible microstates that are assigned probabilities that reflect thermodynamic equilibrium.

Torsion angle interaction: Within a covalent bond involving four connected atoms, the two that are in the middle are primary atoms. A dihedral angle defines the relative orientation of two planes defined by three consecutive atoms on each end with respect to an axis that runs between the primary atoms. This rotation has an energy associated with it, and can be considered as a separate interaction types, or can be lumped together with other interactions.

Overview

The computer-implemented system and method enables a user to apply a FAST calculator to a protein represented by multiple template structures, labeled by index (ts). In applications, template structures may be selected based on known three-dimensional atomic coordinates from X-ray crystallography, NMR or other means such as random generation. A template structure represents a single conformational state. The FED is based on perturbing around this state, and is annotated as native-like. For each template structure, thermodynamic and mechanical equilibrium properties as a function of Primary Order Parameters (POP) are calculated. The utility of user-selected POP is to classify distinct macrostates that characterize certain physical properties. Any template structure can be in one of the macrostates defined by POP. The FAST calculator determines the free energy, G, as a function of chemical environment (CE), thermodynamic condition (TC), the macrostate defined by POP and template structure, ts. The multivariable free energy function is schematically given as G(CE, TC, POP, ts), where CE, TC and POP represent a set of relevant variables. A single protein may require multiple template structures to accurately predict thermodynamic and mechanical properties, which adds another dimension to the free energy landscape.

As a consequence of employing a SCCT, improving detailed all-atom representation of intramolecular interactions, modeling solvent interactions, employing multiple template structures, accounting for effects of strain energy and vibrations, the Monte Carlo method for the FER used in the mDCM becomes inadequate. Although improvements to the FED and the use of SCCT within the FER will markedly increase accuracy within the DCM paradigm, they created a stumbling block in terms of an unprecedented computational challenge. This computer-implemented system and method formulates the general schema for a sophisticated FED, and non-statistical sampling methods for the FER that are more accurate and faster than those used in the mDCM. Due to the universal character of the preferred embodiment as a general purpose DCM solver, the mDCM can be solved as a special case of this invention. However, this invention not only makes the mDCM obsolete, its range of applicability extends to all types of molecular systems, and is therefore applicable to molecular liquids, such as water, and to peptides, proteins, other polymers, nucleotides, micelles, membranes and viruses within polar and non-polar solvents. Example applications extend to characterizing protein-protein interactions, ligand docking, and for the design of proteins and molecular assemblies.

Self-Consistent Constraint Theory

Self-consistent Constraint Theory (SCCT) is an iterative method of solving the Distance Constraint Model (DCM) within the framework of Mean Field Theory (MFT). After setting up preliminary mathematical scope, SCCT will be fully explained and developed. This section is broken up into four main parts: Mathematical scope, review of MFT as it is applied to minimal DCM, overview of SCCT as it is applied to the DCM, and the mathematical and technical details of DCM/SCCT implementation.

Mathematical Scope for DCM/SCCT

There are key concepts that will be introduced, and then they will be combined mathematically to set up for the development of the DCM, and solving it using SCCT. These concepts are:
1. Ensemble of template structures
2. Representing molecular structure by graphs
3. Ensemble of proximity configurations
4. Ensemble of constraint topologies
5. Projections, sub-ensembles and partition functions Upon arriving at combining the conceptual aspects into a mathematical expression for the partition function, a discussion about free energy decomposition will be given. In particular, the last sub-section will cover mathematical notation to describe a model independent free energy decomposition.

Template Structure

A template structure is a particular atomic configuration of a system, which can be used to identify native interactions. Different native interactions are associated with different template structures. One basic concept here is the underlying three dimensional structure of the molecule. This structure defines the position coordinates of all atoms. This structure can be obtained from experimental data, such as X-ray crystallography, NMR spectroscopy or neutron diffraction to name but just a few. The structure can be a model that is generated, and, for purposes of computing the free energy, the structure need not mirror the exact molecule in a physical sense. The template structure (ts) is the most important aspect of the DCM/SCCT approach because from it, all calculations are constructed. Note that in prior work [19] dealing with the alpha-helix to coil transition or the beta-hairpin to coil transition [22], a template structure was effectively used. In these cases, the model was so simplified that the atom coordinates never were specified explicitly. Nevertheless, a template structure, albeit a generic one, was used because the beta-hairpin and the alpha-helix structural motifs were invoked in the calculations. In prior work on proteins using mDCM, researchers used files from the Protein Data Bank. In general, the model of this invention can use any template structure, even one that is randomly generated having no physical basis whatsoever.

In almost all applications of the DCM/SCCT more than one template structure will be used to represent the molecule. If the molecule is 100% rigid, and never changes its conformational state, then in this case, only one template structure is needed. If a protein can explore many different conformational states within its native fold basin, and it can unfold either by heating, cooling, or, pressure induced, denaturant induced, pH induced, or otherwise destabilized, then, perhaps one template structure is sufficient. This latter example describes a two-state protein, where it can either be in the unfolded or folded basin. The protein must traverse a transition state to move from one basin to another. The nature of this transition state will depend on the mechanism causing the native protein to unfold. For any of these infinitely many cases, it might happen that one template structure is sufficient to represent the native fold-basin. However, nothing prevents using 2 templates, or 5, or 10, or even 100 template structures! The important point is that unless an intermediate state physically exists, other template structures would be expected to provide small increases in accuracy compared to using only one template structure to represent the native fold basin.

The goal of the DCM/SCCT is to find a set of template structures that forms a near complete basin within a large structure-vector space. The unfolded state is a random vector in this structure-vector space, whereas, a single native fold basin requires only one template structure. Each intermediate stable basin would similarly require a template structure. Note that an intermediate basin may exist for one type of solvent condition, but not for another. Therefore, the number of template structures used to model a given protein is not some magic fixed number, but rather greatly depends on solvent conditions. It is expected that one template structure will be needed in a classic two-state protein, and only a handful of template structures in bad cases. The implementation of the SCCT puts no limit on the number of template structures that can be used. Some noise and uncertainties may be swept away by using a few template structures, because it is difficult to know what the optimal structural characteristics are in a structure. Ideally, the coarse graining procedure will require only one template structure per free energy minimum basin.

Representing Molecular Structure by a Graph

As in the case of prior computer modeling programs, FIRST and mDCM, a protein or other molecular structure will be represented as a graph. In this context the graph is denoted as, G(V,E), where G labels the graph, V is the set of vertices, and E is the set of edges. A problem with notation is that G is also used for the total Gibbs free energy of a system. Furthermore, V is used for volume and E is used for energy. One must understand these differences by context, and fortunately, the notation of G, V and E related to graph theory will not be used much. The way information is derived from a three dimensional molecular structure, and then how this information is transcribed onto a graph is the subject of modeling, which is discussed below. The graph is then used to represent the structure and interactions between constituents.

The idea of a graph is introduced here because the DCM and SCCT work on a mathematical level that involves properties of a graph. It suffices to note that vertices represent atoms, and/or local groups of atoms that define rigid bodies, while edges represent interactions or more generally some part of an interaction. A given interaction may be represented by multiple edges between a given pair of atoms, and often between multiple pairs of atoms too. Therefore, the graph G(V;E) is a multigraph, which by definition allows multiple edges to form between a pair of vertices. Moreover, when the Pebble Game algorithm and the new Virtual Pebble Game algorithm are discussed, the graph will be directed. However, the calculations that are to be employed to solve the DCM using SCCT will require more properties than just the set of edges and vertices, as discussed below.

Proximity Configuration

Let L define a specific proximity configuration that deals with assigning physical characteristics to all vertices in a graph. The assignment of properties to a vertex only include features of vertices that have close proximity either by chemical distance, or spatial distance. For example, the degree of a vertex (also called multiplicity) is just the number of nearest neighbors the vertex has. On the other hand, local mass density depends on nearby vertices in space, whether these vertices are far or close in terms of the chemical distance along the graph. It should be noted that a short chemical distance always implies spatial proximity. The reason for choosing L for the symbol, is because the properties assigned to a vertex are always localized spatially around the vertex. The concept of proximity can be left loose. It can apply to vertices that model atom locations, residue locations, or even larger structures if the length scales of interest are much greater than the structural unit. In applications of proteins, the proximity configuration will consider atoms and residues as basic units to define localized information. Examples of localized information are: Position coordinates of atoms, number of rotatable dihedral angles in a residue, measure for the degree to which an atom or residue is exposed or buried to solvent, charge on atoms or residues, spectral weight for a given rotamer conformation that would be measured by CD experiments, and the volume occupied by a residue in a given rotamer conformation just to name a few.

The proximity configuration characterizes a coarse-grained description of a template structure, but in general, not the template structure itself. The justification for this is because of a massive reduction of DOF. The solvent DOF are not explicitly accounted for in the DCM. In addition, all the sub-atomic particles such as nucleons and electrons that make up atomic and molecular interactions are not accounted for explicitly. Thus, there are many internal DOF within the molecular structure that are integrated out, which refers to a phase-space integral that has a subset of DOF integrated. In addition, all the DOF associated with solvent are integrated out. When a molecular system is coarse grained (the process that integrates out DOF) the common expression of "potential of mean force" (PMF) is used to describe an effective potential energy function to get the force between particles.

Of course, the PMF has an entropy component, and actually defines a free energy function, not an energy function. Some possible allowed variations in L relative to that obtained by directly using the template structure include solvent molecules invading and perturbing the native structure. Certain residues that are happily buried in the template structure may be assigned to be fully exposed to solvent if we assume solvent molecules solvates this particular residue. Sometimes this may happen, and other times it may not happen. Therefore, L specifies one out of an ensemble of protein-solvent configurations that are accessible to the template structure.

In the DCM, enthalpy and entropy estimations are obtained as functions of the constituent parts of the system. The convention that we will use in the DCM is that the enthalpy and entropy contributions due to solvent effects can be estimated as functions of only the proximity configuration, L. Since we are talking about solvent effects only, we add a subscript to the functions, such that Solvent Enthalpy $H_{solv} = H_{solv}(L)$ and Solvent Entropy $S_{solv} = S_{solv}(L)$.

Additivity of enthalpy and entropy is assumed. Additivity in enthalpy is not a problem, but why should there be additivity in entropy? Additivity of entropy components is assumed because solvent DOF are not explicitly accounted for. As the protein conformation changes, there is a direct effect on the bulk solvent, and the bulk solvent has a counter effect on the protein. Changes in the solvent exposed surface areas (as local measures, and thus changes in L) among many other coarse-grained localized indicators can be used to estimate the DOF within implicit solvent that are effected. These changes are reflected in the increases or decreases in the solvent enthalpy, $H_{solv}$, and solvent entropy $S_{solv}$. Once these components are computed as functions of L the corresponding Gibbs free energy is given as $$G_{solv}(L) = H_{solv}(L) - TS_{solv}(L)$$

At this point, no concept of constraint theory is introduced. All possible outcomes that are represented by L are represented by independent variables that characterize local structural properties, and its relationships with solvent. However, another entropic effect is the conformational entropy, $S_{conf}$, which is a competitive contribution compared to that from solvent. A standard argument is that conformational entropy is the only source of entropy that can overcome the hydrophobic effect at high temperature. If this was not the case, a protein could never unfold (melt) in water. Interestingly, this conformational entropy is related to internal DOF that are modeled explicitly, and therefore, the entropy contributions must be treated with constraint theory.

Constraint Topology

Let F define a specific constraint topology. Because of coarse graining, many constraint topologies will map to the same template structure. Examples of the many to one mapping are easy to spot in terms of intra-molecular H-bonds breaking or forming, and dihedral angles switching from template structure values to disordered dihedral angles, and vice versa. Indirectly, there is a coupling between the proximity configuration, L, and accessible constraint topologies. For example, if a region of the protein is specified by L to be buried, there is very high probability that an intra-molecular H-bond will form. If this same region happens to become exposed to solvent (described by a new L), then there will be a very low probability for the intra-molecular H-bond to be present, in favor of H-bonding to solvent. Therefore, the nature of the constraint topology will depend on the proximity configuration.

In the DCM, enthalpy and entropy estimations are obtained as functions of the constituent parts of the system. The convention that will be used in the DCM is that the enthalpy and entropy contributions due to conformational effects can be estimated as functions of the constraint topology, F. The conformation entropies will depend on network rigidity properties that are calculated from the constraint topology. Hence, the notation of F is used to label constraint topologies as a reminder that they represent mechanical frameworks, from which generic network rigidity (or graph-rigidity) properties are calculated. We then calculate the total enthalpy and entropy contributions that derive from only the constraint topologies as $$H_{conf} = H_{conf}(F) \text{ and } S_{conf} = S_{conf}(F)$$

where the subscript "conf" is used to denote conformation contributions. Compared to the functions given above, we note that $H_{conf}(F)$ is similarly a linear function of F, while $S_{conf}(F)$ is a non-linear function of F governed by the highly non-local properties of network rigidity.

Therefore, the separation between enthalpy contributions derived from solvent properties (controlled by L) and properties of the conformation (controlled by F) is not important because enthalpy is an additive function of constituent parts. It does not matter which compartment (i.e. solvent or conformation) a particular constituent part is assigned to. In contrast, this separation is of utmost importance as far as entropy contributions are concerned. Because solvent properties are related to independent variables in the DCM that ultimately describe the effects of solvent DOF, the entropy contributions are additive.

Because the conformational properties are related to internal DOF, non-additivity effects must be accounted for by regarding network rigidity as an underlying mechanical interaction.

Once the total conformational enthalpy and entropy contribution for the protein is known as a function of F, the corresponding Gibbs free energy is given as:

$$G_{conf}(F) = H_{conf}(F) - TS_{conf}(F).$$

At this point, the enthalpies, entropies and free energies of a given template structure, having a proximity configuration of L and constraint topology of F are all possible to calculate. These different attributes must be combined and used together to calculate the partition function.

There is a built-in hierarchy into the mathematical representation of a protein in the DCM. This hierarchy can be used to develop inheritance properties in data structures that can be defined to make the implementation of SCCT streamlined. For a given protein, there are multiple template structures, 1 protein→many ts. For each template structure there are multiple proximity configurations, 1 ts→many L. For each proximity configuration, there are multiple constraint topologies, 1 L→many F. We label the set of template structures of a given protein by {ts}. Out of all accessible proximity configurations that a protein can take, a subset of them will be associated with ts, which will be denoted as $\{L_{ts}\}$. Out of all possible constraint topologies that the protein can explore, a subset of them is associated with a particular proximity configuration, $\{F_L\}$. The partition function for the entire protein is then given by:

$$Z_{protein} = \sum_{\{ts\}} \sum_{\{L_{ts}\}} \sum_{\{F_L\}} e^{[Ssolv(L_S) + Sconf(F_L)]} e^{-\beta[Hsolv(L_S) + Hconf(F_L)]}$$

where explicit reference to the proximity configuration, $L_S$, and the constraint topology $F_L$ highlights the separation of free energy into solvent and conformation contributions.

The partition function can be subdivided further by introducing order parameters. Let $O_L$ define a multi-component order parameter that involves global properties of the protein involving only characteristics of the proximity configuration. Similarly, let $O_F$ define a multi-component order parameter that involves global properties of the protein involving only characteristics of the constraint topology. Then the entire ensemble of proximity configurations splits up into mutually exclusive sub-ensembles denoted by $\{L_{ts}\}_{OL}$. The entire ensemble of constraint topologies splits up into mutually exclusive sub-ensembles denoted by $\{L\}_{OF}$. Now, because the properties of order parameters are well-defined and independent of template structure, proximity configuration and constraint topology, it follows that the partition function can be expressed in terms of a sum over order parameters, as a grid. In applications, a hyper-dimensional grid is defined by the two multi-component order parameters. Let the number of components (or dimension) of $O_L$ be $D_L$. Likewise, let the number of components (or dimension) of $O_F$ be $D_F$. Then the dimension of the hyper-grid will be $D_{grid} = D_L \times D_F$ where it is possible to have $D_L$ and/or $D_F$ equal to unity. In practical calculations on the computer, it is convenient to discretize allowed values of the order parameters. This means, for component i, of an order parameter, let there be $N_i$ discrete possible values. This discretization corresponds to the process of coarse graining the hyper-dimensional grid into nodes. The total number of nodes is given by:

$$N_{nodes} = \prod_i^{D_L} N_{Li} \prod_j^{D_F} N_{Fj}$$

where $N_{Li}$ is the total number of discretized values of the i-th component of $O_L$. Likewise, $N_{Fj}$ is the total number of discretized values of the j-th component of $O_F$. It is convenient to define a generic node index, called "node" that covers all nodes within the hyper-dimensional order parameter space. Recall than for each node, there will be $N_{ts}$ different template structures. Therefore, we define the depth of a node to be the number of template structures characterized within the node.

In applications, we only need to store in memory non-negligible contributions to $Z_{protein}$. Therefore, it is expected that the depth of a node will not be constant everywhere within the hyper-dimensional order parameter space. Rather, the number of template structures can be a function of the node itself. Within a given node (with order parameters fixed for all template structures), some template structures will have a high statistical weight (favorable), while other template structures will have relatively a very low (unfavorable) statistical weight. Only the template structures with large statistical weight within a node will be kept, and the other template structures will be dropped. The decision as to which template structures are kept and which ones are dropped only depends on relative statistical weights accumulated for each node separately. Since every node represents a different situation, the set of template structures {ts} are now further indexed as {ts$_{node}$} to reflect variations between nodes. The partition function can be written as:

$$Z_{system} = \sum_{node} \sum_{\{ts\}} \sum_{\{L_{ts}\}} \sum_{\{F_L\}} e^{[Ssolv(L_{ts})+Sconf(F_L)]/R} e^{-\beta[Hsolv(L_{ts})+Hconf(F_L)]}$$

The notation that is developed here is generic on purpose, as it applies to all DCMs using any FED. There are basically two classes of constituent subsystems (or parts) within a system. The first class is solvent related, and the other class is constraint related. A FED within the context of the DCM requires the specification of an enthalpy and entropy for each constituent part. An important aspect for computational work is that the FED will be represented as discrete states, which can either be "on" or "off". It is also important to formulate the notation such that a particular part of the system can have internal states. Therefore, for the solvent-class, let the double index (r, s) denote the region of interest, r, and its state, s. For example, r may actually label a residue, and s may indicate whether that residue is buried or exposed to solvent. The exact definition of what r refers to is model dependent, and one can keep the number of possible states low or high. A larger number of states, other than buried or exposed could be 0% exposed, 10% exposed, . . . 90% exposed, and 100% exposed. The nature of the solvent could also be part of the state, such as flexible-solvent or clathrate-solvent. Thus, in general, the number of possible states can be quite large. The smallest number of states that can retain accuracy is computationally the best situation, and this enters into modeling issues. For the constraint-class, let the double index (c, b) denote the specific constraint of interest, c, and its state, b. For example, c may label a torsion-constraint, while b determines whether the torsion constraint is alpha-helical in nature, beta-sheet like, or a disordered coil-like state. Now consider the solvent-class. All elements are assigned an enthalpy, denoted as $w_{r,s}$ and a dimensionless pure entropy parameter, denoted as $\alpha_{r,s}$. The actual entropy is just $R\alpha_{r,s}$, where R is the universal gas constant. The total enthalpy and entropy of the solvent-class is given by:

$$H_{solv} = \sum_R \sum_s w_{r,s} n_{r,s}(L) \text{ and } S_{solv} = \sum_r \sum_s \alpha_{r,s} n_{r,s}(L)$$

where $n_{r,s}(L)$ is a binary occupation indicator for the (r,s)-th constituent part to be present in the system. Specifically, $n_{r,s}=0$ or 1, when the constituent part is not contributing to the free energy or when it is contributing, respectively. Recall that a region cannot be 100% buried and 100% exposed at the same time. So, if for example two states, s1 and s2 are mutually exclusive, then it is implied that when $n_{r,s1}=1$, $n_{r,s2}=0$. Also, if $n_{r,s2}=1$, then $n_{r,s2}=0$. Depending on the model, it may be possible that both $n_{r,s1}=0$ and $n_{r,s2}=0$, or it may be that there is a constraint that $n_{r,s1}+n_{r,s2}=1$. Therefore, there is no loss in generality by using binary indicators. Another important point is the occupation indicator is written as a function of L only. This is mainly because the occupation indicator is part of the proximity configuration specification. It should be noted at this time, however, that the template structure and the constraint topology will generally affect the occupation numbers. As a result, the terms that only depend on L in the equation cannot generally be factored, such that the sum over all constraint topologies can be done first, while holding the proximity configuration fixed, or vice versa. In other words, coupling between L and F is generally allowed and present in the DCM. Although not necessary, a special assumption is employed at the foundation of the DCM about the nature of the coupling between L and F. Specifically, in order to make the solution of the DCM accurate when using mean field approximations, it is best to design a model from the start that has weak coupling between L and F. This is why no terms like $H_{coupling}(L,F)$ and $S_{coupling}(L,F)$ are considered. It is possible to introduce these "cross-terms", but from a mathematical point of view, it is simpler not to have these coupling terms. Rather, this coupling is more subtle, in that it acts through the occupation numbers themselves, which involve local rules, and can be handled easily. For example, if a group of intra-molecular H-bonds locally form, perhaps the region will be harder to be exposed to solvent compared to if no intramolecular H-bonds form.

We can re-express the equation as an inner product between a "bra" and "ket" vector. This idea is borrowed from QM, but it has nothing to do with QM, and possibly the so called vectors that are defined may not actually be vectors in the true sense of mathematics that deals with properties of a vector space. However, by borrowing this QM Dirac bra-ket notation, we can formulate equations based on standard operations, such as an inner product, or at least define operations in the form of operators within standard QM notation. The bra-vector having the hydrophobicity scale is always fixed for a given protein, while the hydrophobic contact ket-vector depends on the specific conformation of the protein. In similar way, I will define bra- and ket-vectors, and their inner products.

Let $<w_{solv}|$ be an assignment of enthalpy values to all solvent-class constituent parts. Similarly, let $<\alpha_{solv}|$ be the corresponding pure entropy assignment. Then let $|n_{solv}>$ define the occupation numbers for all the accessible solvent states. Then, $$H_{solv}=<w_{solv}|n_{solv}(L)> \text{ and } S_{solv}=R<\alpha_{solv}|n_{solv}(L)>$$

A similar series of steps can be done for the conformational part of the FED. Instead of using $w_{r,s}$ for enthalpy components, we use $h_{c,b}$. Instead of using $\alpha_{r,s}$ for pure entropy components we use $\sigma_{c,b}$. Occupation numbers can be defined in a similar way, so that now we use $n_{c,b}(F)$, which obviously depends on the constraint topology, F. Although the enthalpy part of the constraint-class works the same way as it did in the solvent-class, the entropy calculation is radically different. Rather than a sum over all entropy components, the sum is over only independent entropy components. Using the pebble game graph algorithm, the set of constraints can be identified as independent or redundant. The assignment of which constraints are independent or redundant is made in a unique way by sorting the constraints having the lowest entropy values to the highest. By preferential ordering of constraints, a unique set of auxiliary occupation numbers, denoted as $a_{c,b}(F)$ are defined. Here, $a_{c,b}=1$ when the constraint is present and independent, and $a_{c,b}=0$ if the constraint is not present or if the constraint is present and redundant. The total enthalpy and entropy of the constraint-class is given by:

$$H_{conf} = \sum_c \sum_b h_{c,b} n_{c,b}(F) \text{ and } S_{conf} = R \sum_c \sum_b \sigma_{c,b} a_{c,b}(F).$$

We can cast these equations in terms of bra and ket notation by first defining a new ket vector as jaconf i, which packs all the auxiliary occupation numbers, instead of the usual occupation numbers. Then we have $$H_{conf} = <h_{conf}|n_{conf}(F)> \text{ and } S_{conf} = R<\sigma_{conf}|a_{conf}(F)>$$

An interesting point is we can define an operator that transforms the occupation number ket vector into the auxiliary ket vector. This operator is well defined in terms of applying the pebble game with preferential rank ordering of constraints. Let us call this operator $A_{spg}$ because it gives an auxiliary vector (why we use A), and it is based on the sorted pebble game (why we use spg). Then we have $$|a_{conf}(F)> = A_{spg}|n_{conf}(F)>.$$

A useful bra is defined as $<1|$, so that the inner product $<1|n_{conf}> = $ number of constraints within the system. We also have, $<1|a_{conf}> = 3N-6$, which states that the number of independent constraints is always a constant—equal to the number to make the system (with N atoms) rigid. We now have compact notation to express how to calculate total enthalpy and entropy. We will make use of this compact notation in the following sections when we evaluate the partition function under the mean field approximation (MFA). Approximate methods are necessary because the partition function involves an astronomical number of terms to sum. Even after throwing away all zero terms, and all negligible terms from the summation, there remains a huge number of terms (if not astronomical in number) that are non-negligible, and need to be summed. The solution to this problem is to further coarse grain by discretizing the type of interactions that can be present, and to apply mean field theory (MFT), which up to now has not been invoked. As will be seen, approximate methods are employed to make the calculation tractable, but at the same time they need to maintain high accuracy.

MFT Applied to the mDCM without SCCT

In the previously available mDCM, only one template structure is used, selected to be a good model for the native state of the protein. Moreover, only one proximity configuration is used, which is defined by the template structure itself. Another simplification is we do not model $H_{solv}$ nor $S_{solv}$ explicitly. By using some effective fitting parameters, the solvent contributions can be accounted for. However, since these are additive, and because there is only one proximity state, and one template structure, the parameters can be lumped in the conformational part of the calculation. The components for the conformational order parameter are the number of native-like torsion constraints, $N_{nt}$, and the number of intra-molecular cross-linking H-bonds, $N_{hb}$. In other words, $D_F = 2$, and there is no proximity configuration order parameter. This leaves us with a two-dimensional grid to calculate $Z_{node} \rightarrow Z(N_{nt}; N_{hb})$ for all nodes, denoted by $(N_{nt}, N_{hb})$. As a result of these simplifications that have been made to this point, the following equations result:

$$Z_{protein} = \sum_{N_{nt}} \sum_{N_{hb}} Z(N_{nt}, N_{hb})$$

where $$Znode = Z(N_{nt}; N_{hb}) = \sum_{\{F\}(N_{nt},N_{hb})} e^{Sconf(F)} e^{-\beta Hconf(F)}.$$

Note that the sum over all accessible constraint topologies that happen to have $N_{nt}$ number of native-torsion constraints and $N_{hb}$ number of intramolecular cross-linking H-bonds are present in the sum. The mean field approximation (MFA) is now made. It is assumed that for each node, we can replace a sum over exponentials by a single exponential using an average value. In particular, $$\Sigma e^{Sconf(F)} e^{-\beta Hconf(F)} \approx e^{Smix(Nnt,Nhb)} e^{Sconf(Nnt,Nhb)} e^{-\beta conf(Nnt,Nhb)} \{F\}(N_{nt},N_{hb})$$

where $S_{conf}(N_{nt}, N_{hb})$ and $H_{conf}(N_{nt}, N_{hb})$ are averages over the ensemble of accessible constraint topologies. The term $e^{Smix(Nnt,Nhb)}$ gives the number of constraint topologies that are accessible and that have precisely the same macrostate, defined by the node, $(N_{nt}, N_{hb})$. In the implementation of the mDCM, occupation probabilities are defined for a constraint to be present or not. Then, from these occupation probabilities, the average values (i.e. $H_{conf}$ and $S_{conf}$) are determined by Monte Carlo sampling within node $(N_{nt}, N_{hb})$. Since the occupation probabilities are known (to be explained below) many different constraint topologies are generated that have $N_{nt}$ native-torsion constraints and $N_{hb}$ intramolecular H-bonds. The mixing entropy is calculated by the Shannon entropy formula, using the same occupation probabilities.

Notice that MFT is exact when all constraint topologies within a given node have the exact same $S_{conf}$ and $H_{conf}$ and consequently zero fluctuations. In other words, as long as there are no fluctuations, MFT is exact. The way to make the MFA accurate is to choose the best possible order parameter so that within a node, the diversity of different $S_{conf}$ and $H_{conf}$ are minimal. Of course, fluctuations are present in the constraint topologies of the protein.

The Probability Distribution Function

The MFA works directly with the probability distribution function (pdf). Therefore, let us work with the exact pdf within the context of the mDCM first, before making the MFA. Although working within the context of the mDCM simplifies the notation and makes statements less abstract and more concrete, the generality of the formalism continues to be preserved. Let the set of variables $\{n_{c,bc}\}$ define the microstate of the system. Compact notation to represent this microstate using the conformation occupation number state vector is set forth as $|n_{conf}(F)> \rightarrow |\{n_{c,bc}\}>$ which completely defines the constraint topology. From statistical mechanics, the joint pdf involving all occupation numbers is given as:

$$P(n_{1,b1}, n_{2,b2}, \ldots n_{c,bc} \ldots n_{Nc,bNc}) = \frac{e^{\beta G(n1,b1,n2,b2,\ldots nc,bc\ldots nNc,bNc)}}{Z}$$

Where $N_c$ is the maximum number of constraints that can form, and Z is the partition function given by $$Z = \Sigma e^{-\beta G(\{nc,bc\})} = e^{<\sigma conf|Aspg|\{n_{c,bc}\}>} e^{-\beta <hconf|\{n_{c,bc}\}>} \{n_{c,bc}\}$$

This partition function serves as a normalization factor to guarantee $\Sigma_{\{nc,bc\}} P(\{n_{c,bc}\}) = 1$. It is worth mentioning that this equation is exactly the same as noted earlier but in terms of explicit variables for the current implementation of mDCM. Of course, the above equations are exact solutions to the mDCM. Notice that for each microstate, the entropy term involves running the pebble game algorithm using preferential rank sorting of the constraints (i.e. denoted as $A_{spg}$). This entropy can be viewed as related to some intrinsic property of the system, or as in the case of the mDCM, it appears because of coarse graining. In particular, the factor $e^{<\sigma_{conf}|A_{spg}|\{n_{c,bc}\}>}$ represents the geometrical degeneracy describing all allowed conformations for a fixed constraint topology. Proceeding onward; once we have Z we can find the free energy of the system, noting that G=−RT ln Z, which means $$G = \Sigma_{\{n_{c,bc}\}} [<h_{conf}|\{n_{c,bc}\}> - TR<\sigma_{conf}|A_{spg}|\{n_{c,bc}\}> + TR \ln P(\{n_{c,bo}\}) ] P(\{n_{c,bc}\})$$

Where the −plnp terms give the Shannon entropy.

Product Probability Formulation of MFT

In MFT, a product probability distribution function (ppdf) is used to approximate the joint product distribution function.

To discuss this point in more detail, let us simplify the notation a little. Let the microstate of the mDCM be labeled by the index k. Specifically, for each distinct realization of $\{n_{c,bc}\}$ let us index it by "k". For example, if each $\{n_{c,bc}\}$ has two states (i.e., $b_c$ is binary) and there are a total of Nc=1200 constraints (a typical number for a 200 residue protein), then the number of microstates is $2^{1200}$, which means k runs from 1 to $2^{1200}$. This is more than $10^{361}$ microstates to calculate to get the free energy of the protein, even after many drastic simplifications. Let us call the total number of microstates, Q. Then we rewrite the equation as $$G = \sum_{1}^{\Omega} [(E_k - TR\tau_k)p_k - TRp_k \ln p_k]$$

Where $\tau_k$ is the total pure entropy of microstate k, and in the context of the mDCM, $\tau_k = <\sigma_{conf}|A_{spg}|>$. Standard statistical mechanics always has $\tau_k = 0$ for all k. The extra factor of pure entropy naturally appears when we have coarse grained models.

For applications dealing with large systems in the thermodynamic limit, where N→∞, the minimum is all that matters. This is because the system cannot tolerate deviations away from the minimum. If one considers a g that is $g_{min}$+dg, where dg>0, this will cost an infinite amount of thermal energy, since $\Delta G = N_{dg} = \infty$, which is true no matter how small you make dg. In finite systems, one expects to observe thermal fluctuations about the minimum. Therefore, with N finite, it makes sense to talk about the free energy of the system as a function of p.

What does G(p) tell us? G(p) is the free energy as a function of the fraction of spins that are in one specific state (in this case, say along the direction of an external field). The variable p can be used as an order parameter. There are a few more important observations about the MFT solution to the Ising model:

1. The solution does not involve the dimensionality of space, and MFT breaks down in low dimensions.
2. The coupling between spins is short ranged, and this means that one should expect MFT to perform its worst. The lower the space dimensionality, the more noticeable the short range interaction becomes, due to lack of cooperativity by many neighbors.
3. The coupling between spins involves precisely two aligned spins. This causes the interaction term to be proportional to p2. In general, the degree in the probabilities is related to the number of spins involved in the interaction. Or said another way, for a n-body interaction, the expected degree of the occupation probabilities in the MFT term that describe the n-body interaction will be n.

An interesting point about the DCM is that the fundamental elements are the interactions themselves. Indirectly through interactions, one describes the underlying atomic structure. From a pragmatic point of view, a constraint represents a single object, which allows us to consider what would normally be considered a 2-body interaction between a pair of atoms, as a 1-body interaction. This is similar to solving a two body problem in classical mechanics by mapping it into a 1-body problem. The difference in how the system is decomposed in terms of ascribing occupation probabilities to edges instead of vertices within a graph provides mDCM with a huge calculational advantage over standard MFA methods on Ising-models and other commonly employed models. Also note that because of the nature of the log function acting on a long product of numbers, the mixing entropy (or Shannon entropy) term always works out the same in all MFT calculations.

Unfortunately, the conformational entropy term is much more complicated because of the complex nature of network rigidity. For n-body interactions, the number of $p_{c,bc}$ that are multiplied (the degree) is determined by the number of distinct occupation numbers involved.

In summary, the energy interactions in the mDCM are "on-diagonal" 1-body interactions (over the set of edges), which require only one occupation probability, and thus only one degree of $p_{c,bc}$. However, the rigidity calculation is very long-ranged, many-body interaction that typically requires a high degree of products of $p_{c,bc}$. Since, a priori the degree is not known because this dependence depends on the constraint topology, no pre-summations can be made. In essence, we can consider the degree of the network rigidity interaction to be $N_c$, involving all constraints in the graph. Consequently, the product probability density function ("ppdf") does not simplify the conformational entropy term. This lack of simplification is a direct consequence of the long-range many-body nature of network rigidity. This is a good thing, because we can calculate it efficiently. To proceed using MFT to solve the mDCM, we express the free energy equation in terms of average values to obtain:

$$G_{MFT} = H - T(S_{conf} + S_{mix})$$

where $H = \Sigma_c \Sigma_{bc} h_{c,bc} p_{c,bc}$, and $S_{mix} = -R \Sigma_c \Sigma_{bc} P_{c,bc} \ln p_{c,bc}$. $\ln p_{c,bc}$ can be determined straightforwardly, once we know what the $p_{c,bc}$ are. Also, based on these probabilities, we can randomly generate constraint topologies using Monte Carlo sampling. For each realization of a constraint topology defined by a specific set of occupation numbers, $\{n_{c,bc}\}$, the sorted pebble game operator can be applied. Let $k_n$ define the n-th sample for index k, where a sample means the entire constraint topology occupation numbers are known. Thus, the k index has the same meaning as used above, except instead of summing a huge number of possibilities, we sample over a much smaller number of microstates.

Each constraint has a probability to be present, and if present, to be in a specific state. This probability is given by $p_{c,bc}$, and it is independent to all other constraints. Therefore, a random number is generated to decide if a constraint is present or not, and if so, what state it is in. After doing this for all possible constraints, a realization is made, which defines a constraint topology, ready for the pebble game to be played. This entire process of running the pebble game algorithm is repeated N sample times. Typically, N sample=200, and this process has to be done for each node.

In prior published works, the work was simplified by taking advantage that most of the constraints were treated identically. That is, all torsion constraints associated with a priori rotatable dihedral angles are treated exactly the same in the mDCM. Each torsion constraint, can be in either the native or the disordered torsion states (i.e., binary internal states). For the native state, we assigned an energy v, and pure entropy±nat, and for the disordered state, we assigned an energy of 0 (implying v<0) and pure entropy±dis. Doing this makes the mDCM look more like the standard Ising-model, because there is no local dependence on the native and disordered-torsion constraints. All these probabilities for the various rotatable dihedral angle torsions are now the same. Taking advantage of the massive degeneracies built into the mDCM we can combine all native-torsions into one bin, and all disordered torsions into another bin. However, there are still two major distinct types of constraints. Torsions (with two states) and H-bonds, which can be present or not. The H-bonds are very diverse, and all their probabilities must be treated separately depending on local environment.

The complexity of the task is much more difficult now, due to different types of constraints. Even when the constraint types are the same, they will be placed in different local environments. Clearly, we can no longer use the same occupation probability for all interactions, as done in the standard Ising model. Instead, we must deal with a system that is intrinsically inhomogeneous, and calculate the occupation probabilities. Recall that in the Ising model, it involved taking a derivative of a single variable function, and finding the minimum. Now, the free energy function as given above will have as many variables as the number of constraints, $N_c$. This number is obtained by noting that the number of probability variables is equal to $2 \times N_c$ because each constraint type has two states. The normalization condition per constraint, however, reduces the number of variables by $N_c$ (i.e., 1 per constraint). Thus, altogether, there are now $N_c$ distinct occupation probabilities to calculate.

One must figure out a way to calculate the occupation probabilities based on local environments of the constraints. In other words, each constraint must be treated as a special case. However daunting of a task this may seem, the solution to this problem turns out to be remarkably quite simple! The first step is to apply MFT per node.

The properties of all constraint topologies now share two global characteristics, total number of H-bonds, and total number of native-torsion constraints, which are used as order parameters. As mentioned earlier, the order parameters are very useful because they decrease the diversity of constraint topologies that will be realized within a node. Consequently, the sub-ensemble of constraint topologies within a node have the same global macrostate. How does confinement to a particular node help determine $\{p_{c,bc}\}$. First consider the case without confinement to a node. Without confining to a node, the total number of H-bonds and native-torsions can be anything. This means a constraint is either present or not, and when present, it explores all of its accessible internal states. These intrinsic probabilities are assumed to be given by the normal statistical mechanics partition function for each constituent part separately, and independently. At face value, this assumption differs from conventional MFT, because if this were true, the coupling terms would have no effect.

In the mDCM, the torsion constraints do not depend on local environment, but this is an extreme approximation that will be lifted in the extended DCM. Specifically, the characteristics of the torsion constraints will depend on the residue types that the dihedral angle belongs to, and under a certain local solvent environment.

Upon closer look, one can formulate MFT in this way, but it requires introducing a local effective field that involves the coupling term and the average properties of the variables related to the n-body interaction term. Thus, the assumption used here is not very different than used in standard MFT, provided a local field is defined. In the formalism that was introduced using the mDCM, and to be employed in the SCCT applied to the extended DCM, the effective field that is missing comes into play by being confined to a node.

The confinement to a node is equivalent to imposing global constraints to fix the numbers of H-bonds and native-torsion constraints to be that of the specific macro-state, $(N_{nt}, N_{hb})$. This is accomplished by introducing Lagrange multipliers. The Lagrange multipliers serve the same role as the local field does in standard MFT. However, here, we use local variables (energy and entropy parameters) to account for local variations, and global variables (Lagrange multipliers) to enforce global constraints. The mathematics for enforcing global constraints through the use of Lagrange multipliers is a standard technique of statistical mechanics.

The probabilities for a H-bond to be present are then added up and must give the average number of H-bonds in the network. The only unknown is the Lagrange multiplier, hb, and this equation is solved using an iterative method in the mDCM. A similar expression can be written down for the torsion constraints, with nt as the Lagrange multiplier and the indicator function is 1 for native-torsions. The equation looks the same, except because all the torsion constraints are treated equally, the equation can be solved analytically.

There is still one more difference between the standard MFT treatment of the Ising-model and the mDCM. When all is finished in the mDCM, one obtains a mean field free energy value of GMFT $\{N_{nt}; N_{hb}\}$ for every node, which allows calculating the full free energy function of the system. We obtain the free energy landscape (FEL) in terms of order parameters that characterize the macrostate of the protein. Breaking the problem down into nodes allows for calculating a set of free energy values that are consistent with the global constraints. Each node, or macrostate, has some distinct physical characteristic of the protein, and now we can calculate the probability that the protein will have those characteristics. The large number of properties that can be calculated within a node will be postponed to the discussions involving the SCCT.

Before finishing the discussion on the mDCM implementation, there are two important points that need to be clarified, and then the complete free energy function will be defined in full detail. First, the formula applied to H-bonds has only two states in it. When the H-bond is absent, the energy is set to zero, otherwise the energy, denoted as E, is taken to be the value of an empirical potential function. The H-bond energy depends on the distance between the donor and acceptor atoms, as well as the local geometry of some neighboring atoms forming the structure around the donor and acceptor atoms. As a result, the template structure is very important: It defines all the geometrical details needed to calculate the energies for each H-bond, and it also determines the maximum number of H-bonds that can be present. The occupation probability has the same mathematical form as a Fermi-Dirac distribution function, but only due to the coincidence that there are two internal states.

The Free Energy Function

Keeping in mind the intrinsic limitations of the mDCM, related to the systematic errors it makes by using a suboptimal trial ppdf, the remaining terms were defined to be very straightforward. Specifically, for every intra-molecular H-bond that forms in the protein, we put a penalty for a H-bond that cannot form to solvent. The energy associated with a solvent H-bond (shb) was modeled as −uNhb, where Nhb is the total number of H-bonds, and u is an effective H-bond energy to solvent. Note that this interaction is between the protein and solvent, and also note that u<0 makes sense physically. Adding this term in this way was done for computational convenience more than anything else. Nevertheless, the energetic competition is real, and it should be part of any realistic model for protein stability. The approximation we make in the mDCM, is that the location of the H-bond has no bearing on the value of u. In a more realistic model, the value of u should either depend on H-bond location, and/or the same value of u can be used, but it should only apply to the H-bond sites that are exposed to solvent. None of these details are considered, and this is a direct consequence of simplifying the solvent dependence part of the problem by completely ignoring the proximity configuration from the start.

The equation described above looks like a traditional FED, but clearly the conformational entropy part is very different, due to the long-range nature of network rigidity, and only the independent entropy components contribute.

The extended DCM (not the mDCM) that will take into account many more interactions, including the proximity configuration, will be solved using SCCT so that all the complications mentioned above will need to be solved head on. The next few sections explains how to solve a DCM using SCCT, and as a bonus, we will be able to make second order corrections involving strain energy and reduction of conformational entropy in over-constrained regions.

Overview of SCCT Applied to the DCM

When solving the DCM using a MFA without SCCT, the bad consequence most troubling is that the answers are not self-consistent. This means that there will be problems with parameters not matching up in relation to probabilities for various internal states in the problem.

This problem can be overcome on a case by case basis, by allowing free phenomenological parameters to be adjusted in order to fit to experimental data. An important property for a physical model that relies on some empirical parameterizations is that the parameters of the model are transferable between different systems. In the context of this project, different systems means different proteins placed in different solvents, under different thermodynamic environments. To keep parameters that characterize solvent effects transferable, they should be functions of solvent properties, which would be difficult to work out. However, if we can define a small subset of parameters that depend on solvent properties, and then let them be freely adjustable to account for solvent effects, then we can obtain a model with mostly transferable parameters.

Even though the goal of attaining transferable parameters in the DCM may not be fully achieved, we can be certain about one thing: If we obtain inconsistent results for a single calculation for a protein within a given solvent, then we cannot expect consistency across multiple proteins for the same solvent, or the same protein for different solvents, much less any protein for any solvent, which is the goal. Clearly, a detailed DCM is necessary, and we must solve it self-consistently to make accurate predictions in practical applications.

Interactions, Constraints and Bars

Here some terminology is defined that will become standard language for the DCM. As shown in FIG. 1 a hierarchical tree with corresponding nomenclature is developed. We begin at the root of the tree, which is the collection of all types of interactions. These types of interactions need to be defined in what is called a free energy decomposition (FED). The details of a FED are discussed in a separate section below. Here, it suffices to know that there are many interactions associated with one protein (or other molecular system).

Some of these interactions involve internal DOF within the molecule, and therefore affect conformational motions. For selected interactions involving internal DOF, we model them either as one constraint or multiple constraints. If one constraint is involved, it will connect between a pair of vertices within the graph that represents the constraint topology. If more than one constraint is involved, the set of constraints may connect the same pair of vertices, or could connect a variety of different pairs of vertices.

Each constraint is then modeled as one or more bars. A bar is what the old FIRST algorithm would call a distance constraint. As an example, the H-bond interaction can be modeled as four constraints, and each of these constraints might be modeled as 2 bars. If this is the case, one H-bond would have 8 bars associated with it. As another example, we could have a residue with 5 torsion DOF. Many-body effects of the rotamer states of the residue. So this interaction would be modeled using five constraints, if each torsion constraint is modeled as 10 bars, then the rotamer interaction would consist of 50 bars. We use i to label the interaction, c to label the specific constraint member, and b labels the bars within a constraint. Each bar must be assigned an enthalpy and entropy parameter. Each bar represents the internal state, and it also defines the distance constraints that define the constraint topology forming the mechanical framework.

Product Probability Distribution Function

For the moment, consider working with the mDCM but using SCCT instead of the MFA that is currently implemented. What would the difference be? To begin with, each interaction type in the system is identified, and all of their corresponding constraints placed with the appropriate number of bars, which taken together form a constraint topology. Other than another layer of labeling, so far nothing is different. The independent probability of interest is given by:

$$p_{i,c,b} = \frac{e^{\sigma'_{i,c,b}} e^{-\beta h_{i,c,b}} e^{\beta \mu v_{i,c,b}}}{\sum_{c'} \sum_{b'} e^{\sigma'_{i,c',b'}} e^{-\beta h_{i,c',b'}} e^{\beta \mu v_{i,c',b'}}}$$

Where $\sigma'$ is the pure entropy for bar b within constraint c representing i; $\mu$ is a Lagrange multiplier, and the indicator function $v_{i,c,b}$ is the same function as introduced previously. The rank ordering is always based on the assigned value of the pure entropy, $\sigma'_{i,c,b}$ is redundant. The entropy value should simply be $\sigma_{i,c,b}$ and is called the are pure entropy. The actual pure entropy will be equal to the bare pure entropy only when the constraint is independent.

Now the main question is what is the pure entropy value? The pure entropy should be 0 when the bar associated with $\sigma_{i,c,b}$ is redundant. The entropy value should simply be $\sigma_{i,c,b}$ when the bar is independent. In fact, the pure entropy value should be something between $(0 \leq \sigma'_{i,c,b} \leq \sigma_{i,c,b})$ depending on the state of the bar in question. Therefore, we define the pure entropy value to be:

$$\sigma'_{i,c,b} = q(i,c,b) \sigma_{i,c,b}$$

where q(i,c,b) is a conditional probability that the bar in question is independent. The q value can be thought of as a simple ratio, but the reason why we think of it as a probability is because one could imagine running the pebble game, say many more times than $10^{350}$, to calculate the fraction of time the bar is redundant or independent. This statistical calculation would define q as the number of times the bar worked out to be independent out of all trials. Then, the proposed model uses a self-consistent pure entropy value of $\sigma^t_{i,c,b}$ albeit a mean field value (i.e. an average).

Universality and Transferability

A free energy decomposition scheme is defined in terms of a set of interaction types, and the properties of each interaction type within this set. The traditional concept of a free energy decomposition is that the interactions can be partitioned so that each will contribute orthogonal information, and therefore, the total free energy of the system is a linear sum of all the components within a system. This approach breaks down when the interaction types are not orthogonal to one another for all pair-wise comparisons. For such an approach to work, the interaction classification should be very specific to a particular system, and because this division is not generic, the decomposition will fail for all physical systems, except the one it was constructed to work for. The diversity found in accessible conformations of bio-macro-molecules, such as proteins, already makes linear free energy decomposition schemes break down, as there is no single decomposition that works well for all possible conformational states.

There is no presumption of orthogonality in the DCM. Nevertheless, it is assumed possible to break down any physical system into a complete universal set of interactions that will describe all physical and chemical properties of that system. For simplicity, we consider the much more restricted case of all possible molecules placed within all possible solvents, under all possible thermodynamic conditions. Every possible physical effect that is not negligible in all possible cases must be accounted for either by one interaction type, or it may be accounted for multiple times by being included in many different interaction types. Consequently, one interaction type will generally account for more than one physical effect simultaneously. Therefore, it is possible to have a complete set of interaction types, but these interactions are not orthogonal to one another.

Once it is realized that more than one interaction type will be associated with a particular physical effect, then it is possible to define many more interaction types than the minimum number actually needed to cover all the distinct physical effects. For example, within the standard model of modern physics, only four distinct forces are believed to exist in nature, and all physical systems can be decomposed in terms of these fundamental elements. These four forces constitute the minimum number of interaction types to form a complete set that can describe any physical system. On the other hand, consider C-bonds, H-bonds, long-range electrostatics and packing interactions, among a long list of other interaction types. All of these distinct interaction types are associated with electrostatic forces, but they each involve much more complexity than just electrostatics. As this last example illustrates, we will be interested in defining interaction types that generally include the concept of course graining in the sense that observed repetitious patterns found in nature will be used as building blocks. Thus, in general, there will be many more interaction types defined for which they share a particular physical effect.

The properties of each interaction type within a DCM includes assignment of an enthalpy contribution, nominal entropy contribution, specification of how many constraints used to model the interaction, as well as associated measurable physical and chemical properties. When constructing a free energy decomposition scheme for the DCM, the following considerations should be taken into account.

1. Complete FED A complete set of interaction types should be defined so that all physical systems of interest can be described by the same scheme. In this work, complete means that all proteins under a restricted range of solvent and thermodynamic conditions can be described. The restrictions can be lifted at will at the expense of additional model complications. However, reasonable restrictions include a limited pressure and temperature range, and a range over solute concentrations. In this work, the complete set of interactions will cover two extreme solvent environments, which will allow us to fully account for aqueous and membrane bound proteins within the same FED, and thereby treat them on equal footing from the start.

2. Non-unique FED. There is not a unique free energy decomposition scheme. The Tao of the DCM is that there are an infinite many different ways to break a complex system into subparts, and sub-subparts, and so-forth, yet in all cases, the DCM methodology provides a universal way of combining all these pieces back together to predict the total free energy.

3. Greedy FED. In applications, it is expected that some undefined chemical group will be encountered. When these encounters happen, parameters will not be available for the new chemical group, despite a complete set of interaction types defined. Therefore, additional parameters must be found for every new type of chemical group encountered. When this happens, all previously determined parameters for known chemical groups and their associated interaction types will not change. It is possible that new parameters that depend on interactions with the new group with prior groups will have to be defined and determined. This add-on process is referred to as a Greedy FED.

4. Transferable DCM. The interaction types will be modeled mathematically in the same way using equations that are assumed to have an invariant form under all allowed conditions. However, the parameters of the equations may depend on solvent and or thermodynamic conditions. For the same solvent and thermodynamic condition, all parameters should be transferable. The complexity of the equations will depend on how restricted the range of applicability we demand. Thus, transferable is only a property that is within the range of validity of the model.

5. Non-Transferable DCM Parameters The DCM does not model bulk solvent explicitly. It therefore has built into it effective parameters that are intended to account for how different physical and chemical characteristics of the bulk solvent properties affect the system (i.e. protein). In principle, these effective parameters should be derived from careful ab initio theory. In practice these parameters can be determined from systematic experiments, as fitting parameters. The non-transferability of model parameters is only limited to applying the DCM in a new solvent and/or thermodynamic condition that has not been done before. Once the parameters are established for that specific condition, they are transferable across all proteins.

6. Error Parameters. The DCM will also contain error parameters to account for imperfections within the model. It can be expected that stability predictions for a large number of diverse proteins under identical solvent and thermodynamic conditions will not be 100% accurate, 100% of the time! To eliminate errors, these parameters will be adjusted to reduce dramatic amount of errors whenever needed on a case by case basis. The default values of all estimation parameters will be zero. The goal is to make the final DCM (after many years of incremental improvements) have as few as possible error parameters, and those that remain, are small tweaks away from their default zero values. If not every possible physical effect is perfectly accounted for 100% of the time, then one really should expect some error correction.

The above list highlighted all the essential model properties that are being sought after in this project. The current minimal DCM is a model that has some of the properties mentioned above, including the so called error correction parameters. One reason why the model can fit to many different heat capacity curves with the mDCM is because of built in error correction, which include baseline parameters in order to fit the DSC experimental data. The objective here is to explicitly model interactions to do away with as much of these error parameters as possible. We do not want to use error correction to make the model robust. Monitoring error correction parameters provides insight into identifying certain effects that are initially missed, and thus, over time, the number of required error parameters will be reduced.

Relationship Between Degrees of Freedom and Constraints

Degrees of freedom (DOF) are variables to describe the configuration of a system. The variables may be restricted to a finite range, but in any case a DOF represents a continuous variable. A constraint is a realization of a DOF, such that the DOF is no longer free, but has a precise value dictated by the constraint. For example, consider two volumes, V1 and V2, where each volume is considered a DOF. Also consider a constraint, where $V1+V2=V_{total}$ where $V_{total}$ is a fixed number. In this case, if V1 is specified, then V2 is known. As a result, the constraint forces a particular realization on V2 when V1 is specified, or vice versa. Although a priori both V1 and V2 are DOF, only one of them is an independent DOF.

In the DCM, the concept of a DOF and constraint is at a coarse grained level. Consequently, a constraint means much less and much more in the DCM than usual. First, consider why a constraint means much less than usual. A constraint realizes a DOF to be a particular value, but it does not specify the value. For instance, suppose $V_{total}$ in the above example is known to be fixed, but the specific value for $V_{total}$ is not known. Algebraically, the relationships between number of DOF, how many are independent, and the nature of the constraint is the same regardless what the actual number of $V_{total}$ is. In the DCM, the network rigidity properties are generic and the actual values are not of importance, but rather the relationships dealing with network rigidity are important (i.e. independent constraints or DOF, what is rigid or flexible, etc). The generic network rigidity properties are invariant under a large sample space of specific assigned values. The constraint in the DCM is representing a family of realized constraints all having specific specified values. Given that a family of realizations of a DOF is built into the meaning of a constraint in the context of the DCM, some people have suggested that the phrase restraint is more appropriate to use than constraint. This cannot be implemented, however, because the notion of a constraint is opposite to that of a restraint. A restraint never allows the variables to be realized at a fixed value, and therefore a restraint always represents a DOF. A restraint is in a practical sense, limiting the range of observed values of a DOF. Usually, restraints are modeled as springs.

A spring has a potential energy function that goes as $\frac{1}{2}kx^2$, and we call the variable x a quadratic DOF. This typical restraint type is no constraint whatsoever! More generally, we can consider any function U(x), and we say x is a DOF as it is not specified. Constraints specify the values of x, but in the DCM the value x=xo is declared to be assigned, but the value is not specified. In this sense, a constraint means less than usual. The notion of a constraint in the DCM also means more than usual. Because the constraint in the mechanical sense means that a specific value will be realized for a given DOF, the DCM also tags along with the constraint a typical value of U(xo) after the x DOF is specified to be xo. The typical number of different x-values having a similar U(xo) values to within a predefined energy tolerance is also specified in the form of a nominal entropy. Thus, the family of possible realizations is quantified by a coarse graining procedure in terms of the enthalpy and nominal entropy parameters of the DCM. Other physical properties besides energy can be tagged to a specified value x=xo, such as local volume, polarization, magnetization, local heat capacity, etc. Thus, the DCM operates on a coarse grained scale, using constraints, not restraints.

Once the above logic is appreciated, the number of constraints that one should model a particular interaction type needs to be answered. The answer is to use the same number of constraints to model a given interaction as it takes DOF to specify the energy function. This is the relationship between constraint and DOF. In practical calculations, we wish to describe the free energy of a protein in terms of its global flexibility, which is related to the number of independent constraints having the greatest entropy values. Only the independent disordered torsion constraint type will be considered to contribute to the overall flexibility, and used as a direct measure of global flexibility. The justification for selecting the independent disordered torsion constraints as a measure of flexibility is that this constraint allows wildly different realized values of a particular angular DOF. In other words, at the coarse grained level, the constraint is unable to confine structure in any appreciable way.

Hierarchical Approach

Different constraint types will be defined, assuming other constraint types have been previously defined. Normally, it makes sense to define the constraints with the lowest nominal entropies first, and work from the strongest to the weakest constraints. Not all the entropy contributions are from conformational entropy, and therefore there may be large contributions that are additive in nature. The hierarchical approach will be invoked in places where it makes sense to define a certain constraint type in terms of other constraint types previously defined. The most important consequence about a hierarchical approach is:

1. Use the DCM at all levels of the modeling, so all parts are consistent with the ideas of non-additivity of entropy.
2. Local environment can be assumed known when constructing properties of constraint types. The actual environment can be determined on the fly during calculations, and the properties of the constraint types can depend on the specific local properties.

Parameterization for a Generic Molecule in Solvent

The generic form of a partition function for a molecule in solvent will be the same for all types of molecules. The formula is given by $$Zgeneric = \sum_{i}^{n} Z_{sol}(i) Z_{ms}(i)$$

where $Z_{ms}(i)$ represents a particular i-th macrostate of the molecule. The macro-state characterizes some solvent-molecule interactions that are described by $Z_{sol}(i)$, which is common with all the molecular conformations that are part of the macro-state sub-ensemble. Consider the example of a protein. A protein has many different conformations. These are grouped into macro-states. For each of these macro-states, the characteristics of the molecular conformations dictate how the molecule will interact with solvent, which includes surface effects, volume effects and electrostatics. All these complicated interactions are described by $Z_{sol}(i)$, which also accounts for the characteristics of the solvent itself. For example, as a crude approximation for describing a protein, suppose we use a two-state model, where there are only the folded and unfolded macrostates.

Then because the nature of how the various amino acids in the protein are exposed different, one expects the unfolded state to interact with solvent differently than the folded state. In the DCM, different macro-states of a protein are defined in terms of the free energy landscape in constraint space. Therefore, for a protein, the number of macrostates, n, will be large. The number of macrostates, n, should be selected to be as small as possible, but needs to be big enough to provide a good representative of the diversity found in conformational states of a molecule. For the i-th macrostate, the solvent effects are described by $$Z_{sol}(i) = e^{\alpha_i} e^{-\beta w_i}$$

where $w_F$ is a pure entropy parameter and $w_i$ is an enthalpy contribution related to the total solvent-molecule interaction. These two parameters may be functions of constituent parts of the molecule. In the case of a protein, the two parameters $\{\alpha_i, w_i\}$ will be calculated for each macrostate, i, in terms of a free energy decomposition. It is assumed that all entropy parameters involving solvent interactions are additive. The non-additive effects dealing with conformational entropy is intentionally contained within the Zce(i) partition function. Although the solvent free energy decomposition is assumed additive, various component contributions will be coupled to non-additive parts of conformational entropy. For example, intramolecular H-bonds affect conformational entropy and are related to the degree various residues are buried or exposed to aqueous solution. Thus, additive solvent entropies are tied to non-additive entropies through complicated non-trivial relationships, which will be calculated for proteins using SCCT.

Constraint Theory

Molecular structure is represented as a body-bar network, where covalent bonding between atoms is used to uniquely identify an initial collection of labeled rigid bodies [17]. A covalent bond between two atoms is represented as an edge between the corresponding two vertices in the body-bar network. Only three types of vertices can occur in terms of incident edges:

1) A vertex is isolated when it has no nearest neighbor (no incident edges);
2) it is a dangling end if it has a single nearest neighbor; or
3) it is multi-connected if it has two or more nearest neighbors.

Figure 2:
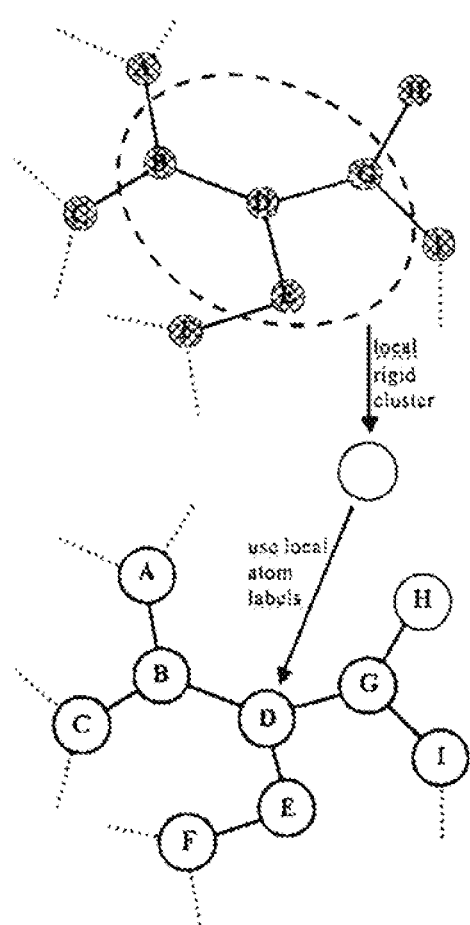
FIG. 2: An example section of a mapping from atomic structure (top) to a body-bar network (bottom).

Each non-isolated atom of the molecular structure is grouped into a rigid cluster consisting of it and its nearest neighbors and represented by a vertex in the network. An example mapping from atomic molecular structure to a body-bar graph is shown in FIG. 2. The vertices that represent rigid bodies are labeled identically as the atoms in the molecular structure are labeled because there is a 1 to 1 mapping between an atom and a rigid body vertex.

FIG. 2 further shows an example section of a mapping from atomic structure (top) to a body-bar network (bottom). The labeled hashed small circles represent atoms, and the solid lines represent covalent bonds. Dashed lines indicate that the network continues. The cluster of four atoms {B,D,E,G} within the dashed-ellipse shown in the atomic structure defines a rigid body as indicated by a large open circle. The distinct atom-label for the topological center atom within a rigid cluster of atoms is used to label its corresponding rigid body. After this mapping, the body-bar network looks identical to the original atom structure.

In the preferred embodiment, isolated vertices are assigned 3 DOF, and all other vertices are assigned 6 DOF. A bar, b, represents a distance constraint between two vertices, and it removes one DOF from the network if placed within a flexible region. The b-th bar is described by a discrete random variable, $n_b$, that equals 1 when the bar is present in the network, and 0 when it is not present. The b-th bar is present in the network with probability $p_b$, and not present with probability $(1-p_b)$, and these two possible events are independent of whether any other bar in the network is present or not. A statistical ensemble of body-bar networks is defined based on the product probability measure for the entire network given as:

$$\text{PROB(network)} = \Pi_b (p_b)^{n_b} (1-p_b)^{(1-n_b)} \qquad \text{Eq. (1)}$$

for $2^{nb}$ distinct body-bar networks. For any member of this ensemble of realized body-bar networks, a bar can either reduce the number of DOF by one if it is independent or not change the number of DOF of the network if it is redundant. When the b-th bar is present in a network, let $Q_b(\text{network})=1$ or 0 when it is found to be independent or redundant respectively. The pebble game algorithm [16,17] with a pre-sorted bar placement ordering can be employed to identify whether a bar is independent or redundant. Given that the b-th bar is present in the network, the conditional probability for this bar to be independent is given by $q_b = \{Q_b(\text{network with b-th bar present})\}$ where the average is over all body-bar networks that contain the b-th bar using the probability measure of Eq.(1) divided by $p_b$. Although this is an exact way to calculate all conditional probabilities, $\{q_b\}$, often there will be well over $n_b=10,000$ bars that fluctuate in typical applications. Unfortunately, even for an atypical tiny system with $n_b=50$, running the pebble game $2^{50}$ (i.e. $\approx 10^{15}$) times is prohibitive for high throughput applications.

Figure 3:
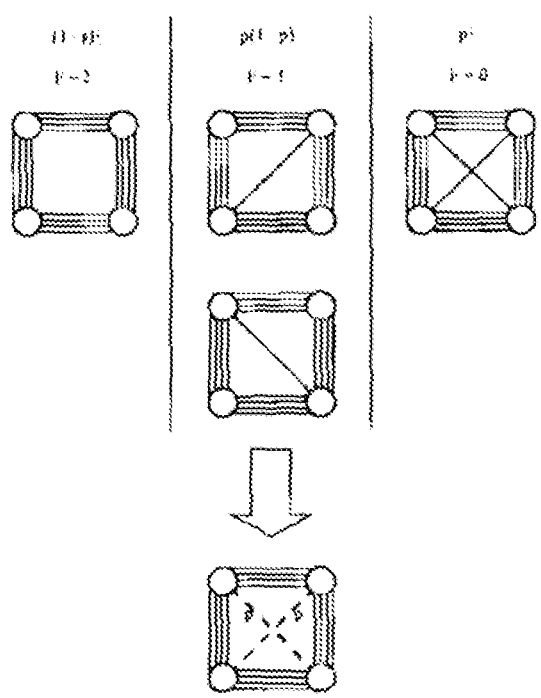
FIG. 3: An example quadrilateral body-bar network, where 4 quenched bars connect a pair of vertices on each side, and a fluctuating bar along each diagonal with probability p to be present.

FIG. 3 shows an example quadrilateral body-bar network, where 4 quenched bars connect a pair of vertices on each side, and a fluctuating bar along each diagonal with probability p to be present. The 22 possible body-bar networks define an ensemble, which are grouped in terms of the number of fluctuating bars present (i.e. n=0,1 or 2). The number of internal DOF, F, is given as F=24−4×4−n, since there are 4 rigid bodies each with 6 DOF, 4 bars on 4 different sides, and n fluctuating bars depending on the state. The entire ensemble is represented by a single effective body-bar network, where the fluctuating bars are shown as dashed lines, and each are assigned a capacity equal to their probability of being present.

Figure 4:
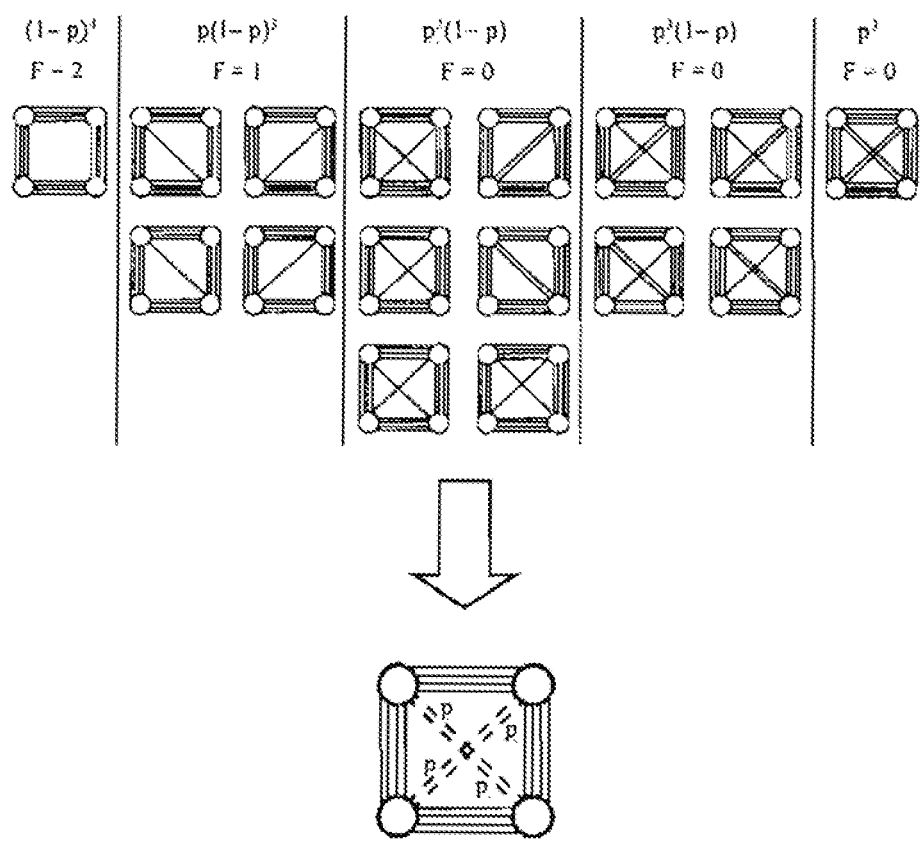
FIG. 4: An example quadrilateral body-bar network, where 4 quenched bars connect a pair of vertices on each side, and two fluctuating bars along each diagonal.

FIG. 4 is an example quadrilateral body-bar network, where 4 quenched bars connect a pair of vertices on each side, and two fluctuating bars along each diagonal. Each fluctuating bar has probability p to be present. The 24 possible body-bar networks define an ensemble, which are grouped in terms of the number of fluctuating bars present (i.e. n=0, 1, 2, 3 or 4). Since n=3 or 4 results in one or two redundant constraints, the internal DOF, F, is given as F=max(24−4×4−n, 0). The entire ensemble is represented by a single effective body-bar network, where the fluctuating bars are shown as dashed lines, and each are assigned a capacity equal to their probability of being present.

In this invention, an ensemble of body-bar networks with statistical measure of Eq.(1) is represented as a single effective body-bar network. All bars are present in the effective body-bar network, but each bar has a capacity. The capacity of the b-th bar is set to $p_b$ to represent the maximum number of degrees of freedom the b-th bar can remove from the network. Since $0 \le p_b \le 1$, the effective body-bar network allows for fractional degrees of freedom. FIG. 3 shows an example of how an ensemble of networks based on two fluctuating bars, each having an occupation probability, p, is represented as a single effective body-bar network. FIG. 4 shows an example of an effective body-bar network representing an ensemble of 16 body-bar networks based on 4 fluctuating bars, each having a probability of p to be present.

The utility of the effective body-bar network is to provide an estimate for average rigidity properties over an ensemble of body-bar networks that include the set of conditional probabilities, $\{q_b\}$, and identification of over-constrained regions. An effective body-bar network facilitates different mean field approximations for constraint counting. The simplest MFA is Maxwell Constraint Counting (MCC) that deals with the average number of bars globally within a network, given by $\{N_b\} = \Sigma_b p_b$ such that the number of internal DOF is estimated as $F = \max(NDOF - 6 - \{N_b\}, 0)$ where NDOF is the number of DOF of all vertices in the network when no bars are present. To account for local variation in density of bars throughout the network, the exact pebble game algorithm is generalized to a Virtual Pebble Game (VPG) that is directly applied on the effective body-bar network. The essential idea is to subtract a maximum of $p_b$ DOF per bar, instead of 1.

Figure 5:
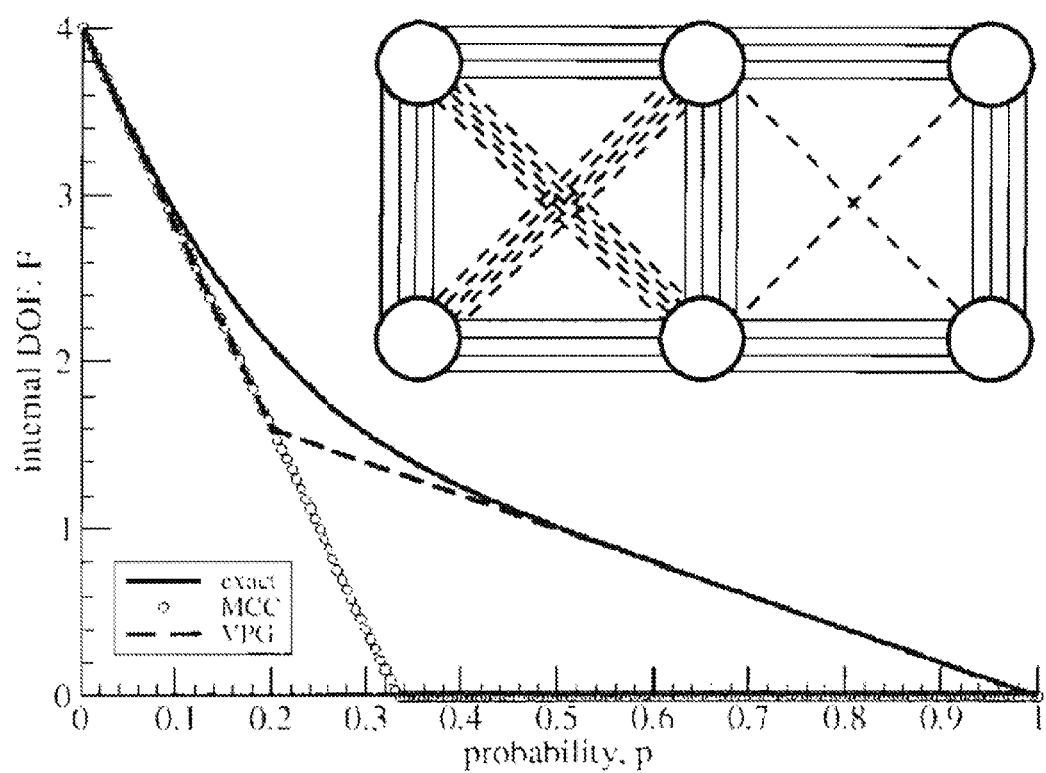
FIG. 5: An example of two edge-sharing quadrilaterals, where each side of either quadrilateral has four quenched bars.

FIG. 5 is an example of two edge-sharing quadrilaterals, where each side of either quadrilateral has four quenched bars. The quadrilateral on the left has a high density of fluctuating bars, being 5 per diagonal, while the quadrilateral on the right has a low density of fluctuating bars, being 1 per diagonal. In the exact method, there are 212 possible body-bar networks in the ensemble. In the graph of FIG. 5, the exact average F over all 212 possible networks is given by the solid line; MCC is given by the open circles; and the broken dashed line gives the VPG result. Notice that the VPG essentially gives the MCC result within local regions, and therefore is an excellent approximation on either extreme of low or high density of constraints. Both MCC and the VPG approximations work best as the density of constraints is more uniform, for which this example is not.

Implementation details of MCC and the VPG in relation to the FER are described below, following an illustration of how constraint theory is applied to a simple network. Shown in FIG. 5, the exact pebble game average, MCC and the VPG results are compared based on a network involving 12 fluctuating bars, with high variance in bar density. For simplicity, all fluctuating bars are assigned the same occupation probability, p, and the formulas for number of internal DOF, F, as a function of p for the exact average, MCC and the VPG are given as:

$$F = 2(1-p) + 2(1+9p)(1-p)^9 \text{ Exact pebble game average}$$

$$F = \max(4-12p, 0) \text{ Maxwell Constraint Counting}$$

$$F = 4 - 2p - \min(10p, 2) \text{ Virtual Pebble Game} \quad \text{Eq. (2)}$$

Although an effective body-bar network was originally introduced to assist mean field approximations, it now is a critical component to the computer-implemented system. The effective body-bar network serves to define a framework for a novel type of DCM that enables new methods within the FER part of this invention as selectable embodiments.

Free Energy Decomposition (FED)

The computer-implemented system and method is based on a FED that accounts for enthalpy and entropy contributions from solvent, conformation and vibration. The explicit solute specification provides one or more template structure. Given a template structure, user-defined rules are employed to classify various contiguous groups of atoms that appear within the molecular structure into cooperative units that are parameterized. The parameters will generally depend on solvent and thermodynamic conditions, which are given in the implicit solvent specification. A canonical FER is implemented to combine free energy components to predict the total free energy. As such, the FER places certain requirements on the nature of a FED. To ensure universal and portable FED characteristics, a list of guiding principles is given to define a paradigm suitable for a general DCM solver and FAST calculator.

Guiding Principles:

A FED is not unique because a complex system can be broken into subparts in many different ways. The preferred embodiment provides users flexibility to define different kind of classification rules and different parameterizations.

A FED must be complete in terms of a finite set of interaction types for the scope of applications of interest. For example, a FED may account for any system of proteins in aqueous or non-polar solvents at different temperatures and pressures, but inadequate for ionic-liquids or when a non-amino acid is present. Unknown solvent conditions and chemical groups will be reported to users, and thus, FED completeness is checked upon initializing the calculation.

A FED should be expandable by a greedy approach. Undefined chemical groups will be encountered on occasion; indicating the finite set of interaction types is incomplete. Without changing any known interaction type properties, augmenting missing constituent classifications and associated parameters restores the FED to being complete. This corresponds to a bottom up building-block approach that treats local properties of the building blocks as self-determining. New parameters that describe solvent interactions can be augmented into look up tables empirically based on an on-need basis.

Parameter transferability should be exhibited in a FED for different explicit solute specifications with fixed implicit solvent specification and thermodynamic condition. In addition, parameters that depend on solvent and thermodynamic conditions should exhibit universal functional dependence that can either be modeled or determined empirically.

A FED should permit non-transferable parameters because solvent interactions are modeled implicitly. Effective parameters are used to account for different physical and chemical characteristics of bulk solvent properties and how they affect the explicit solute. It may not be possible to derive functional dependence from first principles or from systematic experiments. The parameters that are sensitive to changing solvent and/or thermodynamic conditions can be treated as fitting parameters.

Constituent Classification Rules:

A user should invoke common knowledge in the art of computational chemistry to develop specific rules that identify group of atoms of chemical importance, such as amino acids for proteins, or those atoms that participate in some type of chemical bond, or through non-bonding van der Waals or electrostatic interactions. The classification rules involve the types and coordinates of atoms specified in a template structure, capable to assign an atom to more than one group of atoms. For example, it could happen that a particular oxygen atom belongs to a covalent bond, a residue, two hydrogen bonds and several van der Waals interactions with other atoms from other residues. Therefore, it is clear that one atom will generally belong to multiple groups of atoms. Suppose another oxygen atom is bound to a protein, but is not associated with an amino acid. The oxygen atom could be treated as its own group (a group of one atom only) plus it too participates in various inter-atomic interactions. Although multiple atom groupings will be classified and used in the FED, the term molecular constituent is reserved to specify a special type of group of atoms.

The two oxygen examples above illustrate what is commonly encountered in the art of computational chemistry, since there are many ways to group atoms. Although a single atom may belong to multiple groups of atoms that define various types of inter-atomic interactions, each atom must be assigned to one and only molecular constituent that will act as a cooperative unit. In the first example, the oxygen atom belongs to a specific type of residue that defines a particular type of molecular constituent. In the second example, the oxygen atom itself defines another type of molecular constituent, although it is not a molecule. In this invention, solvent interactions are expressed in terms of molecular constituents interacting with solvent molecules. Although a FED is by its nature amorphous in details, as it pertains to this invention, a FED will possess a canonical universal form required by the FER. The universal form interprets a user-defined FED and its classification scheme into elements that relate to solvent-interactions and intra-molecular interactions.

Solvent Interactions:

A discrete variable, s, defines a local solvent environment for molecular constituents. For the r-th molecular constituent, the variable, s, classifies its local solvent environment into Sr discrete states. In many applications, the label, r, denotes a residue. In general, $S_r$ may vary for different types of molecular constituents. For each discrete state deemed important to include in the FED, the enthalpy $h_{slv}(s|r)$ and entropy $R\alpha_{slv}(s|r)$ must be specified in tables. Note that $\alpha_{slv}$ is a dimensionless pure entropy, whereas R, is the universal ideal gas constant. As an illustrative example based on a working prototype, consider Sr=3 for all r. Let $s_r$ define three possible local solvent environments for the r-th molecular constituent given as:

$s_r$=c, indicating a solvent exposed clathrate environment, where solvent controls conformation.

$s_r$=m, indicating a solvent exposed mobile environment, where conformation controls solvent.

$s_r$=b, indicating a buried environment, representing a generic non-polar solvent.

All other solvent interactions are expressed as functions of $\{s_r\}$ over the template structure. Let the Kronecker delta function be defined as $\Delta(m,n)=0$ if m≠n, and $\Delta(m,n)=1$ if m=n for integers, m and n. Then $\Delta(s_r,c)=0$ if $s_r$≠c, and $\Delta(s_r,c)=1$ if $s_r$=c. Likewise, $\Delta(s_r,m)=0$ if $s_r$≠m, and $\Delta(s_r,m)=1$ if $s_r$=m, and finally $\Delta(s_r,b)=0$ if $s_r$≠b, and $\Delta(s_r,b)=1$ if $s_r$=b.

Hydrophobic Interaction:

The free energy to transfer a water molecule from a generic non-polar environment to bulk solvent is given by $G_{hph}=(h_{hph}-TR\alpha_{hph})\Delta(s_x,b)\Delta(s_y,b)$, for all x,y pairs in proximity within the template structure. Note that x and y represent specific molecular constituents within the template structure. The general idea is that a molecular constituent pair (x,y) is within proximity if the atoms making up the pair are too close to allow a water molecular to squeeze in between. The user-defined rule for what constitutes proximity determines the maximum number of hydrophobic interactions that can simultaneously occur for a given template structure. A simple rule that can be implemented is that proximity occurs when two molecular constituents form a nearest neighbor contact with one another.

Nearest Neighbor Molecular Constituent Contacts:

In the art of Computational Biology, it is common practice to define residue-residue contact maps. Different criteria can be employed to identify a contact between two residues. For proteins, a frequently used criterion for two residues to be in contact is if the distance between their carbon-alpha atoms are within some preset cutoff distance. This definition, or others, could be used in this invention to define a residue-residue contact if the user wishes. Then nnc(r) defines the number of nearest neighbor contacts the r-th molecular constituent has with other molecular constituents. A more detailed all-atom description is recommended for the preferred embodiment, which is general for any type of molecular constituent. A nearest neighbor contact is defined to exist between two molecular constituents if they are covalently bonded to one another, or if the number of distinct non-bonded inter-atom-pairs is greater than some user-defined fixed number, such as 3. An inter-atom pair is formed when the distance between atoms from each molecular constituent is less than some user-defined preset cutoff distance. These user-defined cutoff criteria can be adjusted to obtain the best FED. In the preferred embodiment, the quantity nnc(r) will be required in both the FED and FER.

Solute-Solvent Hydrogen Bond:

A H-bond that forms between atoms listed in a template structure is called an intramolecular H-bond. Suppose a particular intramolecular H-bond is identified to form between molecular constituents x and y. When each molecular constituent (x and y) is exposed to solvent, the H-bond breaks, and the free energy of solvation is accounted for by the solvent interactions assigned to each molecular constituent. For the case that one molecular constituent is buried, while the other is exposed to mobile solvent, the intramolecular H-bond may break or form. Let $\eta_{hb}$=0 when the hb-th intramolecular H-bond breaks, or $\eta_{hb}$=1 when the H-bond is present. When an intramolecular H-bond breaks it becomes possible for a H-bond between the solute and solvent to form. In terms of $\eta_{hb}$ and the solvent states of each molecular constituent, the free energy for a solvent H-bond ($s_{hb}$) is given by:

$$G_{shb}=(h_{shb}-TR\alpha_{shb})[(\Delta(s_x,b)\Delta(s_y,c)+\Delta(s_y,b)\Delta(s_x,c))+ (\Delta(s_x,b)\Delta(s_y,m)+\Delta(s_y,b)\Delta(s_x,m))(1-\eta_{hb})].$$

Notice that having one molecular constituent buried, while the other exposed to solvent, or vice versa, is a necessary condition for an intramolecular H-bond to break. Upon breaking, a solvent H-bond will form between the structure and solvent. Therefore, $G_{shb}$, is the free energy of a typical H-bond that forms between a molecular constituent and solvent molecules. The preferred embodiment has an important feature that solute-solvent H-bonds depend on the local solvent state details of molecular constituents. In this example, a solute-solvent H-bond is not possible when both molecular constituents are buried.

Solvent-Interface Interaction:

The coarse-graining procedure of using only three solvent states produces unwanted artifacts. A way to avoid these artifacts is to introduce more solvent sates to obtain a geometrically varying description of the solvent environment that is experienced by a molecular constituent. Because of the geometrical aspect, this description should also depend on the conformation state of the molecular constituent. Within a DCM paradigm, the FED and FER can handle this type of sophisticated detail. However, more details require more FED parameters that need to be determined, and computational complexity increases in the FER. Therefore, in the preferred embodiment, another term is provided to correct for the unwanted artifact that one side of a molecular constituent can be exposed to solvent, while the opposite side is buried. In the art of Computational Biology free energy contributions from solvent interactions are often related to solvent accessible surface area of the molecular constituents. This approach could be employed here as well, which would keep the model reasonably simple.

In the preferred embodiment, a molecular constituent is considered to be either 100% buried or 100% exposed, and these percentages are not split. Instead, enthalpy $h_{slv}(s|r)$ and entropy $\alpha_{slv}(s|r)$ contributions from the r-th molecular constituent are modified with a correction term that is a function of nearest neighbor contacts, nnc(r). This correction term accounts for the interface free energy between the r-th molecular constituent and implicit solvent. Small values of nnc(r) indicate a large interface to solvent exist, while a large nnc(r) indicates the molecular constituent does not have an interface problem. The parameters $h_{slv}(s|r)$ and $\alpha_{slv}(s|r)$ relate to the transfer free energy of the r-th molecular constituent from one solvent to another. To include a correction term, the parameters become modified by a simple shift given as: $h_{slv}(s|r) \to h_{slv}(s|r) + \delta h_{slv}(s|nnc,r)$, and $\alpha_{slv}(s|r) \to \alpha_{slv}(s|r) + \delta \alpha_{slv}(s|nnc,r)$. An exponential decay or some other fast decaying function of nnc provides a reasonable boundary layer model that smoothly interpolates from surface properties caused by an interface to bulk properties, having no interface.

Within this preferred embodiment, details of how to model $\delta h_{slv}(s|nnc,r)$ and $\delta \alpha_{slv}(s|nnc,r)$ must be supplied by the user-defined FED. It is noted here that these functions will reflect the nature of the solvent and molecular constituent. If the implicit solvent is aqueous solution, the correction terms will promote or penalize a buried state to occur for molecular constituents at the surface having favorable or unfavorable interactions with water respectively. If the implicit solvent is non-polar, the correction terms will penalize the exposed state (referring to water) for all molecular constituents at the surface.

As a side remark, the proximity of the r-th molecular constituent to all other molecular constituents within the template structure determines nnc(r), and the index, r, defines a specific molecular constituent, not just a type. Therefore, the functional form given as $h_{slv}(s|r) + \delta h_{slv}(s|nnc(r),r)$ is just a function of r. The discussion about the correction terms is important from the point of view of the FED to account for the solvent-solute interface. However, when enthalpy and entropy contributions are reconstructed in the FER part of this invention, the identification of the source of these solvent contributions (bulk versus surface) is irrelevant. Therefore, $h_{slv}(s|r)$ and $\alpha_{slv}(s|r)$ are interpreted as including surface effects if the user-defined FED calls for it. For example, these correction terms could be ignored if the user wishes, or the user can employ the common approach of using exposed accessible surface areas to estimate solvent free energy contributions. Irrespective of the amorphous nature in the details of a FED, the universal form for the solvent related FED reduces to the specification of $h_{slv}(s|r)$ and $\alpha_{slv}(s|r)$ that gets passed on to the FER. As another point about a universal form for a general DCM solver, the mDCM can be recovered by employing only one solvent state, and setting $h_{slv}(s|r)=0$ and $\alpha_{slv}(s|r)=0$.

General Properties of Solvent Parameters:

Both $h_{slv}(s_r)$ and $\alpha_{slv}(s_r)$ represent functions of solvent conditions (i.e. concentrations of solutes, co-solvents, pH, etc) and thermodynamic conditions (i.e. temperature and pressure). In practice, the smallest $Ns_r$ and least number of explicit variables used in the functions describing these parameters makes the effort in constructing the FED and the calculations involved in the FER the simplest. However, greater accuracy may be achieved by choosing to use a larger number of discrete states. These general trade-off issues hold true for all other parameters that make up the embodiment for the FED.

General Properties of Conformation Interactions:

Any type of interaction between two or more atoms within a template structure is classified as a conformation interaction. In the preferred embodiment, conformation interactions model intramolecular interactions and the effect of clathrate solvent on atomic structure. Conformation interactions affect the rigidity and flexibility of atomic structure, and are represented as constraints acting on two or more atoms. This invention characterizes a conformation interaction in a model-independent form as follows:

1) Identification of the internal DOF ascribed to the relative motion between n atoms important to the interaction. For each DOF identified, a constraint is introduced to characterize the interaction.
2) Specification of global energy and entropy contributions for each constraint and its member bars, including other global physical properties and the spatial distribution of the bars within.

Figure 6:
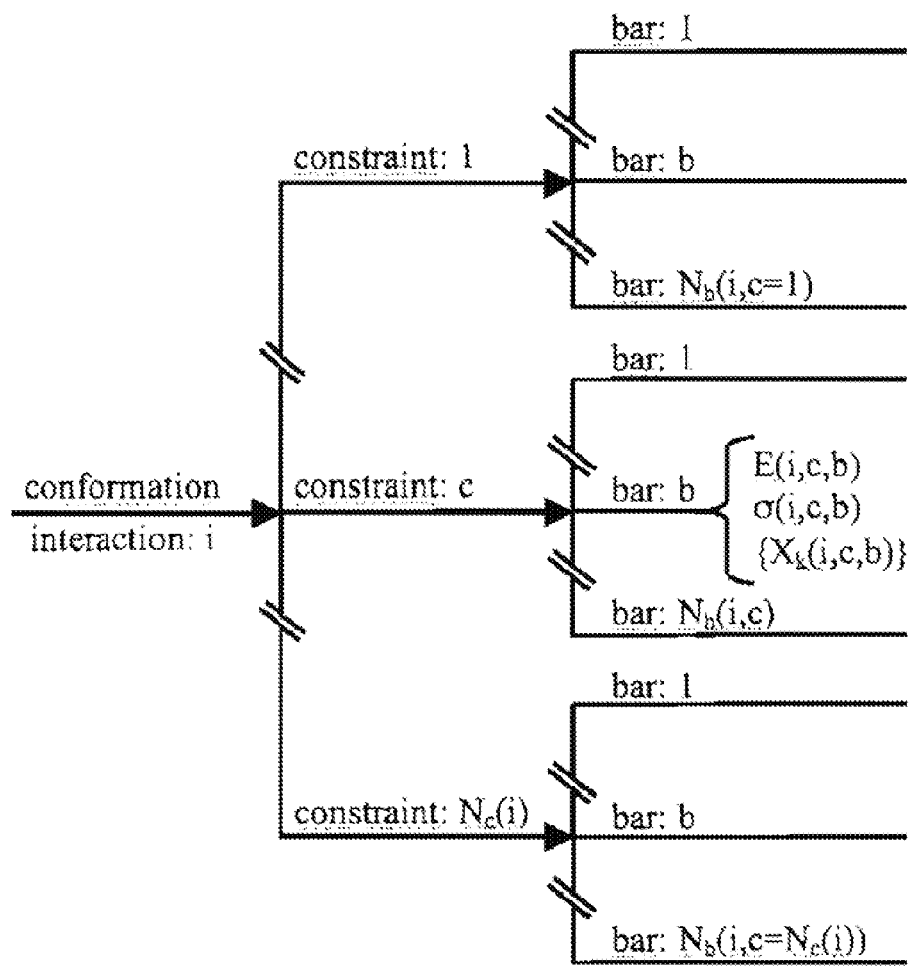
FIG. 6: Schematic diagram showing a hierarchical indexing scheme for conformation interactions.

FIG. 6 is a schematic diagram showing a hierarchical indexing scheme for conformation interactions. When an interaction has multiple constraints, all constraints are simultaneously present whenever the interaction is present. When a constraint has more than one bar, only one bar is present at a given time. Each distinct bar is assigned an energy, $E(i,c,b)$, a pure entropy, $\sigma(i,c,b)$, and a variety of physical properties associated with a specific bar, where $X_k(i,c,b)$ represents the k-th physical property.

The preferred embodiment represents conformation interactions using a hierarchical form of indexing as shown in FIG. 6 with indices $\{i, c, b\}$. The top most level index, i, labels a conformation interaction; then, c, labels individual constraints that make up a particular interaction type, and; b, labels individual bars that make up a given constraint type. For the i-th interaction, $N_c(i)$ gives the number of constraints distributed among n atoms in such a way that all constraints will be independent when these n atoms are considered as an isolated system. In constructing a FED for a particular conformation interaction, each constraint removes precisely one internal DOF. A constraint can be represented as a single bar or multiple bars for which only one bar is present at a time. $N_b(i,c)$ denotes the number of bars within constraint, c. Each bar is assigned a conditional probability, $a(i,c,b)$, for it to represent the constraint, c, given that interaction, i, is present. The property that a constraint removes one DOF implies the following sum rule:

$\Sigma_b a(i,c,b)=1$ summing over all bars that are members of constraint $c$      Eq. (3)

Each bar when present contributes to energy, $E(i,c,b)$, pure entropy, $\sigma(i,c,b)$, and to the k-th physical property, $X_k(i,c,b)$. Based on bar energies and entropies and their factorization into separate constraints, a molecular partition function for the i-th conformation interaction is constructed. Physical properties associated with an interaction are readily calculated through the art of Statistical Physics as ensemble averages from the molecular partition function. For the i-th conformation interaction, its molecular partition function, $Z_i$, is given by the following two formulas:

$$Z_i = \prod_{c=1}^{N_c(i)} Z_c(i) \text{ where} \qquad \text{Eq. (4)}$$

$$Z_c(i) = \sum_{b=1}^{N_b(i,c)} \exp(\sigma(i, c, b)) \exp(-\beta E(i, c, b)).$$

The factorized product over all $Z_c(i)$ indicates an "and" operation, such that the contribution from each constraint occurs simultaneously when interaction, i, is present. In contrast, the sum over all bars to obtain $Z_c(i)$ indicates an "or" operation, such that only one bar contribution occurs at a given time. Furthermore, the average value for the k-th physical property associated with conformation interaction, i, is given by:

$$\langle X_k \rangle = \sum_{c=1}^{N_c(i)} \langle X_k \rangle_c \text{ where} \qquad \text{Eq. (5)}$$

$$\langle X_k \rangle_c = \sum_{b=1}^{N_b(i,c)} X_k(i, c, b) \frac{\exp(\sigma(i, c, b)) \exp(-\beta E(i, c, b))}{Z_c(i)}.$$

$$\langle X_k \rangle = \sum_{c=1}^{N_c(i)} \langle X_k \rangle_c \text{ where}$$

$$\langle X_k \rangle_c = \sum_{b=1}^{N_b(i,c)} X_k(i, c, b) \frac{\exp(\sigma(i, c, b)) \exp(-\beta E(i, c, b))}{Z_c(i)}.$$

Linearity in average properties over all constraints follows because each constraint operates independently and simultaneously. The conditional probability, a(i,c,b), for the b-th bar within constraint, c, is given by:

$$a(i, c, b) = \frac{\exp(\sigma(i, c, b)) \exp(-\beta E(i, c, b))}{Z_c(i)} \qquad \text{Eq. (6)}$$

Notice that a(i,c,b=1)=1 in the special case that $N_b(i,c)=1$, which means that if a single bar represents a constraint, then it is present 100% of the time when the constraint is present.

A constraint can be localized between two vertices within a body-bar network, or it can be distributed over a region of vertices that may or may not be contiguous. If a constraint is localized, each of its bars will be placed between a single pair of vertices. A conformation interaction involving n-atoms, for n≥3, is distributed, but it may consist only of multiple localized constraints. Because localized constraints act independently from one another, this representation does not enforce cooperativity among the constraints within the interaction. When cooperativity is a desirable feature, an interaction can be represented using distributed constraints that places a bar between multiple pairs of vertices simultaneously. Each bar that represents a distributed constraint is subdivided into parts, and these parts are then distributed over the appropriate pairs of vertices. The individual parts of a bar are still considered bars, but they are assigned a weight factor indicating their fraction of the complete bar. This weight factor, $w_{mn}(i,c)$ is applied to all bars within a given constraint, c, where the indices (m,n) represent a particular pair of vertices. The fractional bars sum back to a complete bar, which is reflected in the following sum rule:

$$\Sigma_{(m,n)} w_{mn}(i,c,b)=1 \text{ summing over all pairs of vertices defined by the distributed constraint } c \qquad \text{Eq. (7)}$$

A bar defines a specific entity with global properties, which are independent to how it is spatially distributed. The global properties of a bar consisting of energy, entropy and other physical properties are augmented with the specification of how it is spatially distributed. The spatial distribution is specified by a set of functions $\{w_{mn}(i,c,b)\}$ for all pairs of vertices $\{(m,n)\}$, and this topological detail tied to the body-bar network is associated with a constraint, for which each of its bars inherit. For example, the conditional probability that the b-th bar is present, a(i,c,b), applies globally, such that when the bar is present, it is distributed in accordance with the spatial distribution characteristics given by $\{w_{mn}(i,c,b)\}$. The preferred embodiment keeps the form of Eqs.(3,4,5,6) the same whether dealing with a localized or distributed constraint. The set of spatial weight functions, $\{w_{mn}(i,c,b)\}$, is used in a technical way within the FER part of this invention because the details of how the bars are distributed in the body-bar network will influence whether they are redundant or independent.

Figure 7:
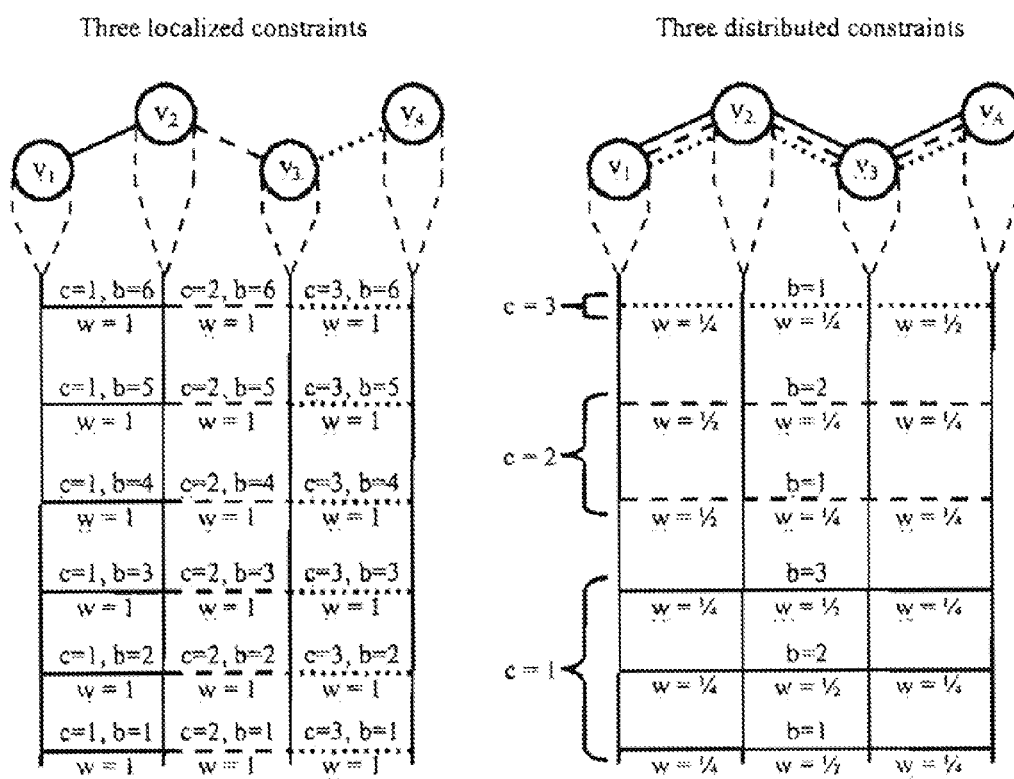
FIG. 7: Comparison of 2 interaction types involving 4 vertices along a chain and 3 constraints shown as solid, dashed and dotted lines.

FIG. 7 is a comparison of two interaction types involving 4 vertices along a chain and two constraints shown as solid, dashed and dotted lines. On the left and right sides, the top drawings show the location of localized and distributed constraints respectively. The lower schematics label constraints, bars and spatial weights. On the left, there are 3 localized constraints, each with 6 bars, and all have a spatial weight function, w=1. On the right, there are 3 distributed constraints, with 3, 2 and 1 bar each. The bars divide into two spatial weights of ¼ and one with a weight of ¼. Since only one bar within a constraint can appear at any given time, the total weight of bars connecting vertices (v1,v2), (v2,v3) and (v3,v4) are all equal to 1. Thus, in both cases, a net number of 3 DOF is constrained using a total of 6 bars.

Constructing a FED based on the preferred method treats a group of n-atoms as an isolated system to allow the user to enforce all constraints within a conformation interaction to be independent in terms of rigidity. Statistical fluctuations are also present when probabilities are assigned to bars to determine which one will represent a constraint at any given time. In this statistical sense, the degree of cooperation within a particular interaction is affected strongly by how the constraints are spatially distributed. As an example, compare three localized constraints, each consisting of 6 bars, to three distributed constraints having 3, 2 and 1 bar, as shown in FIG. 7 involving 4 vertices. The response characteristics of the conformation interactions resulting from the localized and distributed representations will be different from one another, despite that both interaction types involve 3 DOF over the same kind of 4-atom chain. The spatial weights for the distributed constraints in FIG. 7 were chosen to illustrate non-uniformity can be accounted for, if so desired. Details on how to represent a conformation interaction are a modeling issue for a user to select. This invention provides a computer-implemented tool to facilitate the FED construction process.

For n≥3 atoms, it is possible to use $N_c(i)=3n-6$ constraints to represent a conformation interaction, such that all the constraints will be independent when well placed as localized or distributed constraints. If done, then the interaction is complete for this group of n-atoms. Alternatively, $N_{pdc}$ number of previously defined constraints that are independent can be considered within a group of n≥3 atoms. Then, $N_c(i)=(3n-6)-N_{pdc}$ is the number of additional constraints that can be placed within this group of atoms, and still all be independent. In this way, a user can construct a FED by bootstrapping new interactions in terms of previously defined interactions. If bootstrapping is used, it is preferable to place the constraints associated with lower entropy assignments before constraints with higher entropy assignments.

For a group of n atoms, with n≥3, a FED must account for 3n−6 independent constraints. However, these atoms are represented as n rigid bodies in the body-bar network. Since each body has 6 DOF, a total of 6(n−1) independent constraints must be defined to rigidify these n bodies. The requirement of 6(n−1) constraints is more than 3n−6. The preferred embodiment resolves this mismatch by starting from the mapping of a covalent bonded atomic network onto a body-bar network. In this mapping, 5 bars are placed between pairs of vertices to represent a rotatable covalent bond. The strongest interactions with lowest entropies are associated with covalent bonding. These interactions physically play no interesting thermodynamic role, but are critical in the mechanical aspect of forming a polymer chain. Incorporating a special class of constraints, called passive constraints, eliminates the mismatch in constraint counts. Each passive constraint is localized and represented as a single quenched bar. Passive constraints are placed in the body-bar network before any other constraints that are associated with conformation interactions. The numbers of passive constraints will be the main source of previously defined constraints within a group of n atoms. In the preferred embodiment, passive constraints are placed only between pairs of vertices as part of covalent bonding, and they serve the purpose to make up the difference in mismatch between counting constraints in the atomic structure compared to the corresponding body-bar network. When distributed constraints are used, the mismatch in constraint counts can be fractional. In these cases, fractional passive constraints can be defined and used in the same way.

This invention specifies a general form for selectable embodiments for a user-defined FED and FER. The user will have the freedom to represent conformation interactions in many different ways, with the goal to reproduce observed physical properties correctly when the interaction is isolated, or nearly so for an experimental setup. It is expected that more than one representation will be successful in reproducing experimental observations in a variety of measurable features. Representations that yield accurate and robust overall descriptions in real applications will determine the FED scheme that will be frequently employed by user selections. This invention provides the user considerable freedom in building a FED, and it is expected that multiple good choices will be possible due to the amorphous character of a FED.

Example Representations

Figure 8:
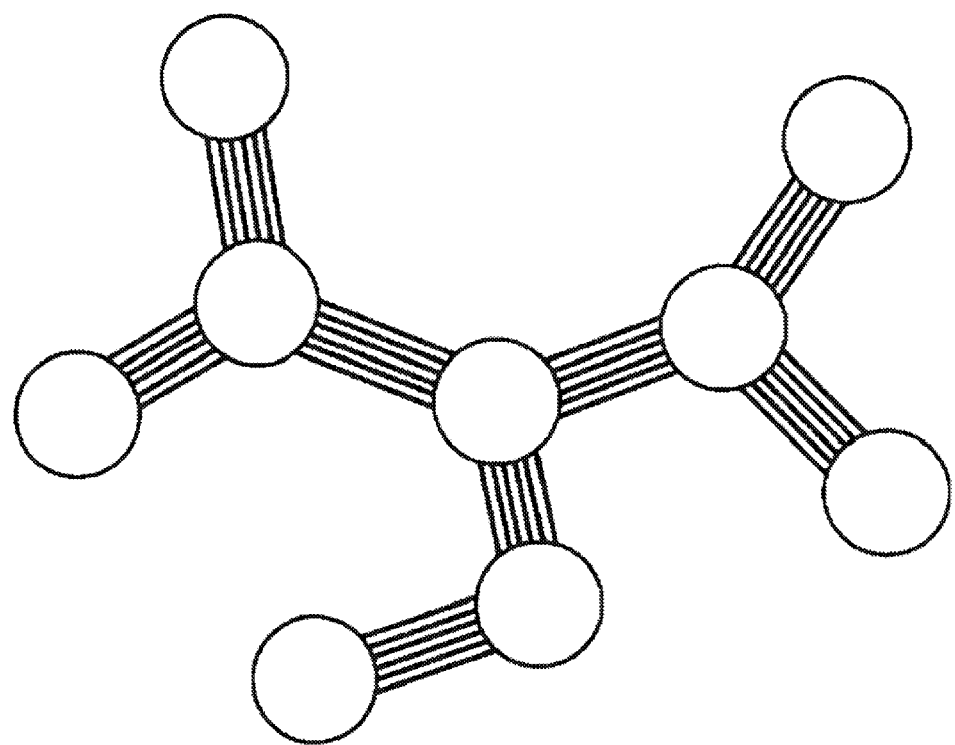
FIG. 8: Illustration of a passive conformation interaction that makes a chemical constituent rigid when it is exposed to a clathrate solvent environment.

In practice, the general representation for a conformation interaction described above will not be used fully for a given interaction type. In some cases, the energy or entropy parameters need not be explicitly specified because they play a passive role. For example, the conformation interaction shown in FIG. 8 represents atomic structure of a chemical group as a rigid body when it is exposed to solvent in a clathrate environment. In the preferred embodiment, all internal DOF are eliminated from the chemical group using a full allotment of passive constraints whenever solvent controls atomic motion.

FIG. 8 is an illustration of a passive conformation interaction that makes a chemical constituent rigid when it is exposed to a clathrate solvent environment. Circles represent rigid bodies in the body-bar network, and there are enough passive bars placed between the bodies to eliminate all internal DOF within the structure.

The general representation for conformation interactions enables an amorphous FED to be defined using a canonical form to facilitate passing relevant information to the FER part of the invention. The FED together with the FER provides a general purpose DCM solver. The computer-implemented system and method utilizes a variety of FED embodiments to represent different types of conformation interactions. A complete FED will be obtained if all elements are selected from the examples given here, which split into two broad classifications as either localized or distributed conformation interactions.

Localized Conformation Interactions

Figure 9:
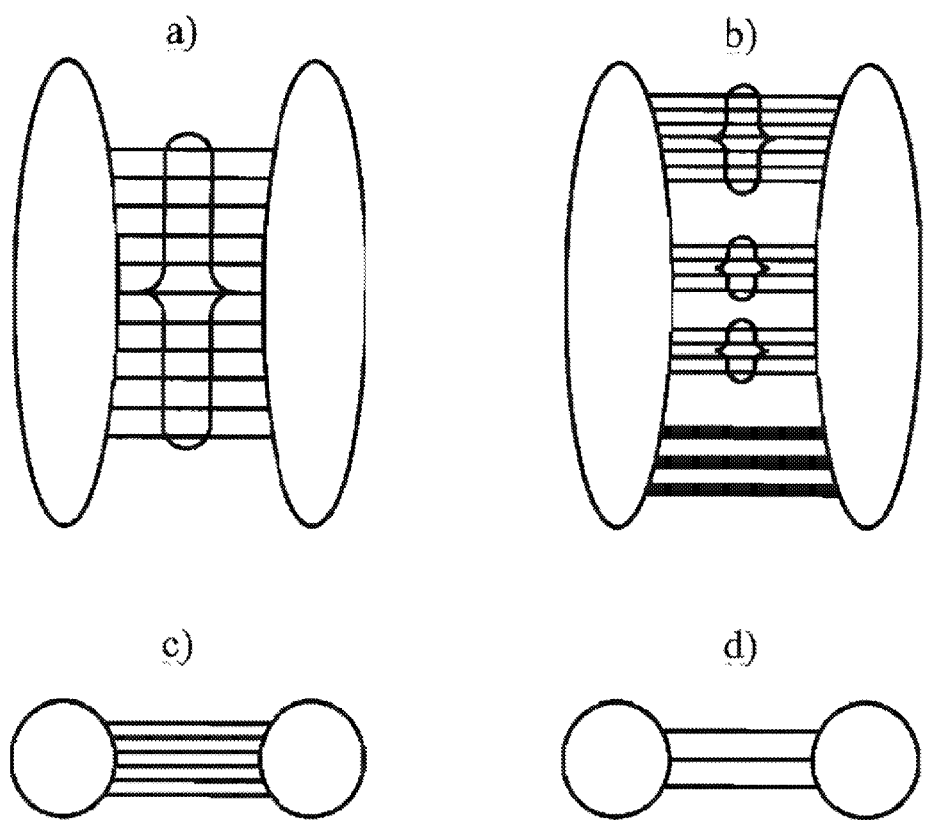
FIG. 9: Schematic examples of 4 different types of conformation interactions. Elongated ellipses and circles represent rigid bodies, which are generally assigned 6 DOF, or 3 DOF when the object represents an isolated atom.

Example representations for an ionic bond, covalent bond, clathrate contact and hydrogen bond are shown in FIG. 9 as selectable embodiments. All these conformation interaction types involve one or more localized constraints between a pair of vertices. The preferred embodiment for each of these interactions is now briefly described in turn as illustrative examples.

As noted above, FIG. 9 shows schematic examples of 4 different types of conformation interactions. Elongated ellipses and circles represent rigid bodies, which are generally assigned 6 DOF, or 3 DOF when the object represents an isolated atom. a) Multiple bars denoted by lines are used to represent an ionic bond as members of one constraint that is denoted by the double closed bracket symbol. b) Six constraints are used to represent a covalent bond, of which three are passive constraints denoted as thick lines, and the other three constraints denoted by the double closed bracket symbol consist of a number of bars. c) A clathrate contact is represented as six constraints, each consisting of one bar. d) A hydrogen bond is represented as three constraints, each consisting of 1 bar, between the donor and acceptor atoms.

Example of Ionic Bond:

An ionic bond is represented as one constraint consisting of $N_b$ bars, as FIG. 9a schematically shows. Employing more bars increases the variable character of an ionic bond in terms of broaden energy and entropy distributions. Ionic bonds will be primarily used to model interactions with isolated atoms, for which they may actually be ions. Isolated atoms are identified as those atoms in the molecular structure that do not participate in covalent bonding with other atoms. In practice, isolated atoms will generally be metal atoms or ions. In the body-bar network, isolated atoms are modeled as an isolated vertex with 3 DOF assigned. Ionic bonds will form between an isolated atom and any number of atoms in sufficient proximity based on distance cutoffs related to empirical ionic bond length criteria. The required energy and entropy parameters are expected to depend on local environment, dielectric properties of the medium, and be functions of ionic strength and other solvent and thermodynamic variables.

Example of Covalent Bond:

As shown in FIG. 9b, a covalent bond can be represented as 3 passive constraints and 3 constraints that consist of a number of bars. In the simplest case, which should suffice for most applications, two of the three latter constraints are considered to be degenerate, each consisting of one bar, and the third constraint consist of two bars. The degenerate pair of constraints model bond-bending angular forces, while the third constraint models the dihedral angle twist associated with torsion forces. The two bars used to represent the torsion interaction correspond to the metastable cis and trans states observed experimentally. More bars can be included if more distinguishing characteristics are known and are necessary to model. Since a covalent bond is being modeled, each vertex that the bars connect have 6 DOF assigned. An exception is made to this representation when one or both vertices are dangling ends. In this case, the simplest model is to use 6 passive constraints. To account for bond-stretching and angular bond-bending flopping of a dangling end, 5 or 4 passive constraints can be used with one or two constraints each consisting of one or more bars respectively. At this coarse-grained level, it is possible to use passive constraints, and avoid the problem of determining the bar parameters that are introduced. The number of passive constraints can be reduced if the user wishes to discern more subtle variation. The extent of experimental data, and desired resolution to distinguish subtle characteristics together determine the parameterization that will be needed.

Example of Clathrate Contact:

A clathrate contact as illustrated in FIG. 9c is introduced to model the affect of clathrate solvent on the conformation of atomic structure. A clathrate contact forms between two chemical groups that are directly covalent bonded to one another, while both groups are exposed to solvent in a clathrate environment. When this situation occurs, the conformational freedom normally enjoyed by the covalent bond linker is restricted by solvent-solvent interactions that form a cage effect, or direct solvent-solute interactions. Reduction of conformational freedom in proximity of the linker is modeled using additional constraints between reference vertices of each chemical group. For example, the reference vertex could be the alpha carbon atom in an amino acid residue found in proteins. The clathrate contact ensures solvent-solvent interactions control the conformation of neighboring chemical groups that are simultaneously exposed to solvent with clathrate characteristics. The number of constraints representing a clathrate contact can range from 1 to 6. The representation for a clathrate contact can be further extended to include any pair of chemical groups that have reference vertices located in the template structure within a user-defined cutoff distance regardless if they are directly covalent bonded or not. In the preferred embodiment, a clathrate contact forms only between chemical groups sharing a covalent bond linker, and is represented using 6 degenerate constraints, each consisting of 1 bar. Hypothetically, if all residues of a protein were exposed to clathrate-solvent, then the ensemble of clathrate contacts will aggregate all rigid residues into a super sized rigid cluster involving all atoms of a protein. Consequently, a fully hydrated protein is viewed as loosing the maximum conformation entropy possible.

Example of Hydrogen Bond:

A hydrogen bond (H-bond) can be represented as three constraints placed directly between its donor and acceptor atoms as FIG. 9d illustrates. Each of these constraints can be assigned multiple bars. In the preferred embodiment, one bar is used to represent each constraint. The energy and entropy parameters characterizing a H-bond will depend on local geometrical details involving its donor and acceptor atoms and their covalent bonded neighbors. The atomic hybridization of donor and acceptor atoms is used to chemically classify H-bonds into different types. H-bonds in a template structure are identified using geometrical criteria common in the art of Computational Biology. A family of H-bonds is defined by a collection of all possible H-bonds sharing the same atomic hybridization, but having different geometries. Within a family, H-bonds are classified further based on coarse-grained geometrical characteristics. For example, the donor to acceptor distance, $d_{HB}$, characterizes a H-bond as short-, medium- or long-ranged. Greater descriptive accuracy is achieved by including more graduations, such as 5 bins instead of 3, or 11 bins instead of 5. Another descriptor of geometry is to specify the angle, $\theta HB$, between the donor atom, the hydrogen atom shared by the donor and acceptor atoms, and the acceptor atom. Combining the two descriptors, $(d_{HB}, \theta_{HB})$ forms a two dimensional grid that can be used for binning regions. The nature of the characteristics used to establish bins must be user-defined.

Suppose $(E_1, \sigma_1)$, $(E_2, \sigma_2)$, $(E_3, \sigma_3)$ are (energy, entropy) assignments for a bar representing constraint 1, 2, and 3 respectively as FIG. 9d schematically shows. Because all three constraints are either present or not present simultaneously when the H-bond forms or breaks respectively, the energy of the H-bond when present is given by $E_{HB}=E_1+E_2+E_3$. An equivalent representation is to associate total energy, $E_{HB}$, to the H-bond without regard to the source of energy contributions. The H-bond conformation interaction is then specified as: $\{E_{HB}, \sigma_1, \sigma_2, \sigma_3\}$. This compact notation is further extended. Imagine that instead of 1 bar per constraint, each H-bond constraint consist of 10,000 bars. Assume each bar that is a member of constraint k is degenerate in pure entropy, characterized by σk that labels the k-th constraint. Now there are as many as (10,000) 3 possible $E_{HB}$ values. In this example, it is best to represent the $10^{12}$ possible energies using an energy density function, g(E). Here $\int g(E) dE = N_E$, where $N_E$ is the number of distinct energies the H-bond can take on, such as $10^{12}$ using the current example.

A simpler representation of the H-bond FED is the specification of an energy density function, and conformation entropies. The preferred embodiment defines a local additive partition function given by:

$$Z_o(bin) = \frac{1}{N_E} \int g(E \mid bin)\exp(-\beta E)dE \qquad \text{Eq. 8}$$

where $g(E \mid bin)$ is user-definded.

where $Z_o(bin)$ becomes the object of interest. The label, bin, explicitly shows this procedure must be done for each coarse-grained bin describing the geometry of the H-bond. The template structure determines which bin to use, and this particular bin defines "native". In addition to $Z_o(bin)$, the pure entropies $\{\sigma_1, \sigma_2, \sigma_3\}$ are functions of bin. In this scheme, the full partition function that is generally given by a product form $Z_{HB}=Z_1Z_2Z_3$, where $Z_k$ is the partition function for constraint k is explicitly given as:

$$Z(bin)=\exp(\sigma_1(bin)+\sigma_2(bin)+\sigma_3(bin))Z_o(bin) \qquad \text{Eq. (9)}$$

where the conformation pure entropies are additive at this point because the group of atoms that define the H-bond are considered as isolated. In the FER part of this invention, individual values for pure entropies for each bar $\{\sigma_1, \sigma_2, \sigma_3\}$ will be needed. However, for the FED part of the invention, it is convenient to define the total entropy to be $\sigma=(\sigma_1+\sigma_2+\sigma_3)$.

In the preferred embodiment, all accessible classes of a H-bond are designated as native or disordered. The form of the FED for a H-bond with specific atomic hybridization, is characterized by $Z_{nat}(bin)$. This particular H-bond is identified within a template structure, and its bin also identified. In the FER part of this invention, regions of atomic structure are considered to be native-like or disordered. If local structure is native-like, the H-bond inherits properties from the template structure. If local structure is disordered, the H-bond is characterized by Zdis given as:

$$Z_{dis} = \sum_{bin} \exp(\sigma(bin))Z_o(bin) \qquad \text{Eq. (10)}$$

where $Z_{dis}$ depends on family characteristics of the H-bond. Note that the disordered H-bond state includes the bin that characterizes the template structure. The native-like bin is not treated as special. Specifically, $Z_{dis}$, does not depend on native geometry or the particular H-bond under consideration. The partition function, $Z_{nat}$(bin), depends on the identified bin that combines characteristics of local geometry of a particular H-bond in the template structure. Consequently, $Z_{nat}$(bin) accounts for the spatial inhomogeneity in H-bond properties.

Figure 10:
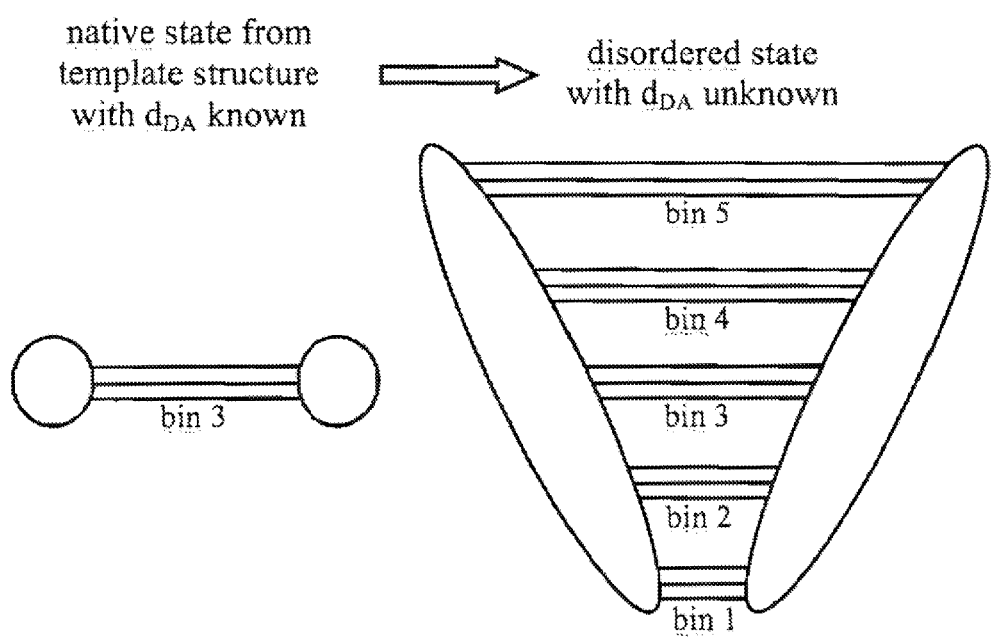
FIG. 10: Comparison between native and disordered states of a H-bond. Circles and elongated ellipses represent rigid bodies.

FIG. 10 is a comparison between native and disordered states of a H-bond. Circles and elongated ellipses represent rigid bodies. On the left, a representation of a native H-bond consisting of 3 constraints, each with 1 bar, having properties that depend on the local geometry defined by the template structure, such as the distance between the donor and acceptor atoms, $d_{DA}$. On the right, in the disordered state, the geometry of the H-bond fluctuates. Due to coarse-grained binning, a finite number of bins are used to represent a range of accessible distances, $d_{DA}$, between donor and acceptor atoms. The schematic of the two ellipses splayed shows that different distance characteristics are associated with different properties of constraints, and their member bars. Consequently, a disordered H-bond is modeled by a collection of constraints, each having properties reflecting coarse-grained geometrical properties.

In the preferred embodiment, disordered states are generic, void of any information from the template structure. If the atoms that form a H-bond are isolated, then by the preferred methodology to construct a FED, all three constraints will be independent, and physical properties intrinsic to a H-bond are governed by $Z_{dis}$. For example, the probability for three constraints having entropies $\sigma_1$(bin), $\sigma_2$(bin) and $\sigma_3$(bin) for a certain geometry characteristic associated with a particular bin, is given as:

$$PROB(\text{constraint } k, bin) = \frac{\exp(\sigma_k(bin))Z_o(bin)}{Z_{dis}} \quad \text{Eq. (11)}$$

An exemplar physical property associated with a bin is its typical donor-acceptor length $d_{HB}$. The average donor-acceptor distance and its fluctuations that are measurable can readily be calculated from Eq.(11) using the art of Statistical Physics. To illustrate the utility of having $Z_{nat}$(bin) and $Z_{dis}$ defined, FIG. 10 compares the difference in representing a H-bond within native-like and disordered environments. Only 3 bars are used to represent a native-like H-bond, while many bars are required (one bar per accessible bin per constraint) is required to represent a disordered H-bond. The FER will take into account the relative probability of finding a H-bond in a locally disordered or native-like region in the template structure.

Distributed Conformation Interactions

Example representations for intra-residue interactions and inter-residue interactions useful for proteins are given to illustrate the utility of distributed conformation interactions. The word residue is used in lieu of chemical-constituent, although the methods generally apply to any group of covalently bonded atoms that a user might perceive as being important building blocks of a large molecular system. The general features are presented in terms of a hypothetical chemical constituent. For applications to proteins, the amino acid residues are the objects of interest in the preferred embodiment. There are many possible ways to represent a chemical constituent as a set of distributed constraints. The method for constructing such a representation as a preferred embodiment consists of 5 steps:

1. Determine local energy minimums throughout the energy landscape of the chemical constituent in terms of key geometrical features perceived important to the user for the application of interest. Saddle points in the energy landscape can be included. Designate all regions that are listed as bins, and create an encompassing leftover bin (or leftover bins) that holds all remaining regions that are accessible, but not accounted for in the listed regions. An example of such a procedure is to use the PHI and PSI backbone dihedral angles of amino acid residues, and identify regions of interest corresponding to the alpha-helix state, beta-strand states, among others. The leftover bin contains coil states and all other regions that are not frequently populated.
2. Using techniques in the art of Statistical Physics and Computational Biology, such as molecular dynamics or Monte Carlo simulation, or sampling an experimental structural database, construct an ensemble of conformations that reflect accessible geometries of the chemical constituent for all designated bins from step 1.
3. From the ensembles generated in step 2, obtain an energy density function for each bin, and from principal component analysis (PCA) obtain the entropy for each eigenvector of a mass weighted covariance matrix using Schlitter's quasi-harmonic approximation [12]. This procedure generates a spectrum of $N_S+6$ entropy values. By selecting a fixed reference frame, of these entropies will be zero, associated with trivial rigid body motions. The NS non-zero entropies characterize internal motion associated with a collective mode that generally extends over all member atoms to some degree within the chemical constituent. Other methods can be used in place of PCA analysis, but the desired feature is to obtain a set of modes and their corresponding entropies.
4. Model each mode found in step 3 as a constraint. Each constraint can be assigned more than one bar, but in the preferred embodiment, one bar per constraint is sufficient for most applications. Similar to Eq.(8) and Eq.(9) construct a local molecular partition function for each residue and for each bin that was identified to be of interest.
5. Each bar considered in step 4 must be spatially distributed within the chemical constituent. In the preferred embodiment, the mapping to bars onto a body-bar network is independent of the bin that characterizes a key geometrical feature.

This 5-step procedure is the preferred method to assign the energy and entropy values to all types of conformation interactions, even if they do not involve distributed constraints. In a sense, a localized constraint is a special case of a distributed constraint, such that the spatial distribution is confined to one pair of vertices. For example, the H-bond parameterization is obtained using these 5 steps with a small variance in step 1. Key geometrical features are used to select bins of interest, rather than local energy minimums or saddle points, which illustrates the binning scheme is ultimately user-defined. A feature of this invention related specifically to a distributed interaction is step 5, involving mapping of a molecular partition function onto a body-bar network representation.

Example of an Intra-Residue Interaction

A user-defined rule or procedure must be specified to represent a distributed interaction consisting of many collective modes involving the atoms within a residue. Although this invention provides flexibility to the user in constructing a custom designed rule, in the preferred embodiment the form of this rule is hierarchical in nature. The rule involves classifying all bars into two types. Bars are either passive or active. Passive bars do not have assigned energy or entropy, whereas active bars have energy and entropy assignments. Passive bars are regarded as the strongest distance constraints, and are therefore placed in the body-bar network before all active bars. Passive bars are essentially used to adjust the number of DOF in a body-bar representation for a molecular system so as to properly model the conformation interactions between atoms, viewed as point particles.

The residue of interest is initially represented as a body-bar network using just enough passive bars to make that structure rigid, without any redundant bar. If necessary, fractional passive bars are used in loops. For example, a single loop of $N_L$ atoms will have $6N_L$ DOF, and will require $(6N_L-6)/NL$ bars to be uniformly placed between each pair of vertices. For $N_L=6$, the number of bars per pair of vertices (there are NL of them) will require 5 passive bars. As further examples, for $N_L=8, 7, 5,$ and 4, the required number of bars is 5¼, 5⅐, 4⅘ and 4½ respectively. This initial type of rigid body-bar network consisting of only independent passive bars is illustrated in FIG. 11 for a hypothetical example structure.

For a residue with N atoms in total, there will be $N_S=3N-6$ non-zero entropy assignments, $\{\sigma_i\}$. The hierarchical procedure is to recursively add one active bar at a time to the network, starting from the highest entropy value to the lowest. For each active constraint added, the spatial weight functions $\{w_{mn}(i,c,b)\}$ must be assigned for each vertex pair (n,m), constraint, c, and bar, b, for the interaction, i, of interest. For a particular vertex pair, given by (m,n), if the total Passive Bar (PB) count is $N_{PB}$, this number is reduce to $N_{PB} \rightarrow N_{PB}-w_{mn}(i,c,b)$ and the active bar replaces the passive bar (or some fraction of a passive bar) with weight $w_{mn}(i,c,b)$. By construction, when all active bars are present, the total number of constraints is the same as when all passive bars were initially present. Consequently, the body-bar description of the residue always enforces the residue to be a rigid object.

Figure 11:
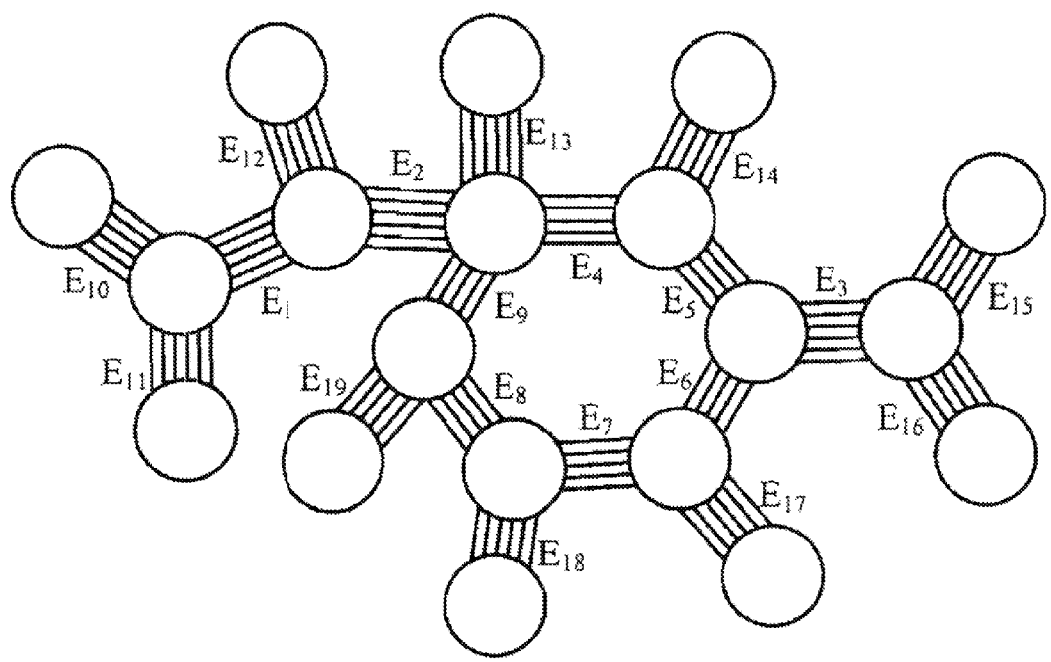
FIG. 11: An example of N=19 atom chemical constituent containing a hexagon loop. Circles define rigid bodies each with 6 DOF.

FIG. 11 is an example of N=19 atom chemical constituent containing a hexagon loop. Circles define rigid bodies each with 6 DOF. The initial body-bar network consists of 108 passive bars that make the structure rigid, with no redundant bar. The 19 edges between rigid bodies defined by covalent bonding to atoms in the corresponding atomic structure are labeled as $E_1, E_2, \ldots E_{19}$. Six passive bars are placed at all edges, except 5 passive bars are placed at each of the edges forming the hexagon loop $\{E_4, E_5, E_6, E_7, E_8, E_9\}$. There are (3N-6)=51 active constraints that can replace passive constraints. Each active constraint will have one bar, which will be spatially distributed over the various edges. As active bars are placed, passive bars are removed in a non-uniform way. From covalent bonding properties, it is known that the bonds labeled by edges $\{E_1, E_2, E_3\}$ are flexible, allowing for dihedral angle motions. Greater spatial weights for the active bars will be assigned to these three edges. Dangling end edges, which are consecutively labeled from E10 to E19, cannot rotate. As such, the active bar spatial weights will be lower for dangling ends, resulting in a greater number of passive bars at dangling ends.

Figure 12:
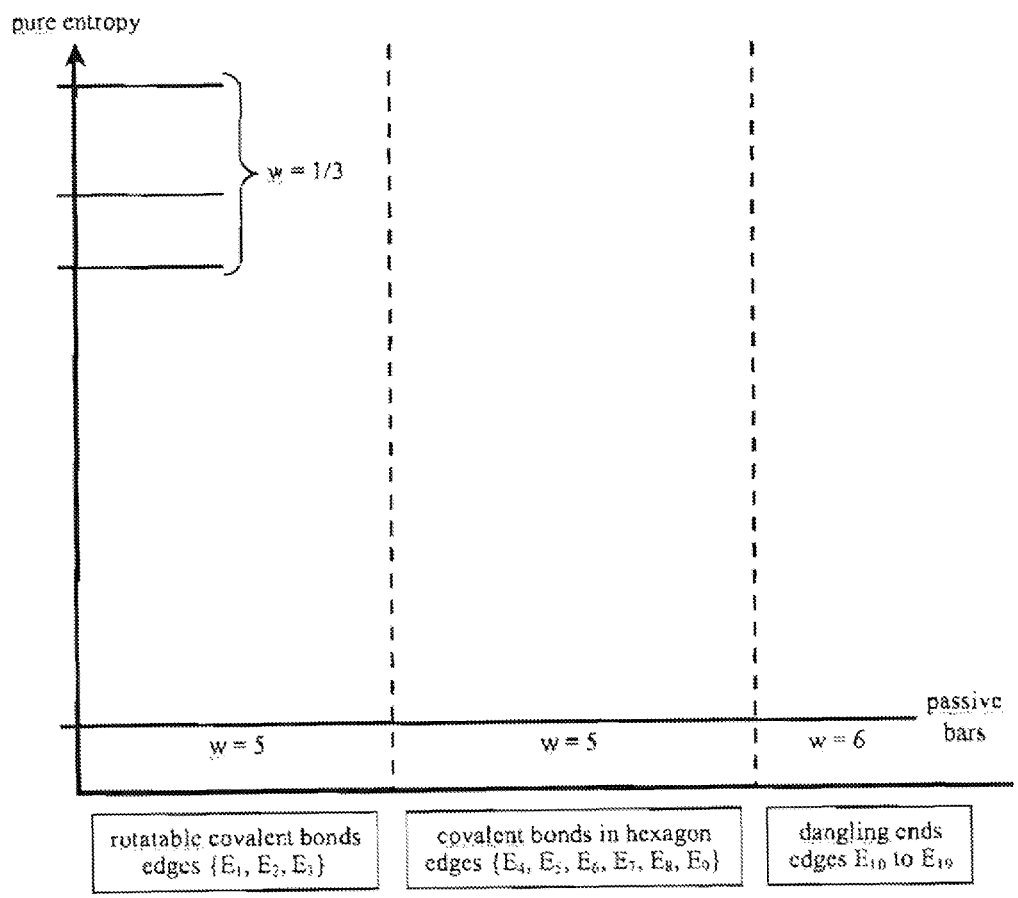
FIG. 12: An example of the entropy spectrum for the intra-residue conformation interaction applied to the chemical constituent shown in FIG. 11, at the hierarchical level of replacing 3 passive constraints with 3 active constraints out of 51.

FIG. 12 is an example of the entropy spectrum for the intra-residue conformation interaction applied to the chemical constituent shown in FIG. 11, at the hierarchical level of replacing 3 passive constraints with 3 active constraints out of 51. In this example, 1 bar is used to represent each constraint. The user must assign spatial weights to each bar. The three most flexible parts of the molecule are located at the covalent bonds that freely rotate. These DOF are locked down by a single constraint distributed over these 3 edges to represent the top 3 ranking modes with highest entropy. The bar corresponding to each distributed constraint is uniformly divided up among these 3 edges, and assigned a weight of ⅓. As a result, one passive bar is removed from each of the rotatable covalent bond edges.

Figure 13:
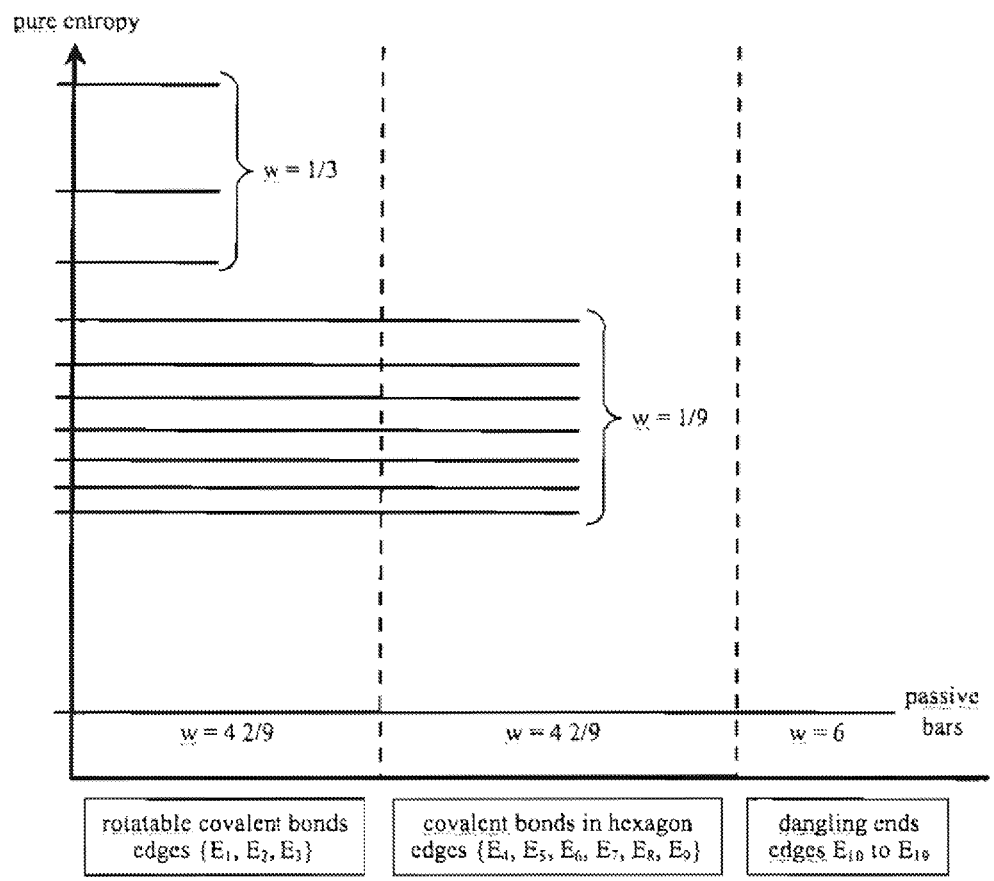
FIG. 13: An example of the entropy spectrum for the intra-residue conformation interaction applied to the chemical constituent shown in FIG. 11, at the hierarchical level of replacing 10 passive constraints with 10 active constraints out of 51.

FIG. 13 is an example of the entropy spectrum for the intra-residue conformation interaction applied to the chemical constituent shown in FIG. 11, at the hierarchical level of replacing 10 passive constraints with 10 active constraints out of 51. Each constraint is represented by 1 bar. The first 3 distributed constraints were explained and shown in FIG. 12. The next set of covalent bonds for which collective modes have greatest influence is all the non-dangling ends. In this example, all 9 non-dangling ends are assigned equal weight of ⅑. These DOF are locked down by a single constraint distributed over these 9 edges (from $E_1$ to $E_9$) to represent the next top ranking modes with highest entropy. As a result, ⅞ of a passive bar is removed from each of these 9 covalent bond edges.

Figure 14:
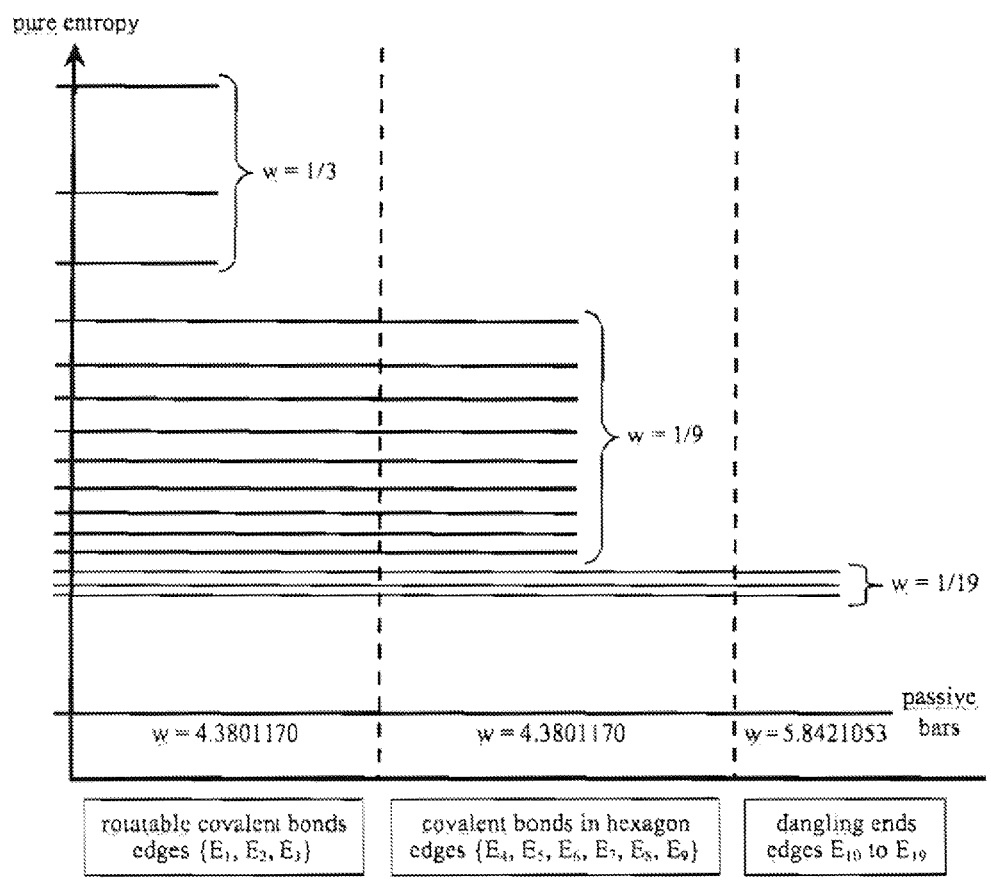
FIG. 14: An example of the entropy spectrum for the intra-residue conformation interaction applied to the chemical constituent shown in FIG. 11, at the hierarchical level of replacing 15 passive constraints with 15 active constraints out of 51.

FIG. 14 is an example of the entropy spectrum for the intra-residue conformation interaction applied to the chemical constituent shown in FIG. 11, at the hierarchical level of replacing 15 passive constraints with 15 active constraints out of 51. Each constraint is represented by 1 bar. The first 3 distributed constraints were explained and shown in FIG. 12. The next 9 distributed constraints follow the logic described in FIG. 13. This leaves 3 additional active constraints to distribute. In this example, all 19 edges are treated on equal footing, and assigned 1/19 weight. The 13-th, 14-th and 15-th constraints lock down 3 DOF using the next three top ranking modes of highest entropy. As a result, 3/19 of a passive bar is removed from each of the 19 covalent bond edges. Rounded to the seventh digit, the remaining weight of passive bars is reported as a decimal number. This example, which builds from the examples also given in FIGS. 11 to 13, gives a simple way of assigning spatial weights to bars, but these weights could be based on the eigenvectors of the collective modes, or some other user-defined criteria. In the preferred embodiment, replacing passive bars with active bars in dangling ends would be deferred until the hierarchy level was considerably higher than 12. In most practical applications, the dangling ends can remain 100% passive.

The hierarchical procedure (step 5) of assigning distributed constraints is applied for each bin that represents an ensemble of structures characterized by a range of PHI and PSI values (as step 1). For each of these bins, a partition function of the same form as Eq.(8) and Eq.(9) is constructed. Although three distinct entropies are used in Eq. (9), more generally the number of distinct entropies for the intra-residue conformation interaction will range over [0, NS] as set by the hierarchical level. A bin of a residue defines a particular conformation state, such as alpha-helix, left-handed alpha-helix, beta, coil and others based on user selection. For any accessible conformation state of a residue, its partition function is determined, and denoted as Z(bin). A partition function that describes all accessible states is called $Z_{dis}$, which has the exact same form and interpretation as Eq.(10). Namely, $Z_{dis}$ is void of any information from the template structure, while the template structure defines the native state by identifying the appropriate bin. The establishment of Z(bin) and $Z_{dis}$ defines a general approach that is applicable to any type of conformation interaction, and is the preferred embodiment for the FED.

Figure 15:
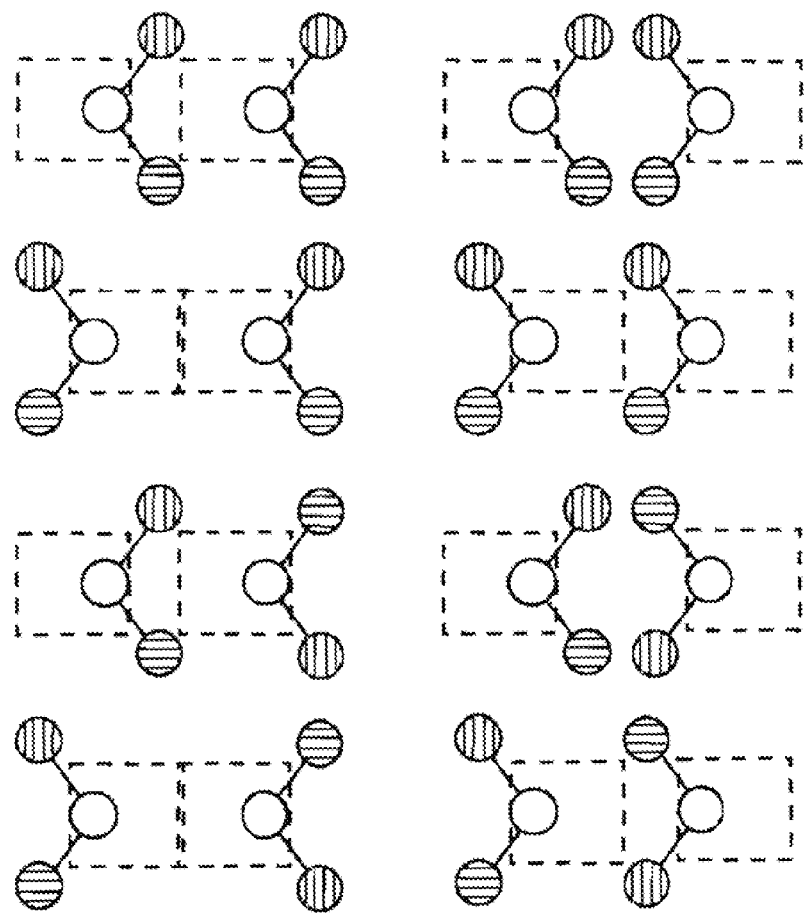
FIG. 15: Schematic diagram that shows examples of relative orientations between two amino acid residues found in a protein.

FIG. 15 is a schematic diagram that shows examples of relative orientations between two amino acid residues found in a protein. Circles with horizontal lines, empty and vertical lines, respectively denote the nitrogen, carbon-alpha and carbon atoms along the backbone. The dashed rectangle represents all other atoms in the residue. Many different orientations can take place between two residues of types X and Y, for which X may equal Y. The distance between the two nitrogen atoms, $d_{NN}$, and the distance between the two carbon atoms, $d_{CC}$, are used as a coarse-grained descriptor of local geometry.

Example of an Inter-Residue Interaction

Non-covalent interactions that form between a pair of residues are modeled as a single effective conformation interaction. Due to the amorphous character of a FED, there is no unique way of defining this type of interaction. The motivation for an inter-residue interaction is to take into account atomic packing between chemical constituents. When the residues become solvent exposed, this inter-residue atomic packing is disrupted. When the structure is native-like, the template structure is used to define a particular conformation state characterized by the partition function Z(bin), where bin is determined based on coarse-grained geometrical criteria. Two residues are defined to be in contact if any atom of one residue interacts with any atom of the other residue through a van der Waals interaction within a specified cutoff distance. Only pairs of residues that come into contact are considered. The distance between the two backbone nitrogen atoms, $d_{NN}$, and the distance between the two backbone carbon atoms, $d_{CC}$, defines a bin. Illustrated in FIG. 15 are example cases, showing relative orientation of the two residues that are in contact. The two distances, ($d_{NN}$, $d_{CC}$) is coarse-grained into a grid of cells (step 1), which is called orientation, 0, for simplicity. For a specified orientation cell, ensembles of structures are collected (step 2) to determine entropy and energy density parameters (step 3).

Figure 16:
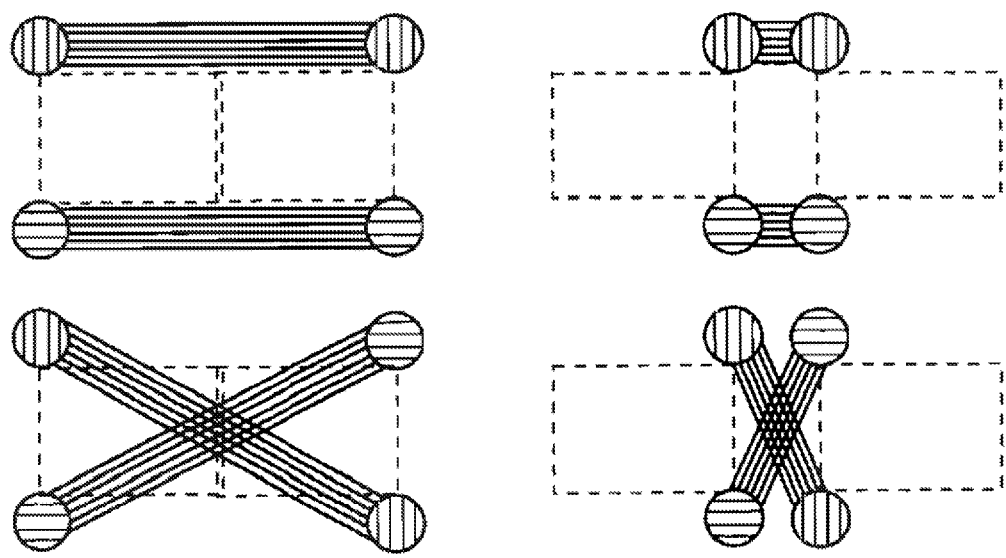
FIG. 16: Schematic examples for how bars are placed to represent the inter-residue conformation interaction.

FIG. 16 shows schematic examples for how bars are placed to represent the inter-residue conformation interaction. There are $N_S=(3\times4-6)=6$ collective modes, each described by a constraint consisting of 1 bar. Each of the 6 bars is spatially distributed with a weight of ½ assigned to a fractional bar placed between the nitrogen atoms (circles with horizontal lines) along the backbone of each residue in the interacting pair. Likewise, a weight of ½ is assigned to a fractional bar placed between the carbon atoms (circles with vertical lines). These example figures are similar to those given in FIG. 15, except the focus is on the body-bar network aspect of the representation. The carbon-alpha atom location and all other member atoms within the residue are schematically shown as a dashed rectangle.

In the preferred embodiment, different families of partition functions are constructed to describe all possible distinct pair of interacting residues and their orientation, $\{Z_{XYO}(bin)\}$. For example, XY denotes a particular residue-residue pair, such as ALA-ALA, ALA-HIS, ARG-GLU, MET-GLY. The orientation, O, is also used as a distinguishing characteristic of an inter-residue conformation interaction family. The set of distributed constraints used to represent the interaction is based on the nitrogen and carbon atoms along the backbone in each residue. For a given pair of residues, this inter-residue conformation interaction consist of N=4 atoms, and $N_S=3N-6=6$ non-zero entropies to determine. Each collective mode is modeled as a distributed constraint, and each constraint is represented as 1 bar (step 4). Each bar is spatially distributed as FIG. 16 depicts between the four vertices that correspond to the nitrogen and carbon atoms of each residue (step 5). After $Z_{XYO}(bin)$ is constructed for all accessible bins, then the corresponding $Z_{XYO,dis}$ is constructed in accordance to Eq. (10) as a general procedure.

Example of Strain Energy Effects

Strain energy can be modeled within a DCM paradigm by relating it to the redundant bars within the body-bar network as determined by the FER part of this invention. In the preferred embodiment, a single global energy parameter, $\in$(type, bin), is specified for each conformation interaction type, and each of its bins. The specification of this energy for all accessible cases of interaction types and bins constitutes the FED, and these energies will be incorporated in the formulas to calculate the partition functions in the FER part of this invention.

Example of Vibration Free Energy Effects

The FED can take into account vibration effects in an effective way, as a generalization to the Einstein model for vibration in solids. In the Einstein model, 3N−6 quantum harmonic oscillators all at the same natural frequency, $\omega_E$, are used to describe the thermodynamic properties of a generic homogenous solid material consisting of N atoms. Besides assuming all oscillators have identical properties characterized by natural frequency, $\omega_E$, it is also assumed in the Einstein model that all oscillators are independent. A selectable embodiment in this invention assigns a natural frequency of vibration to each bar, $\omega_b$, in the body-bar network. This frequency has to be modeled in some user-defined way.

In the preferred embodiment, $\omega_b$, is assumed a function of the bar's assigned entropy parameter, $\sigma$. A smaller $\sigma$ indicates a stiffer spring constant, which corresponds to a higher $\omega_b$. If a bar is found redundant, this indicates that the local network is stiffer than that expected based on the nominal value of the assigned entropy of the bar. A user-defined model can be incorporated to shift the bar's natural frequency to $\omega'_b$ based on network rigidity properties. For any user-defined model, all free energy contributions (including average thermal energy and entropy) of the standard quantum mechanical harmonic oscillators, written as $G(T,\omega'_b)$, $U(T,\omega'_b)$ and $S(T,\omega'_b)$ are considered to be additive contributions. The FER part of this invention will determine what $\omega'_b$ will be based on network rigidity properties. In the FED, a rule needs to be defined on how to determine which oscillator contributes, since in general there will be many more bars in the network than 3N−6 modes of vibration.

Note that as more constraints are present in a network, the stiffer the network will become and the effective vibration frequencies for a large fraction of bars will increase. As constraints are removed from the network, there is a general softening of the network, and the frequencies of the bars will tend to relax to their initial values that assume they are independent. Thus large variations in the spectrum of vibration frequencies will exist between a folded and unfolded protein. Moreover, these effects will depend on the size of the system. For example, as a protein size increases, there will be more low-frequency modes of vibration (even in the folded state), which will result in an increase in entropy due to vibration. Many models can be designed to account for these effects, which can be handled within a general DCM solver.

In a preferred embodiment, bare frequencies are assigned to each bar, based on the pure entropy, a, which does not depend on the size of a system (i.e. protein). Each bare frequency is modified based on a multiplicative factor given by $(A/N)^{1/6}$ where N is the number of atoms within the system, and A is a constant to be empirically determined. The exponent of ⅙ comes from taking a geometric mean of a generic frequency spectrum following the Debye model of vibration modes in solids. Debye argued that a linear dispersion relation due to sound waves is a better model than the Einstein model, with the lowest frequency being proportional to the inverse of the linear dimension of the sample. Here, it is assumed the lowest frequency will be proportional to 1/L, where L is the linear dimension, and volume is proportional to $N^{1/3}$. There will be 3N−6 vibration frequencies present ranging between $\omega_b$ and roughly $\omega_b/N^{1/3}$ for each bar. Let $N_v=3N-6$, which gives the number of non-zero frequency modes. Since there will be $N_v$ frequencies present ranging between $\omega b$ and $(\omega_b)A/N^{1/3}$, a geometrical mean of $[\omega_b\ \omega_b(A/N)^{1/3}]^{1/2}$ gives an effective spectral frequency. The effective frequency, $\omega_{b,eff}$ accounts for the effect of adding mass to a system, such as a protein compared with the same protein bound to a ligand or large complex.

The canonical form for the total free energy contribution due to vibration modes within the system is given as:

$$G_{vib,total}(T) = N_v \frac{\Sigma_b G(T, \omega'_b) p_b}{\Sigma_b p_b} \qquad \text{Eq. (12)}$$

The denominator is just the number of constraints present in the network. The fraction to the far right is an average over contributions from all oscillators present in the network. The frequency of vibration of a bar is not its bare value, and not even the scaled frequencies that take into account the size of the system. The frequency of vibration that appears in Eq.(12) are also functions of the $q_b$, which is the conditional probability that the b-th bar is independent. The user-defined rules to determine $\omega'b$ are part of the FER, and the preferred embodiment for calculating $\omega'b$ is discussed as a component in the FER.

Order Parameters

There are many physical properties of a system that are interesting to monitor, such as the average number of H-bonds, average number of hydrophobic interactions, average number of buried residues, average number of residues caged in clathrate solvent, average number of residues in their native state, average number of independent DOF, average number of rigid clusters and average size of correlated motions. The average number of a certain type of event can be theoretical in nature, but some quantities connect directly to experimental measurements. For example, the degree to which a residue is exposed to solvent can be probed by hydrogen exchange experiments. The average number of times a residue is in a local secondary structure is reflected in spectroscopic circular dichroism (CD) measurements where the signal is accumulated over all residues within a protein. Correlated motions can be probed experimentally using 2D NMR spectroscopy. Not all possible quantities of interest can be calculated for a given DCM, unless the user-defined FED and FER employ all required and relevant variables to calculate the averages.

The characteristics of a user-defined FED will depend on the physical and chemical properties a user is interested in monitoring. The various averages exhibit properties of a system, and those that show clear differences in the character of its macrostate may serve as an order parameter. As the large numbers of examples indicate, many different types of order parameters can be calculated. Order parameters are classified as either secondary or primary. After a calculation is completed, the probabilities of all physical states are known, and the desired average properties can be calculated to obtain the secondary order parameter allowed by the FED. Primary order parameters (POP) are intrinsic to the FER because they serve to define a free energy landscape (FEL). The user must select a set of POP to facilitate an accurate calculation. The greater number of POP selected will increase the accuracy of a calculation, but also will reduce the computational speed.

The optimal selection will strive for the minimum number of order parameters that creates the greatest distinction in physical characteristics.

The user selects d variables, $\{X_1, X_2, \ldots X_d\}$, to be the POP that define the macrostates of a system and to describe its free energy. The free energy will be a function of the POP for fixed thermodynamic condition (TC) and chemical environment (CE). In this invention, the free energy for a given macrostate and template structure, $G(TC, CE|X_1, X_2, \ldots X_d|ts)$ is calculated, where ts is the template structure. In the preferred embodiment, the variables $\{X_1, X_2, \ldots X_d\}$ are discretized over their accessible range. The partition function of the system is given as:

$$Z(TC, CE) = \sum_{ts}\left[\sum_{X_1}\sum_{X_2}\ldots\sum_{X_d}\exp[-\beta G(TC, CE \mid X_1, X_2, \ldots X_d \mid ts)]\right] \qquad \text{Eq. (13)}$$

where $G(TC, CE|X_2, X_2, \ldots X_d|ts)$ consist of solvent, conformation, strain and vibration contributions based on the FED specification. Although not required, a selectable embodiment has the POP independent of template structure. The free energy of the system is given by $G(TC, CE)=-RT \ln[Z(TC, CE)]$. A useful intermediate result is to sum over all POP for a given template structure to obtain:

$$Z(TC, CE \mid ts) = \sum_{X_1}\sum_{X_2}\ldots\sum_{X_d}\exp[-\beta G(TC, CE \mid X_1, X_2, \ldots X_d \mid ts)] \qquad \text{Eq. (14)}$$

where $G(TC, CE|ts)=-RT \ln[Z(TC, CE|ts)]$ gives the free energy for a given template structure. This intermediate free energy will allow the user to find the most stable structure by rank ordering all template structure queries. Since template structures can represent metastable structures, the $G(TC, CE|ts)$ can be used in kinetic models that empirically describe transitions between these stable or metastable structures.

The free energy reconstitution (FER) part of the invention deals with calculation of the FEL given by $G(TC, CE|X_1, X_2, \ldots X_d|ts)$ for fixed IC, CE and template structure, ts. The FEL is difficult to calculate because there are numerous arguments to consider. As an example, for fixed CE, suppose there are 5 template structures, 20 temperatures of interest, and 100 values for each of the POP, for the case d=3. Then the calculation requires 108 FER calculations. For given temperature, CE and template structure, this example indicates that 106 calculations must be performed in the FER part of this invention. As a simpler notation, the POP $\{X_1, X_2, \ldots X_d\}$ will be described more generically as a node. A straightforward method is to calculate G(node) for all nodes exhaustively. However, most G(node) need not be calculated. Only the minimum free energy, $G_{min}$, and the free energy at other nodes for which $G(node) \approx G_{min}$ contribute substantially to the sum in Eq.(14). In the preferred embodiment an adaptive grid approach is used to calculate a small fraction of nodes, and interpolation methods are used to estimate all remaining nodes. Interpolation methods are also applied to variables describing thermodynamic conditions and chemical environments queried by the user. Since other characteristics of the FEL are interesting, such as saddle points that define free energy barriers, the entire FEL is reconstructed using robust adaptive grid and interpolation methods that can be found in the art of computer science.

In the preferred embodiment, dealing with applications involving proteins and complexes of proteins in aqueous solution: The POP are selected to be the number of residues that are in a buried environment, exposed clathrate-solvent environment and exposed mobile-solvent environment, respectively denoted by the variables $\{N_b, N_c, N_m\}$. These order parameters directly relate to the solvent states of a residue, given as sr={b,c,m}. This illustrates how the user-defined FED guides the selection of the POP. Since the FED requires a residue to be in one of these three solvent states, the number of residues within a protein is given by: $N_{res}=N_b+N_c+N_m$. Dividing by Nres the fraction of residues in the buried, clathrate and mobile states, are used to map the free energy landscape in terms of a Gibbs triangle, as FIG. 17 shows.

Figure 17:
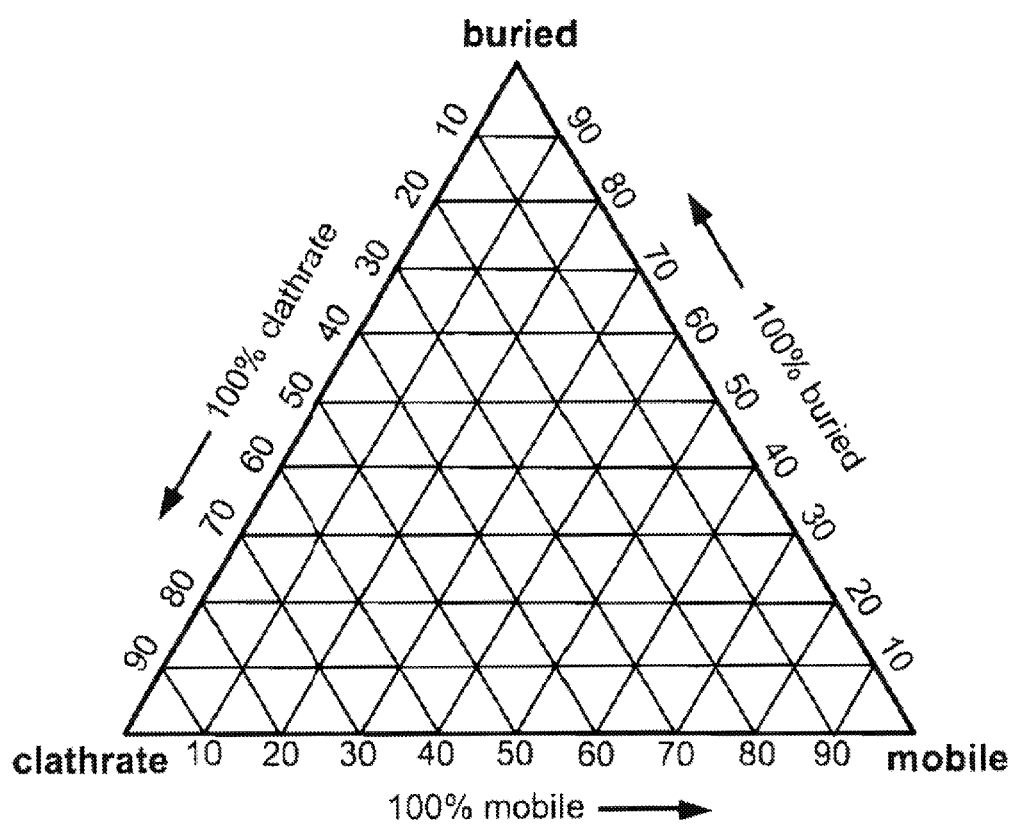
FIG. 17: The layout for the free energy landscape has the form of a Gibbs triangle.

FIG. 17 is the layout for the free energy landscape has the form of a Gibbs triangle. Known in the art of thermodynamics, the Gibbs triangle is commonly employed to describe phase behavior of ternary systems. The percentages of each component always add to 100% when the lines of the Gibbs triangle are read correctly. Consequently, there are two independent variables, such as ($N_b$, $N_m$) to uniquely identify a point on the FEL. Setting the finest resolution to be 1 residue difference normalizes the calculation, meaning all integer values of $N_b$ and $N_m$ are considered. The Gibbs triangle is used for convenience, noting that at each node, G(node) must be calculated using the FER or interpolated. Suppose there are 100 residues in a protein of interest. Then there will be 3100 distinct solvent states possible. The node in the FEL specified by ($N_b$, $N_m$) describes ($N_{res}$!)/($N_b$! $N_c$! $N_m$!) distinct solvent states, all having precisely $N_b$ buried states, Nm exposed mobile-solvent states, and ($N_{res}-N_b-N_m$) exposed clathrate-solvent states. The solvent state will determine what the intramolecular conformation interactions will be.

Free Energy Reconstitution (FER)

Figure 18:
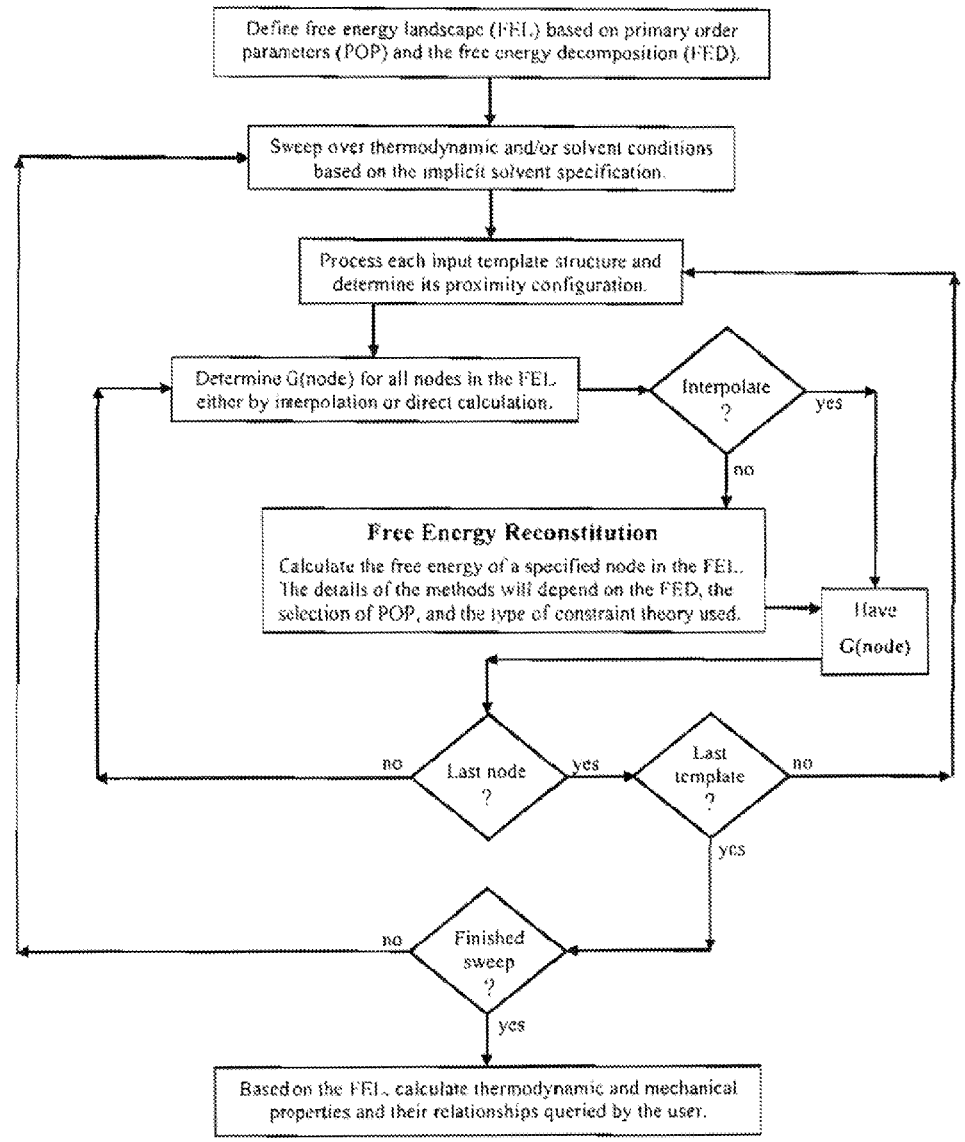
FIG. 18: A process flow chart for the free energy reconstitution according to this invention.
Figure 19:
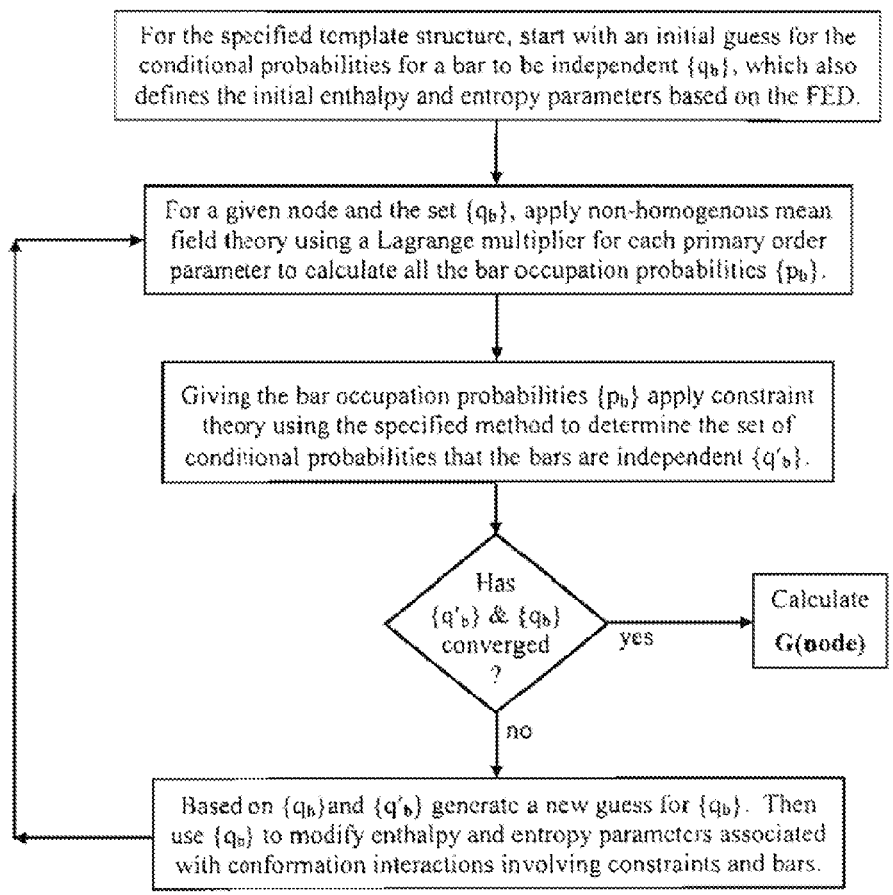
FIG. 19: A process flow chart for calculating the free energy of a node in a molecular structure according to this invention.
Figure 20:
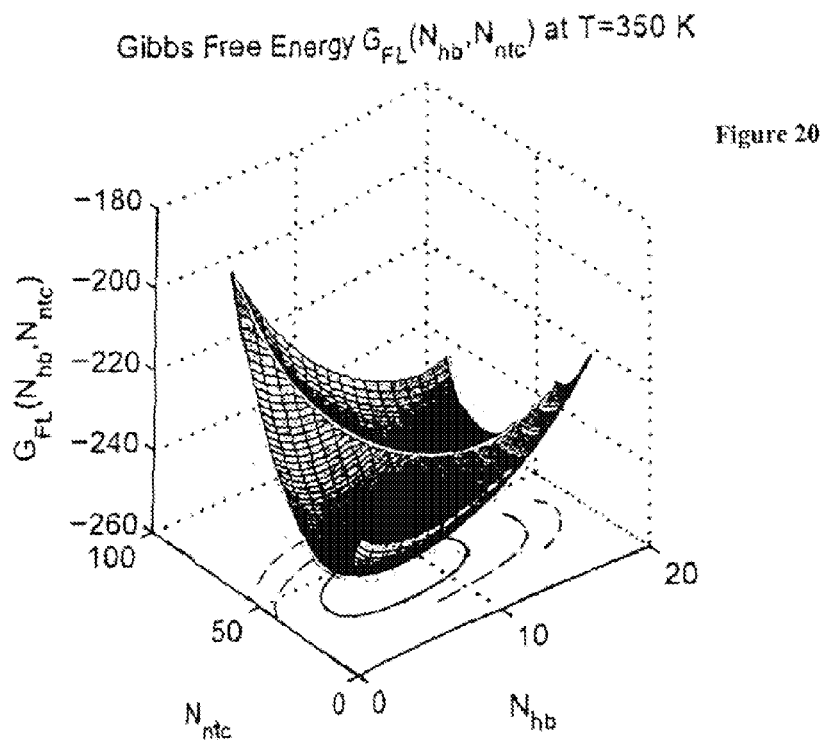
FIG. 20: An example of a plotted free energy landscape at 350 degrees Kelvin according to this invention.
Figure 21:
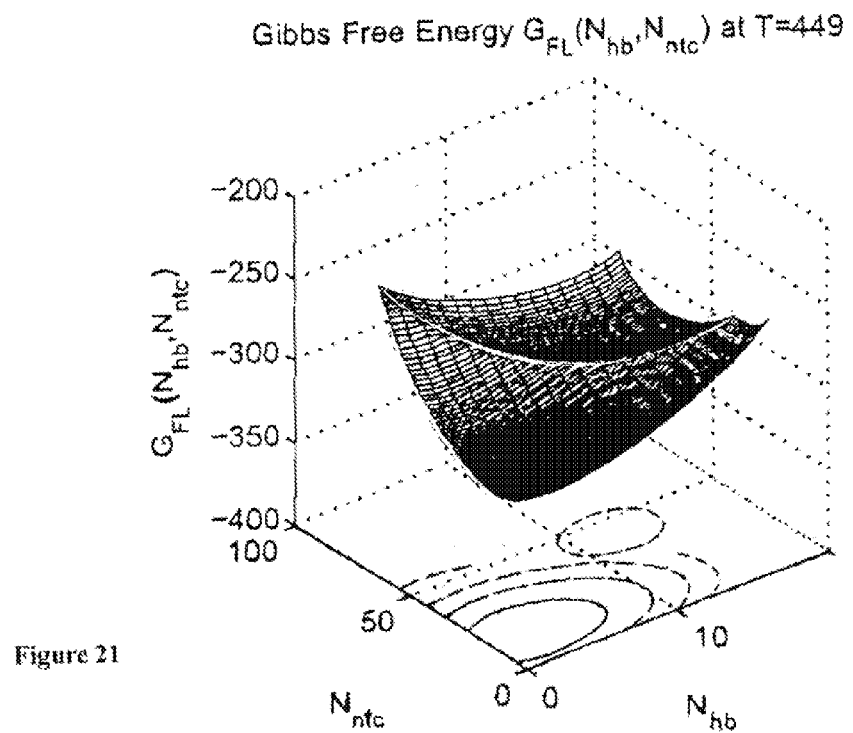
FIG. 21: An example of a plotted free energy landscape at 449 degrees Kelvin according to this invention.

Based on the FED, order parameters, template structures, and thermodynamic and solvent parameters of interest, the FAST calculation consist of performing the free energy reconstitution (FER) to calculate the free energy landscape (FEL). The workflow for the entire FAST process is shown in FIG. 18, and the details of the workflow for the FER process is shown in FIG. 19. An example free energy landscape output from the mDCM is given in FIG. 20 and FIG. 21, showing two different temperatures.

The FER part of the invention consumes most of the CPU demands on the computer. Therefore, the preferred embodiment decouples the constraint topology determination from the solvent state determination. In principle, the non-homogenous mean field theory can be applied to both aspects simultaneously. The mDCM concerned itself with building a constraint topology, while the preferred embodiment concerns itself with building a solvent state. For example, a node in the FEL can be defined by the number of residues that are buried and exposed to mobile-solvent based on the FED and primary order parameters (POP) previously described. Thus, the node represents ($N_b$,$N_m$) in this example FER given here, which is hierarchical in character. The solvent state probabilities are independent of the conformation interactions, and furthermore, the probabilities of the presence of conformation interactions are functions of the solvent state probabilities.

Example of Determining Solvent State Probabilities

Based on the FED, the partition function associated with residue, r, to be in solvent state, s, is given as $Z(s|r)=\exp(\alpha_{slv}(s|r)-\beta h_{slv}(s|r))$. To enforce the global requirement that $N_b$ residues will be buried, a Lagrange multiplier, $\mu_b$, is introduced to calculate the probability that residue, r, is in a buried state. In this example, the Lagrange multiplier couples to nnc(r), which gives the number of nearest neighbor contacts that residue, r, has in a specified template structure. The probability for residue, r, to be buried is given by:

$$p(b|r) = \frac{Z(b|r)\exp(\mu_b nnc(r))}{Z(b|r)\exp(\mu_b nnc(r)) + Z(m|r) + Z(c|r)} \quad \text{Eq. (15)}$$

given that $N_b = \Sigma_r p(b|r)$

These two equations are solved iteratively to determine the $\mu_b$ that gives the desired result that there are on average, $N_b$, number of buried residues. This procedure is standard practice in the art of Statistical Physics. The exact form of this equation needs to be specified by user-defined rules. In the preferred embodiment, the Lagrange multiplier couples to nnc(r) so that the more neighbors a residue has, the more likely it will be buried. The inhomogeneous mean field theory assumes the solvent probabilities, p(s|r), are independent, but not identical. Indeed, p(s|r) depends on the residue type through its enthalpy and entropy parameters, and the proximity configuration of the template structure whereby nnc(r) is determined.

A similar process needs to be performed to obtain $N_m$, describing the number of residues exposed to mobile-solvent. The number $N_m$ has a range from 0 to ($N_{res}-N_b$). If a residue is exposed to solvent, there is nothing that biases the solvent to be mobile or clathrate like, so the Lagrange multiplier, $\mu_m$, will couple to a simple indicator function. The indicator function is 1 when a residue is in a mobile-solvent state, otherwise 0. The probability for residue, r, to be exposed to mobile-solvent is given by:

$$p(m|r) = \frac{Z(m|r)\exp(\mu_m)}{Z(m|r)\exp(\mu_m) + Z(c|r)}(1 - p(b|r)) \quad \text{Eq. (16)}$$

given that $N_b = \Sigma_r p(m|r)$

The formula p(m|r) takes into account that a residue can only be exposed to solvent if it is not buried. The probability that the residue is not buried is explicitly built into the equation, and the multiplicative ratio involving partition functions with the Lagrange multiplier, $\mu_m$, represents the conditional probability that if the residue is not buried it is exposed to mobile-solvent, rather than clathrate-solvent. Knowing p(b|r) in advance, this equation is easily solved iteratively to determine the $\mu_m$ that gives the desired result that there are on average, $N_m$, number of exposed residues to mobile-solvent. Once p(b|r) and p(m|r) are known, it follows that p(c|r)=1−p (b|r)−p(m|r). Although other implementations can be employed to calculate the solvent state probabilities for each residue, the model independent aspect of the calculation is to have these probabilities, and treat them as independent for the remaining calculations in the FER.

Example of Determining Solvent Free Energy of the System

The solvent part of the free energy decomposition, $G_{solv}$, for a system, such as a protein, is calculated based on the solvent state probabilities. Solvent contributions are additive irrespective of the details of the FED. Based on the example FED previously described, the total solvent contribution to the free energy is given as:

$$G_{solv} = \Sigma_r \Sigma_s [h_{slv}(s|r) - TR\alpha_{slv}(s|r)]p(s|r) +$$ intrinsic Eq. (17)

$$TR\Sigma_r \Sigma_s p(s|r)\ln[p(s|r)] +$$

$$\Sigma_{\langle r1,r2 \rangle}[(h_{hph} - TR\alpha_{hph})]p(b|r1)p(b|r2) +$$ hydrophobic $$\Sigma_{\langle r1,r2 \rangle}[(h_{shb} - TR\alpha_{shb})][p(b|r1)p(c|r2) +$$ H-bond type 1
$$p(c|r1)p(b|r2)] +$$

$$\Sigma_{\langle r1,r2 \rangle}[(h_{shb} - TR\alpha_{shb})][p(b|r1)p(m|r2) +$$ H-bond type 2
$$p(m|r1)p(b|r2)](1 - p_{hb})$$

where {r1,r2} means the connection between residue r1 and residue r2 that was predetermined from the proximity configuration of a specified template structure. This is shorthand notation, because {r1,r2} refers to a different set of connections for hydrophobic interactions compared to the hydrogen bond connections. The context of the type of interaction is listed, so this can be implicitly understood. The first three terms in Eq.(17) can be calculated immediately after the probabilities, p(s|r), are calculated. The fourth term has the probability, $(1-p_{hb})$, for a H-bond to form to solvent when the intramolecular H-bond breaks when one residue is buried and the other is exposed to mobile-solvent. The probability, $p_{hb}$, is also based on shorthand notation, since it depends on {r1,r2}, because intramolecular H-bonds are sensitive to their local environments. The probability that an intramolecular H-bond will form, given by, $p_{hb}$, is calculated by the following formula:

$$p_{hb} = \left[\frac{Z'(HB, nat)}{Z'(HB, nat) + \exp(\alpha_{shb} - \beta h_{shb})}\right]$$ native H-bond Eq. (18)
$$p_{nat}(r1)p_{nat}(r2) +$$
$$\left[\frac{Z'(HB, dis)}{Z'(HB, dis) + \exp(\alpha_{shb} - \beta h_{shb})}\right]$$ disordered H-bond
$$[1 - p_{nat}(r1)p_{nat}(r2)]$$

where $\exp(\alpha_{shb}-\beta h_{shb})$ is the partition function for the H-bond that forms to solvent. The remaining variables, Z'(HB,bin), Z'(HB,dis), and $p_{nat}(r)$ require detailed descriptions.

The function Z'(HB,nat) is almost the same function as that given in Eq.(9). However, a few notations have been added to facilitate understanding of the formulas. Since the form of many different types of conformation interactions is similar, the partition function Z(type,form) tells both the type of interaction and the form it is in. In this case, we are interested in the intramolecular H-bond, so the type is HB. The template structure will determine the bin that describes the intramoleclar H-bond within the template structure. Irrespective of the exact details of what bin the native H-bond has, the form of this H-bond is native-like, hence the label, nat. Similarly, Z'(HB,dis) is almost the same function as Eq.(10) in that it describes a disordered intramolecular H-bond. This notation is convenient, but is shorthand, as Z'(HB,nat) depends on the location of the H-bond, and this is implicitly understood. The reason for the prime on these functions is because the parameters for the conformation interactions renormalize based on the result of the constraint theory, dealing with whether bars are independent or redundant.

Referring back to Eq.(9), it is rewritten here using new notation and keeping track of primed variables. The equation for a native H-bond is given by:

$$Z'(HB,nat) = \frac{\exp(\sigma'_1(bin)+\sigma'_2(bin)+\sigma'_3(bin))\exp(-\beta\in')}{Z_o(bin)}$$ Eq.(19)

where bin is determined by the native template structure, and it is left as it was in Eq.(9) to emphasize the similarity with Eq.(19). So the difference is that all the pure entropies have a prime on them, and there is also an added Boltzmann factor, of the form $\exp(-\beta\in')$, which relates to strain energy. The variable, ∈, is defined as a strain variable in the FED. However, in Eq.(19) the variable is ∈', which differs from ∈. In the FER the pure entropies associated with bars are functions of $q_b$, which gives the probability that the bar is independent, given that the bar is present in the network. For the case that all bars of a given interaction are independent, then the prime entropies equal to the bare values, and ∈'=0. For this special case, Eq.(19) is exactly the same as Eq.(9). The details of how these prime variables depend on {$q_b$} must be user-defined. An example of such functions for a preferred embodiment will be described below. In the FER, the form of the equations remains same, but the enthalpy and entropy parameters will renormalize to different values depending on the details of the effective body-bar network.

The last variable to be explained in Eq.(18) is $p_{nat}(r)$. This is an additional variable that has been added in the preferred embodiment of this invention, and the details of it, or having it at all, depends on the rules of the user-defined FER. In the preferred embodiment, a residue can be in a native-like state, which allows only for native fluctuations about the template structure, or in a disordered state, that can deviate far from the template structure such that Z'(type,dis) is used to describe the intramolecular conformation interaction. For conformation interactions in the FED that depend on one residue, say residue, r, the native version is used with probability $p_{nat}(r)$, and the disordered version is used with probability $1-p_{nat}(r)$. In the case of a H-bond spanning between two different residues, say r1 and r2, then the native version of the H-bond is used only when both residues are native-like, which has the probability of $p_{nat}(r1) p_{nat}(r2)$, since these probabilities are treated as independent. If either one of the residues, or both, are disordered, then the disordered form of the interaction is used, where $1-p_{nat}(r1) p_{nat}(r2)$ is the probability for this event to occur. The rule or procedure to calculate $p_{nat}(r)$ is amorphous. In the preferred embodiment, $p_{nat}(r)$ is equal to the arithmetic mean of the probability to be buried over all its neighbors, for which there are nnc(r) of them. This rules implies the more buried a template structure is, the higher probability it has to be native-like, and as it becomes more exposed to solvent, it also becomes more disordered. However, a residue looks native-like or disordered based on its neighbors driving it.

The interpretation of Eq.(18) can now be completely explained. The first term says that if residues r1 and r2 happen to both be native-like, then if there is a chance for the intramolecular H-bond to break, the probability is determined by the appropriate ratio of partition functions of breaking and not breaking as a two state process. However, this calculation will only be used when one of the residues is buried while the other is exposed to mobile-solvent. As can be appreciated, the FER is built upon a series of conditional probabilities that if certain conditions are met, the probabilities are easy to calculate, and stringing them together gives the final probabilities that a conformation interaction is present or not. This probability depends strongly on the solvent state. The solvent state controls the characteristics of the constraint topology. Some terms, directly couple solvent probabilities with probabilities related to conformation interactions determined by the body-bar network.

Example of Determining Conformation Interaction Probabilities

The description of the intramoleclar H-bond is typical of all conformation interactions that can be in native-like states or disordered states. Other interactions, such as clathrate contacts, ionic bonds or covalent bonds are present when certain conditions are met, or always present because they are quenched and not allowed to fluctuate. All these cases are summarized in Table 1, for the example FED previously described as a preferred embodiment of this invention. Whether entropies are additive or not is answered in the second column. The probability for an interaction to be present is given in the third column. The last column indicates whether the interaction is coupled. In some sense, all the conformation interactions, except for covalent bonds, are coupled to the solvent probabilities. However, no coupling means that once the solvent condition is met the conformation interaction is present. Only a H-bond has the situation that there is a choice for an intramolecular H-bond to form, or a solute-solvent H-bond to form. This is an additional fluctuation that is possible for a given solvent state. In this case, the solvent enthalpy and entropy parameters and the conformation enthalpy and entropy parameters compete head to head, and thus coupled. For shorthand notation, in Table 1, $p_{hb-nat}$ refers to the first conditional term in Eq. (18) which determines the probability for the intramolecular native-like H-bond to form over the solute-solvent H-bond. Similarly, $p_{hb-dis}$ refers to the same thing, except the intramolecular H-bond is disordered, given by the second conditional term in Eq.(18).

TABLE 1

| Interaction name (type) | Additive ? | Probability of being present | Coupled ? |
|---|---|---|---|
| Solvation: (buried = b) | Yes | p(b\|r) | No |
| Solvation: (mobile-solvent = m) | Yes | p(m\|r) | No |
| Solvation: (clathrate-solvent = c) | Yes | p(c\|r) | No |
| Hydrophobic interaction (hph) | Yes | p(b\|r1) p(b\|r2) | No |
| Solute-solvent H-bond (shb) | Yes | p(b\|r1) p(c\|r2) + p(c\|r1) p(b\|r2) + p(b\|r1) p(m\|r2) + p(m\|r1) p(b\|r2)] (1 − phb) | Yes |
| Intra-residue (passive = p) | No | p(c\|r) | No |
| Intra-residue (hierarchical = hl-nat) | No | [1 − p(c\|r)] pnat(r) | No |
| Intra-residue (hierarchical = hl-dis) | No | [1 − p(c\|r)] [1 − pnat(r)] | No |
| Inter-residue (packing = pck-nat) | No | p(b\|r1) p(b\|r2) pnat(r1) pnat(r2) | No |
| Inter-residue (packing = pck-dis) | No | p(b\|r1) p(b\|r2) [1 − pnat(r1) pnat(r2)] | No |
| Intramolecular H-bond (HB-nat) | Yes | p(b\|r1) p(b\|r2) pnat(r1) pnat(r2) + p(b\|r1) p(m\|r2) + p(m\|r1) p(b\|r2)] phb-nat | Yes |
| Intramolecular H-bond (HB-dis) | Yes | p(b\|r1) p(b\|r2) [1 − pnat(r1) pnat(r2)] + p(b\|r1) p(m\|r2) + p(m\|r1) p(b\|r2)] phb-dis | Yes |
| Covalent bond (CB) | Yes | 1 whenever template structure requires it | No |
| Ionic bond (IB) | Yes | p(b\|r1) p(b\|r2) | No |

More sophisticated FED can be considered, and this invention is designed to handle these variants. As an example, as pH changes, the protonation state of residues change based on their pKa values. The probability for a proton to be present can be directly incorporated into the probability for various H-bonds to form or not form. The user can specify the pKa values that are needed by making estimates with existing methods. However, the pKa values change depending on the degree that a protein is folded, or partially unfolded. These local geometrical dependences can be incorporated into the FED using local rules, which are already implemented in the art of Computational Biology. Since these rules are always empirically based, and there are many rules available, the user is free to use them, modify them, or make new ones. If this is done, the pKa values will be predicted by this invention. The important point is that the FER strings conditional probabilities together, and in this case, create more types of H-bonds that are possible, but nothing fundamental changes in the methodology. As such, this invention provides a general DCM solver, leaving the FED and the FER rules open to the user.

Example of Determining Conditional Bar Probabilities

As indicated in Table 1, for each conformation interaction defined in the FED, there is a probability for it to be present in the body-bar network. Given that the interaction is present, the conditional probability for the b-th bar, in the c-th constraint, of the i-th interaction is given by:

$$p(i, c, b) = \frac{w(i, c, b)\exp(\Sigma_j w(i, c, j)\sigma'(i, c, j))}{Z'(\text{type, form})} \exp(-\beta\varepsilon'(\text{type, bin}))Z_o(\text{bin}) \quad \text{Eq. (20)}$$

where all terms in the expression have been defined previously. The expression in Eq.(20) is general, and works for interactions having distributed constraints, and for localized interactions. First the meaning of it for distributed constraints. Implicit to Eq.(20) is the location of the fractional bar, which will determine what w(i,c,b) will be. There in fact is multiple number of p(i,c,b) for each location of a fractional bar. However, schematically Eq.(20) works for all such distributed bars with the location information surpassed. The extra factors required for distributed constraints complicate things. Localized interactions will generally look simpler because w(i,c,b)=1 for only one bar, and zero for all others. Also, the $Z_o$(bin) term usually is a single Boltzman factor. Thus, there is no fundamental difference between a distributed constraint and a localized one, although the most common form of the localized one is given by:

$$p(i, c, b) = \frac{\exp[\sigma'(i, c, b) - \beta(E(i, c, b) + \varepsilon'(\text{type, bin}))]}{Z'(\text{type, form})} \quad \text{Eq. (21)}$$

where all the exponential terms have been combined, but otherwise Eq.(21) is identical to Eq.(20) in the special case that the constraint is localized, rather than distributed. Notice how E(i,c,b) is related to $Z_o$(bin). For the case that $Z_o$(bin)=exp(−β(E(i,c,b)) it follows that E(i,c,b)=−RT ln[$Z_o$(bin)]. In the formula to obtain the total conformation free energy contribution of the system, the quantity E(i,c,b) will be used to keep the notation simple. However, for an interaction that happens to be have a distributed constraint, then the E(i,c,b) in the formula will represent−RT ln[$Z_o$(bin)]. This is an example, showing that bars can contribute to an additive type of entropy, because in the distributed constraint case, there is intrinsic mixing entropy which is additive.

It only occurs because of massive degeneracy, but this gives the user considerable flexibility in modeling.

Example of Determining Bar Probabilities for a Body-Bar Network

The probability needed to weight the bars in the body-bar network is the probability for a bar to be present, which requires the interaction to be present. Let P(location, type, form) denote the probability that the interaction is indeed present, which is given by Table 1 for some example interaction types. To simply the notation, call the probability of a bar to be present as $p_k$, where the label k is considered unique over the entire body-bar network. In other words, $p_k$=p(i,c,b) P(location, type, form) in schematic notation. The $p_k$ represents a bar capacity for the k-th bar in the effective body-bar network. The collection of all such bars in the body-bar network is denoted as $\{p_k\}$. At the risk of some confusion, normally, at this point a bar is a bar is a bar. So, the notation $\{p_b\}$ is used for bar occupation probabilities in the body-bar network in the appropriate context.

Constraint Theory Using Maxwell Constraint Counting (MCC)

After the $\{p_b\}$ are determined for all bars in the network, the user can define the type of constraint theory to use to determine the corresponding $q_b$, being the conditional probability that the b-th bar is independent when it is present. At this point, only two attributes to the bars are required. The first is a bar entropy, which is now denoted in a generic way as $\gamma_b$, but it is just a bare entropy, given by an original $\sigma$ defined by the FED. Also note that passive bars are assigned no numbers, but always assumed to have the lowest entropies. The second attribute is the bar's capacity, given by $p_b$. In MCC, all bars are placed with lower entropy are placed before bars with higher entropy. Each bar is assumed to be independent until globally, there are enough constraints to equal the number of DOF. Then, sum a sort ordered list of bar occupation probabilities $[\Sigma_b\ p_b]_{ordered}$ until it equals $6(N_V-N_g)+3N_a$, where $N_V$ is the number of vertices in the network that represent rigid bodies each with 6 DOF, $N_g$ is the number of connected graphs, normally equal to 1, and $N_a$ is the number of isolated atoms, usually equal to 0. In general, this equality cannot be met. Define $b_{max}$ such that summing from b=1 to $b_{max}$ makes $[\Sigma_b\ p_b]_{ordered} > 6(N_V-N_g)+3N_a$. Then for all $b < b_{max}$ it is the case that $q_b$=1. For all $b > b_{max}$ it is the case that $q_b$=0. Then, to get the equality to work, adjust the $q_b$ for b=$b_{max}$ while making sure all bars having the same entropy value at the $b_{max}$ level are treated equally. This is an algebraic exercise, and this special q is assigned to all bars in the network that have the same entropy as the $b_{max}$-th bar. This special q is called $q_{maxwell}$. Then, at the end, it follows that $[\Sigma_b\ q_b\ p_b]_{ordered}$=6$(N_V-N_g)+3N_a$ precisely, such that below the Maxwell level, all $q_b$=1, at the Maxwell level all bars (with same entropy) have $q_b$=$q_{maxwell}$, and all bars above the Maxwell level have $q_b$=0.

Constraint Theory Using the Virtual Pebble Game (VPG)

A more elaborate algorithm called a virtual pebble game takes into account the location of where the bars are in the body-bar network, and as such, will identify rigid regions within the body-bar network as it is built up one bar at a time. This procedure is complicated, and the pseudo code for it is given in the appendix. In general, the results will have the following characteristics. Most $q_b$ will either be 1 or 0. The only $q_b$ that will not be 0 or 1, are those that correspond to bars that have degenerate entropy (which means often there will only be one bar) that form a Laman subgraph for the first time. The operational details are fully explained in the pseudo code. The VPG is able to obtain mechanical properties. It is found in practice that MCC can describe the thermodynamic behavior of proteins well, but it is limited in not being able to provide the mechanical aspects that the VPG also provides.

Self-Consistent Constraint Theory (Using MCC or VPG)

In the initial step, of the FER an initial guess for all $q_b$ must be made ranging from [0,1]. The final results do not depend on this guess, but how fast the result converges does depend on how good the guess is. Neglecting a small speed up of usually less than 30% found in practice, it turns out that an initial guess that all bars are independent is good. Based on $q_b$=1 for all b, the initial strain energy is zero because it only appears when redundant constraints appear. Bare entropy parameters are used in all the equations to determine the bar probabilities. Then the $\{p_b\}$ are calculated, and a new set of $\{q'_b\}$ is found as output of the constraint algorithm employed (such as MCC or VPG). The same formulas and procedure will be done again, but now using the next set of $\{q_b\}$ to try. The new set could be equal to the set just found $\{q'_b\}$. However, this often leads to non-converged solutions due to oscillations. This is a common problem in the art of Computer Science, Computational chemistry and Computational Physics that is solved by a host of robust methods. One such method, which is not the fastest but works, is to say the next set of variables to be guessed is a linear combination of the old variables guessed and the new predicted variables. This means that $q_{next}$=(x $q_{old}$+(1-x) $q_{pred}$) where x can start close to 0 in the initial iteration toward convergence, but should approach 1 as the solution gets close to convergence. The variable x can actually depend on the bar. In order to get a new set of predicted $\{q'_b\}$ a renormalization of parameters has to be done.

Renormalized Parameters

The simplest model to renormalize entropies is to assume $\sigma(i,c,b)$=q(i,c,b) $\sigma_o(i,c,b)$, where $\sigma_o(i,c,b)$ is the bare entropy value specified in the FED. This seems to work well, but more elaborate functions have been tested that have better mathematical characteristics. There is no unique functional form, except the general principle that the function should be a smooth function of $q_b$, and for $q_b$=1, the renormalized value must equal to the bare value. It is not necessary for the renormalized value to go to zero when $q_b$=0, although there should be some physical justification for a non-zero limiting value. This freedom is part of a user-defined FER.

The enthalpies defined in the FED do not renormalize like entropies do. To account for strain energy, this is accomplished explicitly by adding in a strain energy function $\in'(i)$ where the notation is shorthand from before. All enthalpies of all bars, and all constraints shift by the same amount of strain energy, given by $\in'(i)$ which only depends on the interaction type, and form. In the FED, the parameter $\in(i)$ is defined, using the same shorthand notation. The $\in(i)$ parameter can be a single energy value, or even a function of temperature. It serves the purpose to scale the typical strain energy one would expect the i-th interaction type to be able to tolerate before breaking. In any case, only when the interaction is fully redundant would this value of maximum strain energy be approached. When all bars of an interaction are independent, there should be no strain energy. Since strain energy will be spread out as uniformly as it can be due to relaxation a good model is to assume that $\in'(i)$=$\in(i)$ (1-f(i)) where f(i) is the average $q_b$ for all bars within the i-th interaction. In other words, f(i) is just the fraction of how much the i-th interaction in its entirety is independent. Again, the user is able to define rules in the FER to model the physical processes in a different way than the example given here.

Example of Determining Conformation Free Energy of a System

Once all the bar occupation probabilities and the conditional probabilities that they are independent is known, the conformation free energy of the system, such as a protein, is given by:

$$G_{conf} = \qquad \text{Eq. (22)}$$
$$\Sigma_i p_i [\varepsilon'(i) + \Sigma_c \Sigma_b [E(i, c, b) - RT\sigma'(i, c, b) + RT\ln[p(i, c, b)]]$$
$$p(i, c, b)] + RT\Sigma_i C(i)[\ln(p_i) p_i + \ln(1 - p_i)(1 - p_i)]$$

where $p_i$ is the probability that the i-th conformation interaction is present in the network, and $C(i)=0$ for all interactions that are not coupled as indicated in Table 1, and $C(i)=1$ for all interactions that are coupled. The last term is the mixing entropy for a conformation interaction to be present. This entropy should not be counted if the constraint is always present once the solvent condition is right, because the mixing entropy of the solvent variables accounts for the fluctuations of the interaction being present or not. On the other hand, when an interaction may or may not be present, when the solvent conditions allows it to be present, then there is additional mixing entropy. The notation of Eq.(22) isn't not explicit, meaning that the different types of H-bonds (those that fluctuate and those that do not) have to be treated as separate cases. Other than a few nuisance cases, the formula given in Eq.(22) is general. All other variables used in Eq.(22) have been previously defined, noting that p(i,c,b) is a conditional probability that a bar is present, given that the i-the interaction is present. For localized constraints with only one bar, p(i,c,b)=1, and no contribution appears. However, for distributed constraints even with only one bar, the spatial distribution creates entropy. This feature may not be desirable, as discussed next.

According to Eq.(22), it appears that irrespective of the type of conformation interaction, mixing entropies of bars are counted. Technically, this is true only if there is more than one bar per constraint, since p(i,c,b)=1. However, if fractional bars are considered, accounting for the spatial weight function, then this probability will split up. Using the fractional bars may be an over estimate of the entropy, since the bars are not always free to fluctuate independently from one another. The overestimate is a consequence of applying mean field theory to correlated events. Therefore, the user may wish to not count some of the mixing entropies generated by correlated fractional bars within a distributed constraint. In the preferred embodiment these contributions are included, which may account for the missing entropy that normally results in coarse-graining and elimination of internal DOF. In applications, this balance needs to be tuned.

The FED and FER is an empirical approach to account for many different physical mechanisms in an efficient way. The main purpose of this invention is to provide the means to solve a general form of the DCM, and provide the user the freedom to explore optimal models. The examples presented here, however, are already well justified as empirical models.

Vibration Free Energy Contributions

The formula given in Eq.(12) explains how to add in the free energy contributions due to vibrations in the body-bar network that are not represented in the conformational part of the FED. However, it was not explained how to calculate $\omega'_b$. In the same way that entropy and strain energy parameters renormalize, so it is the case with the frequency of oscillations. Once the renormalization step is completed, the vibration free energy contribution simply adds. This renormalization equation, like the others, is up to the user to determine. In the preferred embodiment, all renormalization equations are linear functions of $q_b$. This linearity assumption is also made here, such that $\omega'_b = (1-q_b) \omega'_{b,min} + q_b \omega_b N^{-1/6}$ where all variables have been defined, except $\omega'_{b,min}$. The new variable, $\omega'_{b,min}$ is the last frequency used for either an independent or partially independent constraint within an overconstrained region as determined by the VPG. In other words, as different Laman subgraphs are identified, $\omega'_{b,min}$ is calculated and recorded. As the network is built up, all previous $\omega'_{b,min}$ are known, and all $\omega'_{b,min}$ are assigned a unique effective frequency, which is the scaled bare value in the case that $q_b=1$.

The physical significance of this renormalization rule indicates that if a constraint is independent, it contributes to the frequency spectrum as if it is independent, and uncoupled, except for the scaling factor that is uniformly applied to all oscillators in the network. If it is redundant, or partially redundant, this means that the network is already rigidified by other stiffer constraints. In that case, the frequency of this constraint is shifted upward to the lowest vibration frequency of the rigid region it happens to fall into. According to the DCM, as the constraints that are weaker are placed, and more regions begin to rigidify, the vibration modes of these regions soften compared to regions that rigidified earlier. However, weaker constraints within already rigid regions due to strong constraints inherit the vibration properties of the rigid region itself. Since all bars are averaged over, this simply gives a self-averaging estimate.

The Virtual Pebble Game

Figure 22:
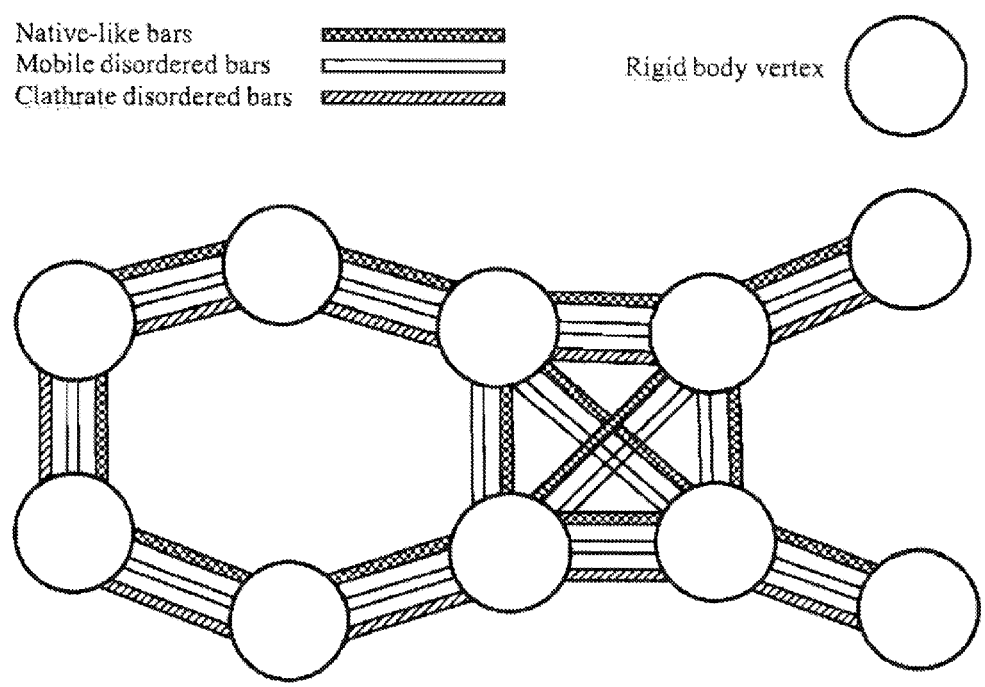
FIG. 22: A schematic of a body-bar constraint network based on a template structure of ten atoms is shown using three interaction types, each modeled by a set of bars.

The virtual pebble game (VPG) builds a constraint network using the set of bars defined by the free energy decomposition (FED) and template structure to determine which bars are independent and redundant. From the output of the VPG, the free energy and other physical properties of a system are calculated. Details of the VPG involving three distinct types of interactions are given as pseudo code following a simple description of the process. The interaction types used are native-like, disordered-clathrate and disordered-mobile; each are modeled as a set of bars placed between vertices, as shown in FIG. 22. All bars with the same incident vertices define an edge irrespective of the type of interaction a bar belongs to. As input to the VPG, each bar has an assigned conformational entropy and probability to be present in the network. As part of the output of the VPG is the conditional probability that a bar is independent given that it is present in the network.

FIG. 22: A schematic of a body-bar constraint network based on a template structure of ten atoms is shown using three interaction types, each modeled by a set of bars. However, the individual bars and their probabilities are not specified nor depicted in the picture.

FIG. 23: An example of how sets of bars constitute different interaction types, and how they get bundled together. The bundle capacity, cb, is simply a sum over bar occupation probabilities, pk, which is the probability that the k-th bar is present in the template structure.

Figure 24:
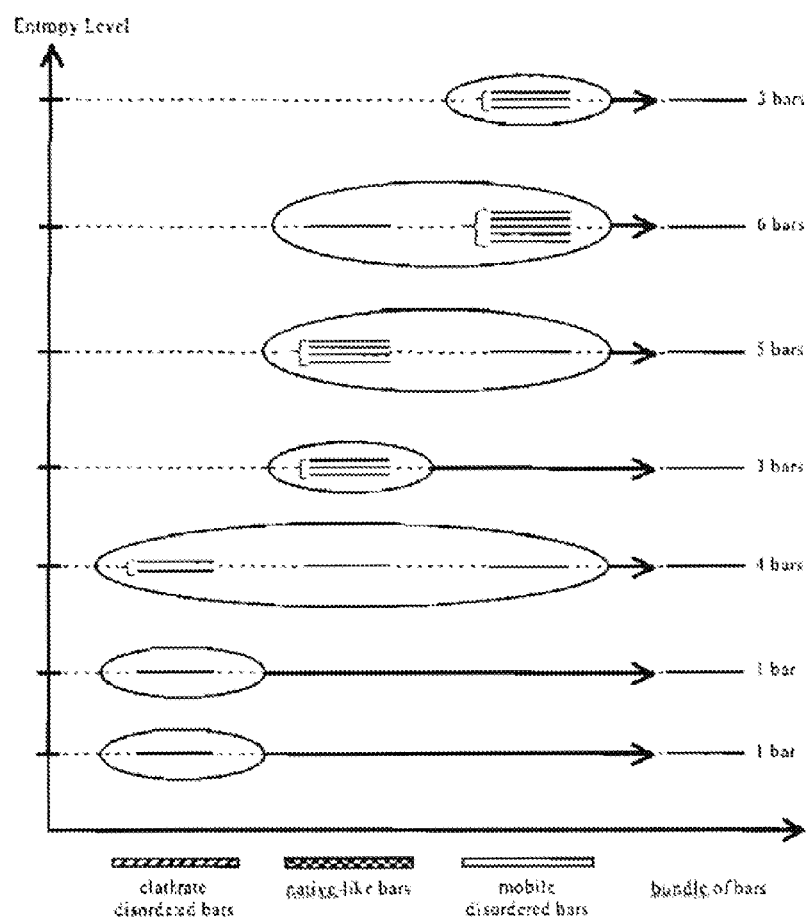
FIG. 24: A schematic illustration showing that all bars sharing the same two incident vertices and entropy level get bundled into a single effective bar with combined bar capacity.
Figure 25:
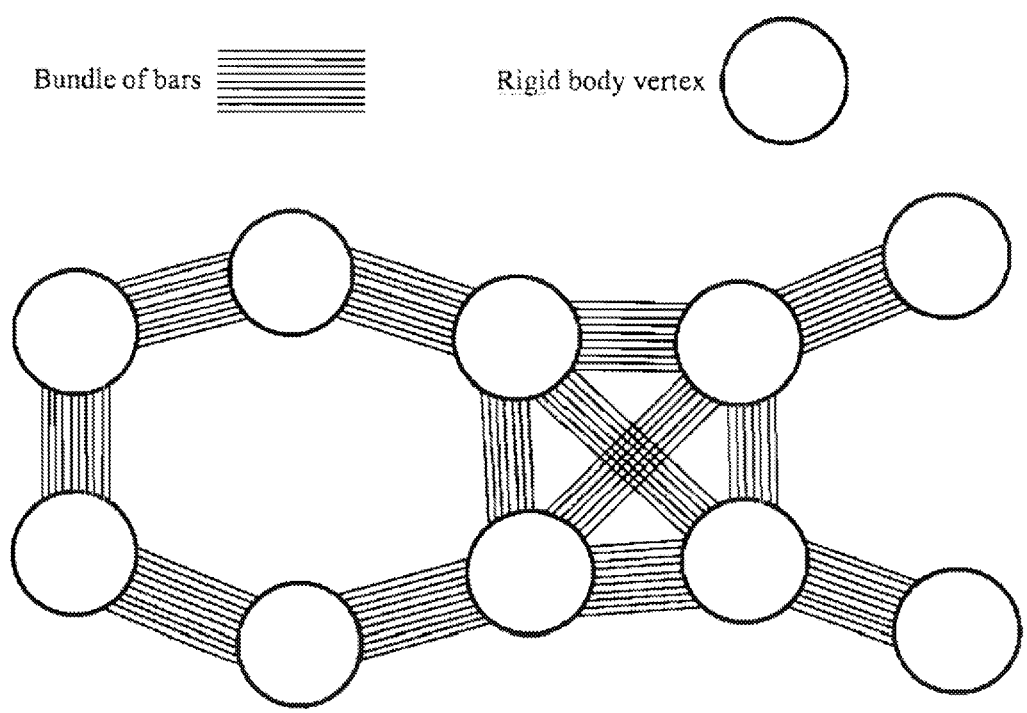
FIG. 25: A schematic illustration showing the body-bar constraint network after the bundling process removes all information about which bar models a specific interaction.

There is a preprocessing step on the bars within the network. First, all bars that are members of a given edge are bundled if they share the same assigned conformational entropy. FIG. 23 shows an example of a set of bars that form a single edge. The bars are separated in three groups based on the types of interactions they model. The various bars have different probabilities of being present in the network. These probabilities are viewed as bar capacities. When a bar is present, it reduces the number of degrees of freedom in the network by one if it is placed in a flexible region. The degrees of freedom within the network are not altered when a bar is not present. These two possibilities are modeled as a capacity, indicating that on average, the number of degrees of freedom that will be removed from a flexible region is equal to the probability of the bar being present in the network. In general, it may happen that multiple bars of a given interaction type have the same entropy assignment, or bars from different interaction types have the same entropy assignment. In either case, all bars that define an edge with the same assigned entropy are bundled together, as FIG. 24 schematically shows. The corresponding details of the bundles are given in FIG. 23. This bundling process is done for each edge in the network to arrive at a large number of bundles of bars placed between vertices, as shown in FIG. 25. The bar and bundle labels are unique throughout the entire network.

FIG. 24: A schematic illustration showing that all bars sharing the same two incident vertices and entropy level get bundled into a single effective bar with combined bar capacity.

FIG. 25: a schematic illustration showing the body-bar constraint network after the bundling process removes all information about which bar models a specific interaction.

Figure 26:
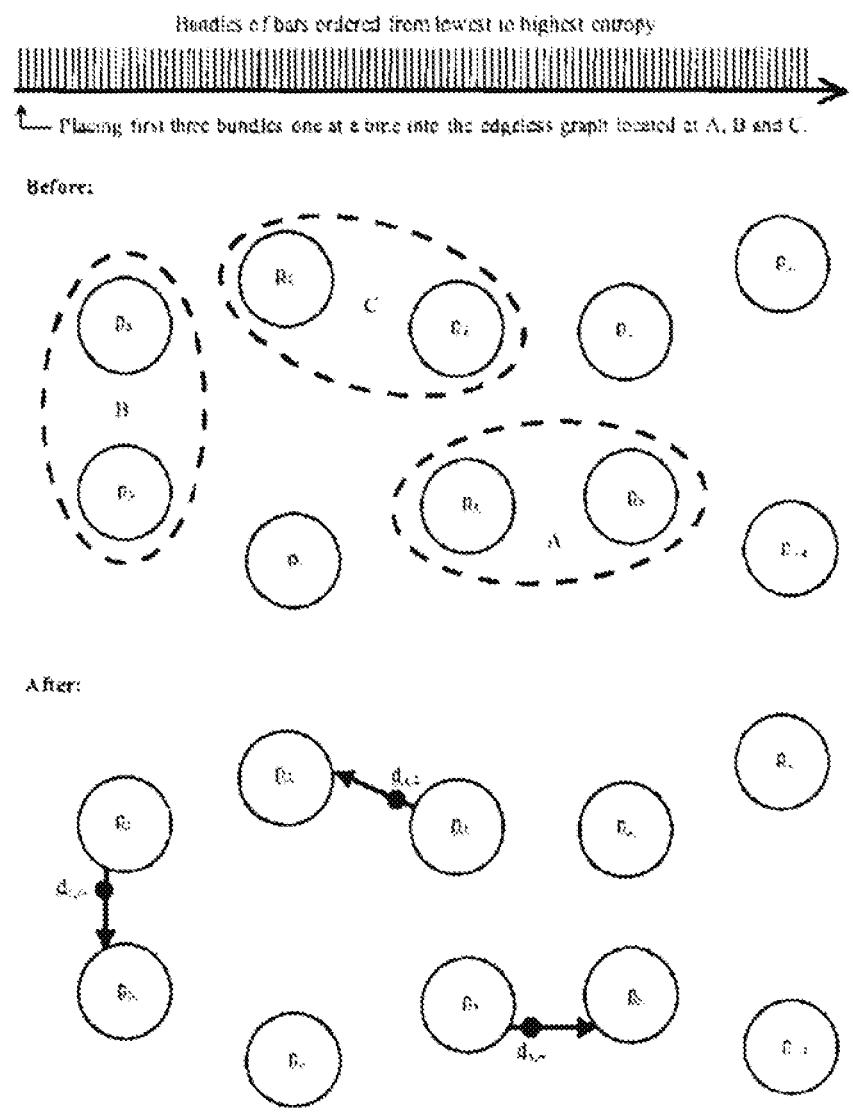
FIG. 26: A schematic illustration showing the process of adding the first three bars into the constraint network one at a time, in the order of events A, B and C.

After the bundling process is completed, the second step in the preprocessing step is to sort the bundles with the lowest assigned conformational entropies. The VPG preferentially places bundles of bars (which may be a single bar) with the lower assigned entropy in the network before other bundles having greater assigned entropy. A stack of bundles of bars is created in a sorted order from lowest to highest entropy. The bundles of bars are placed in the network one at a time. As an example, FIG. 26 shows the procedure of placing the first three bars (events A, B and C) one at a time, starting from the initial structure with no bars. Notice that the location of where the bars are in the network is irrelevant. As bars are added to the network, they remove pebbles from vertices. Pebbles from either incident vertex may be used to cover a bar. The idea is to use as many available pebbles possible to satisfy the maximum capacity of a bar. If the pebble covering is at maximum bar capacity, then the bar is said to be independent. If the pebble covering is anything less than the desired bar capacity, then the bar is said to be redundant, which includes the case that it is partly independent. Once a bar is covered by a certain number of pebbles, it must remain covered for the rest of the game. However, it can be covered differently, using pebbles from either incident vertex. Pebbles can be rearranged within the network as long as the pebble covering over all bars remain constant.

FIG. 26: Top: A schematic illustration showing the process of adding the first three bars into the constraint network one at a time, in the order of events A, B and C. Initially, there will generally be many more available pebbles on incident vertices to cover newly placed bars. Once enough pebbles are retrieved on the two incident vertices, a bar can be covered. Bottom: The pebbles associated with an incident vertex are used to cover the bar, shown as dots. The pebble covering forms a directed graph, where the direction to find alternative pebbles, if needed, is shown by arrows. The number of pebbles covering a bar is denoted by dij, where pebbles from the i-th vertex are being used. The arrows define the direction that can be explored during pebble searches.

Figure 27:
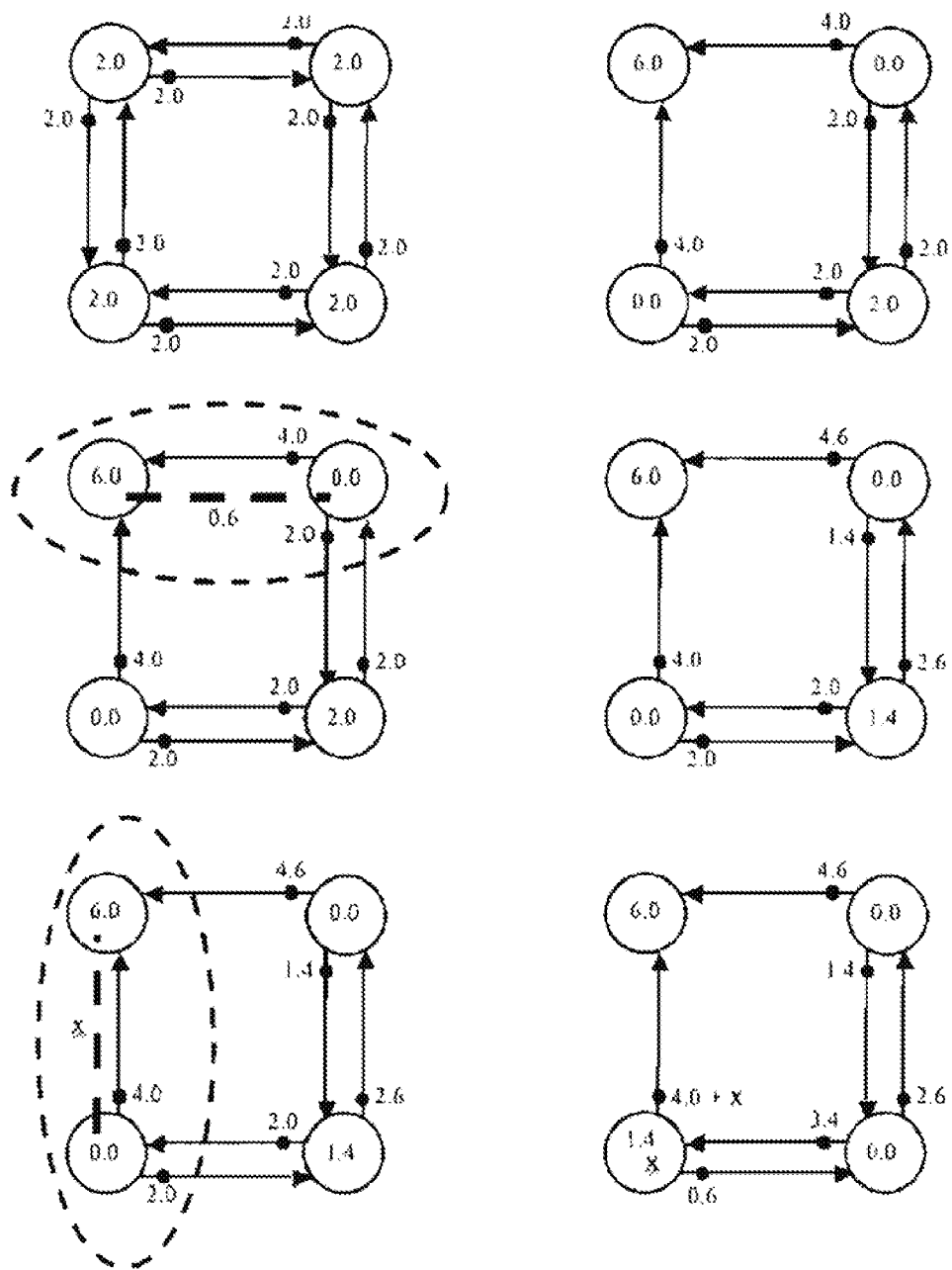
FIG. 27: An illustration showing pebble rearrangements and how bars are covered with pebbles.

FIG. 27: An illustration showing pebble rearrangements and how bars are covered with pebbles. Vertices can gain or lose pebbles during a pebble rearrangement. Top row: A pebble rearrangement always maintains the pebble covering of each bar within the network. Middle row: A bar with 0.6 capacity is placed in the network, and by rearranging pebbles, 6.6 free pebbles are retracted, of which 0.6 are allowed to cover the bar. Bottom row: A bar with capacity x is placed in the network. If $x \leq 1.4$, the bar will be completely covered, and thus independent. If $x>1.4$, the bar is redundant and partially covered with 1.4 pebbles. The probability that the bar is independent is calculated by: $q=(4+1.4)/(4+x)$.

Three examples of how pebbles rearrange within a constraint network is shown in FIG. 27. The top row shows that pebbles can be transferred through the bars as a directed graph, similar to the standard pebble game (SPG). However, in the VPG, the bars are assigned a capacity, and the pebbles are allowed to be fractional. The middle row shows how the pebble covering adjusts in order to cover a new bar that is added to the network. The bottom row is another example of what can happen when a new bar is placed in the network. If the bar capacity is too great for the available free pebbles to completely cover the bar, the bar is then identified to be redundant. Notice from FIG. 27 that as new bars are added to the network, all that matters is to keep track of the net flow of pebbles through the bars in either direction.

Figure 28:
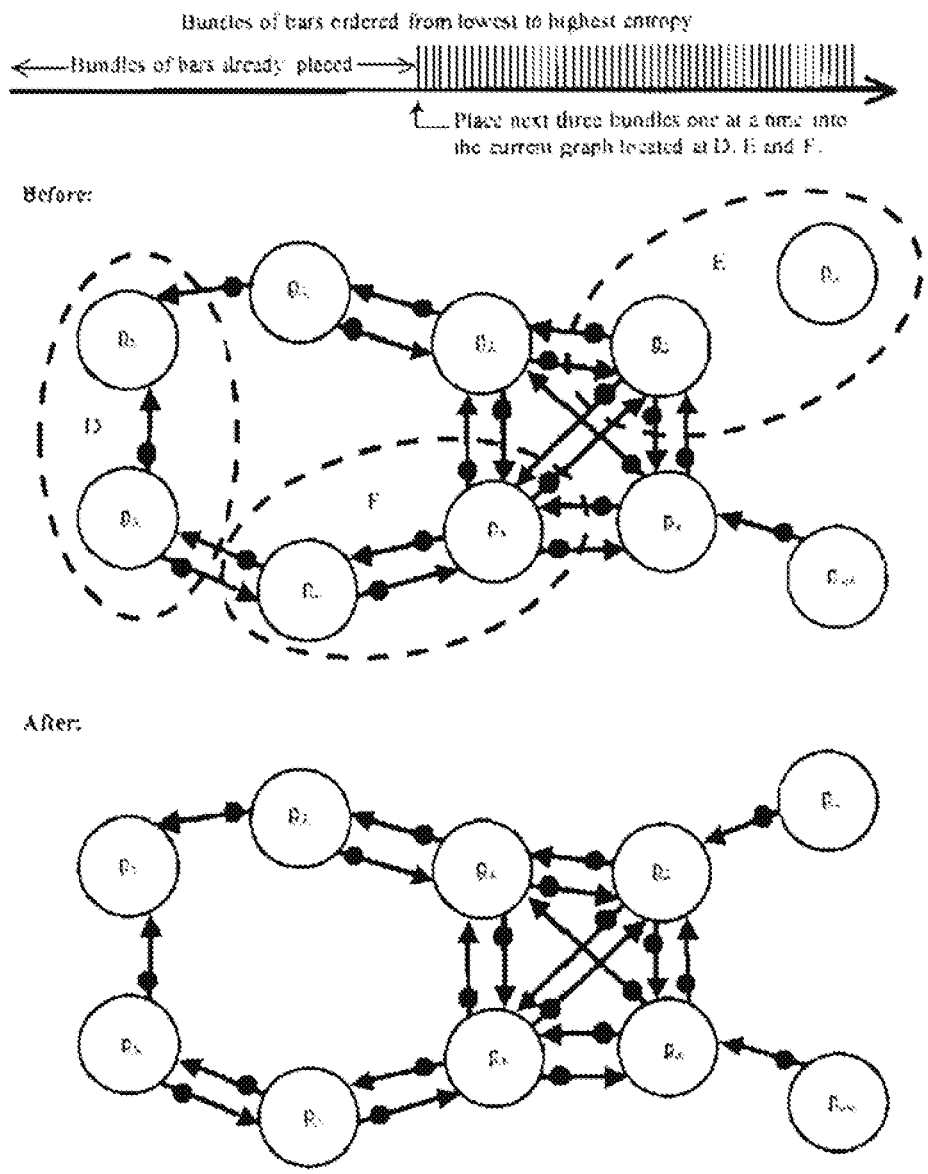
FIG. 28: An illustration showing the process of adding three bars into the constraint network one at a time, in the order of events D, E and F.

FIG. 28: An illustration showing the process of adding three bars into the constraint network one at a time, in the order of events D, E and F. For each event, free pebbles must be retrieved using the rules of pebble rearrangement on the two incident vertices so that the bar can be covered. In this example, all bars are found to be independent. Notice that bars are placed in the network based on the sorted stack, not their location in the network.

The process of adding new bundles of bars or single bars continues until all of them contained in the network are placed. Somewhere latter in the process three more bars are placed one at a time, as labeled by D, E and F events in FIG. 28. As new bars are placed, sometimes a new edge is created, meaning that pebble flow in a given direction opens up for the first time, while in other cases, only the capacity of pebble flow in a given direction increases, due to the enhancement from the new bar.

Figure 29:
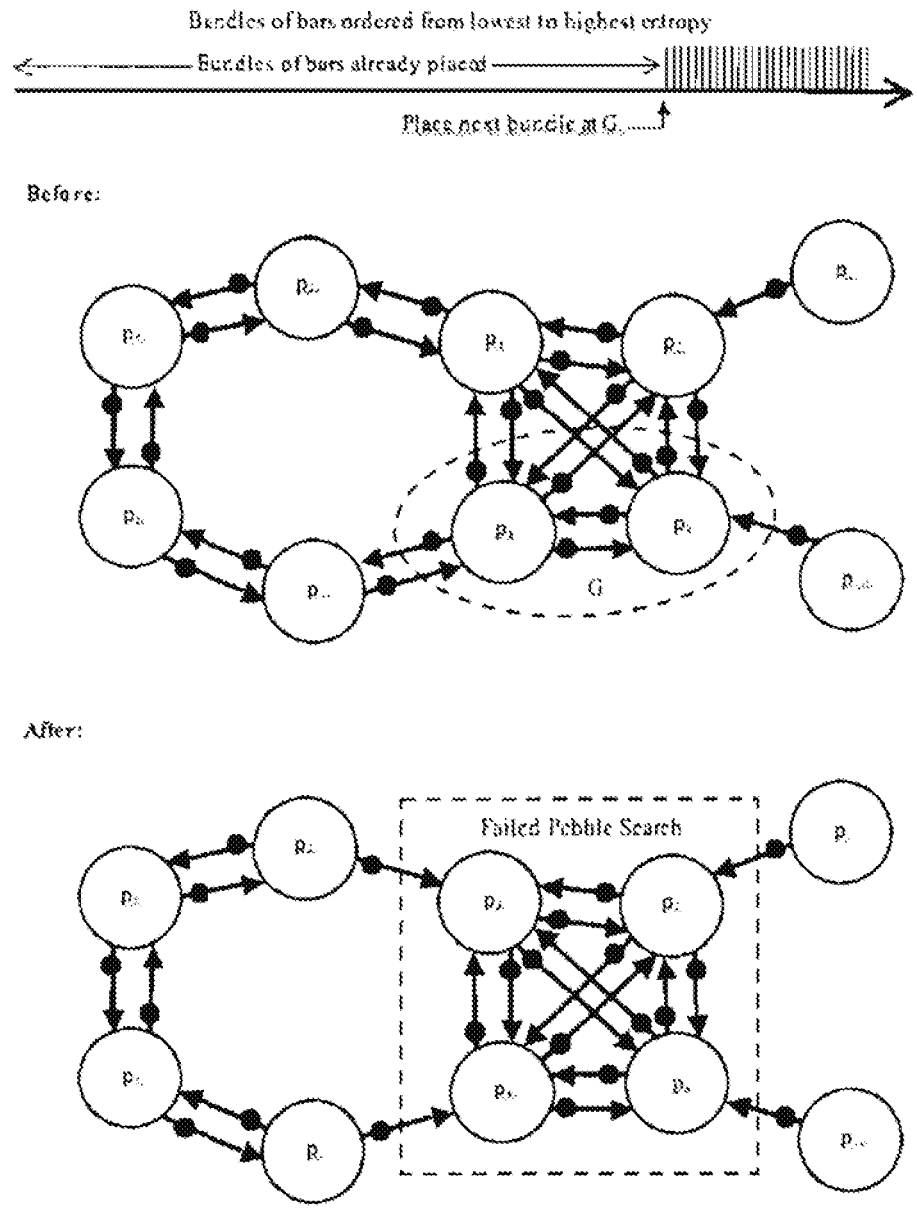
FIG. 29: An illustration showing a failed pebble search that occurs when adding a bar in a region of the constraint network where there are not enough free pebbles to fully cover it.

FIG. 29: An illustration showing a failed pebble search that occurs when adding a bar in a region of the constraint network where there are not enough free pebbles to fully cover it. The failed pebble search shows that the direction of pebble flow prevents the pebble search from expanding further outward. The pebble flow surrounding the failed pebble search is inward toward all its vertices, implying these vertices are mutually rigid.

Figure 30:
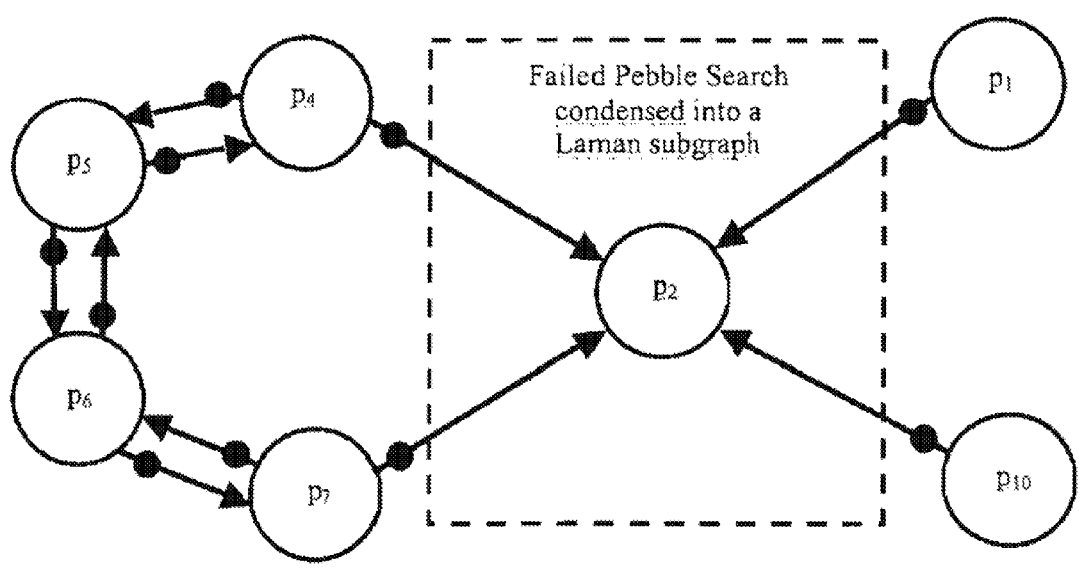
FIG. 30: An illustration of the condensation procedure. After a failed pebble search is identified, the set of vertices and all edges spanning those vertices define a Laman subgraph.

Somewhere much latter in the process of adding bundles of bars, consider event G of placing a bundle of bars in the network shown in FIG. 29. In this case, not enough free pebbles are found to completely cover the bundle, which leads to a failed pebble search. The region of the failed pebble search failed defines a Laman subgraph. The Laman subgraph is self-contained in the sense that no pebble flow is outward. To understand why this must be the case, note that if pebble flow did point outward, then the subgraph would expand to include these nodes. As a result, all bar coverings are pointing inwards to a Laman subgraph when it is identified as a failed pebble search, as can be seen in FIG. 29. This condition is an indication that the set of vertices making up the Laman subgraph, and all edges incident between those vertices, forms a rigid body, and can be represented as a single vertex using a condensation procedure. A condensation procedure is immediately performed following a failed pebble search, such as that caused by event G. Condensation of the failed pebble search into a single vertex is shown in FIG. 30. The failed pebble search defines a Laman subgraph. An edge is assigned to the Laman subgraph only if both of its incident vertices are part of the failed pebble search.

FIG. 30: An illustration of the condensation procedure. After a failed pebble search is identified, the set of vertices and all edges spanning those vertices define a Laman subgraph. These vertices are mutually rigid and are represented as a single vertex, where pebble flow from all bordering vertices point inward to this single vertex.

Figure 31:
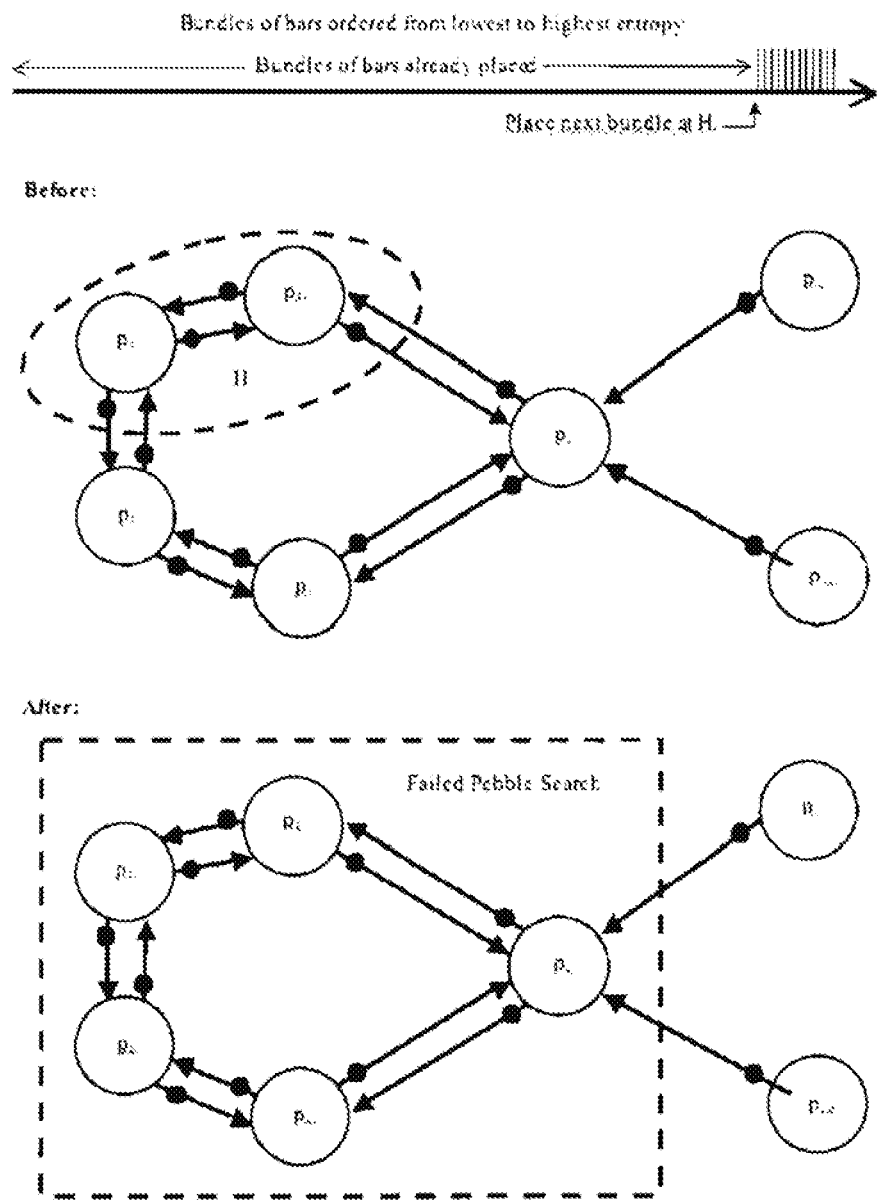
FIG. 31: An illustration of a failed pebble search that includes the sole representative vertex of a previously identified Laman subgraph, and thus both Laman subgraphs merge.

The process of placing bars continues. It will generally happen that as more bars are placed in the network, other Laman subgraphs will be uncovered, as shown in FIG. 31. When this happens, the new Laman subgraph may be disjoint from all other previously identified Laman subgraphs, or parts of the new Laman subgraph may overlap with other previously identified Laman subgraphs. The former case is nothing different than that discussed for event G, shown in FIGS. 29 and 30. The latter case is easy to handle because the Laman subgraphs are condensed into a single vertex. If only one vertex overlaps between two Laman subgraphs, they are merged together as one Laman subgraph. As FIG. 31 shows, a single vertex of a previously defined Laman subgraph can overlap with a new Laman subgraph. Edges that have both of its incident vertices a member of a failed pebble search are uniquely assigned to the corresponding Laman subgraph. Therefore, as long as edge information is stored before the condensation process is applied, the mapping of Laman subgraphs to the original network is fully maintained. The condensation process continually shrinks the effective size of the network, as many vertices over extended regions condense into a single vertex during the condensation process, as shown in FIG. 32.

FIG. 31: An illustration of a failed pebble search that includes the sole representative vertex of a previously identified Laman subgraph, and thus both Laman subgraphs merge.

Figure 32:
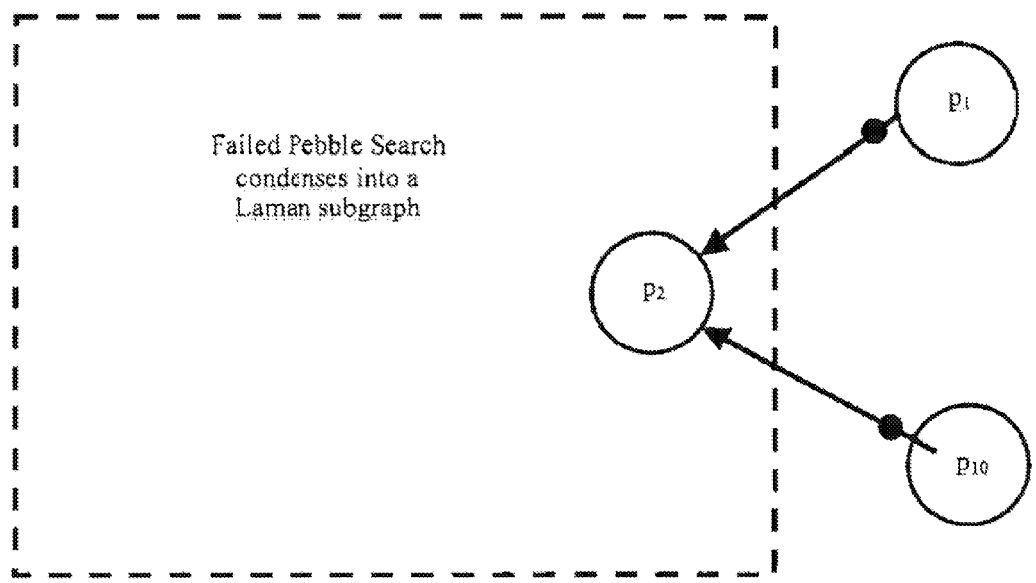
FIG. 32: An illustration of the condensation procedure. After a failed pebble search is identified, the set of vertices and all edges spanning those vertices define a Laman subgraph.

FIG. 32: An illustration of the condensation procedure. After a failed pebble search is identified, the set of vertices and all edges spanning those vertices define a Laman subgraph. In this case, one of the vertices represents a previously defined Laman subgraph, and this condensation merges the two Laman subgraphs into one aggregate. The vertices of the aggregate are mutually rigid and now represented as a single vertex, where pebble flow from all bordering vertices point inward to this single vertex.

The process of placing bars continues until the last bar is placed in the network. After all bars are placed, it must be the case that the network will form a single rigid body. Also, it will usually be the case that the entire network collapses into a single vertex or just a few vertices, due to the condensation process. The reason why over-constrained regions will frequently be uncovered, is because a good FED will over-specify the number of constraints compared to the number of available degrees of freedom in the system.

The claim set implements all of the above-described models and mathematical processes in computerized system. In a first embodiment, the invention includes a method of implementing the Distance Constraint Model to calculate the average network rigidity properties of a molecular structure by reconstructing the network as at least one body-bar multigraph. This computerized method is useful in solving the Distance Constraint Model. Accordingly, one can calculate the free energy landscape (FIGS. 19, 20) of a molecular structure Distance Constraint Model using probability distributions to describe at least one proximity state and at least one body-bar network representing an ensemble of constraint topologies. In one sense, the computerized method uses the Distance Constraint Model to identify rigid clusters, flexible regions, and over-constrained regions in a molecular structure based upon probability distributions.

In the drawings and the specification, typical embodiments of the invention have been disclosed. Specific terms have been used only in a generic and descriptive sense, and not for purposes of limitation. Unless otherwise noted, the inventor is not acting as a lexicographer, and terms herein are intended to have their ordinary meaning. The invention is not restricted to the slavish imitation of each and every detail set forth above. Obviously, devices may be provided which change, eliminate, or add certain specific details without departing from the scope of the invention. The scope of the invention is set forth in the claims below.

REFERENCES

[1] Das, P., Matysiak, S, and Clementi, C. (2005) Balancing energy and entropy: a minimalist model for the characterization of protein folding landscapes. PNAS, 102: 10141-46

[2] Lindorff-Larsen, K., R. B. Best, M. A. DePristo, C. M. Dobson, and M. Vendruscolo, Simultaneous determination of protein structure and dynamics. Nature, 433: 128-32 (2005)

[3] Scheraga, H. A., Khalili, M. and Liwo, A. (2007) Protein-Folding Dynamics: Overview of Molecular Simulation Techniques. Annu. Rev. Phys. Chem., 58, 57-83

[4] Freire, E. (1997) Thermodynamcis of protein folding and molecular recognition, Pure & Appl. Chem., 69, 2253-2261.

[5] Tai, K., Conformational sampling for the impatient. Biophysical Chem. 2004. 107, p. 213-20

[6] Cheluvaraja, S. and Meirovitch, H. (2004) Simulation method for calculating the entropy and free energy of peptides and proteins. PNAS, 101, 9241-46

[7] Munoz, V., What can we learn about protein folding from ising-like models? (2001) Curr. Opin. Struct. Biol, 11, 212-16

[8] Vendruscolo, M. (2002) Energetics of enzyme stability. TRENDS in Biotechnology, 20, 1-2.

[9] Mark, A. E. and van Gunsteren, W. F. (1994) Decomposition of the free energy of a system in terms of specific interactions. Implications for theoretical and experimental studies. J. Mol. Biol., 240, 167-176.

[10] Dill, K. A. (1997) Additivity principles in biochemistry. J. Biol. Chem., 272, 701-704.

[11] Hayward, S. (2001) Computational Biochemistry and Biophysics. (Becker, MacKerell, Roux, & Watanabe, eds), Marcel Dekker, Inc., NY.

[12] Andricioaei, I and Karplus, M. (2001) On the calculation of entropy from covariance matrices of the atomic fluctuations. J. Chem. Phys. 115, 6289-6292

[13] Hilser, V. J. and Freire, E. (1996) Structure-based calculation of the equilibrium folding pathway of proteins. Correlation with hydrogen exchange protection factors. J. Mol. Biol., 262, 756-772.

[14] Kamisetty, H., Xing, E. P and Langmead, C. J. (2008) Free energy estimates of all-atom protein structures using generalized belief propagation. J. Comput. Biol. 15, 755-66

[15] Zhiyong Z. and Wriggers W. (2008) Coarse-Graining Protein Structures With Local Multivariate Features from Molecular Dynamics. J. Phys. Chem. B 112, 14026-14035

[16] Jacobs, D. J., Rader, A. J., Kuhn, L. A. and Thorpe, M. F. (2001) Protein flexibility predictions using graph theory. Proteins: Structure, Function, and Genetics, 44, 150-165

[17] Jacobs, D. J. and Thorpe, M. F. (2000) Computer Implemented System for Identifying Rigid and Flexible Regions in Macromolecules, US patent #6014449.

[18] Wells, S., Menor, S., Hespenheide, B. and Thorpe, M. F. (2005) Constrained Geometric Simulation of Diffusive Motion in Proteins. Physical Biology, 2, S127-S136.

[19] Jacobs, D. J., Dallakyan, S., Wood, G. G. and Heckathorne, A. (2003) Network rigidity at finite temperature: relationships between thermodynamic stability, the nonadditivity of entropy, and cooperativity in molecular systems. Phys. Rev. E., 68, 061109

[20] Jacobs, D. J. and Dallakayan, S. (2005) Elucidating Protein Thermodynamics from the Three Dimensional Structure of the Native State Using Network Rigidity. Biophys. J., 88, 903-15

[21] Lee, A. and Streinu, I. (2005) Pebble Game Algorithms and (k, 1)-Sparse Graphs. EuroComb, DMTCS proc. AE, 181-186

[22] Jacobs, D. J. and Fairchild, M. J. Thermodynamics of a beta-hairpin to coil transition elucidated by Constraint Theory, Biopolymer Research Trends Ed: Pablo C. Sanchez. Nova Publishers, NY ISBN: 1-60021-984-5 45-76 (2007).

[23] Mottonen, J. M., Xu M., Jacobs, D. J. and Livesay, D. R. (2008) Unifying mechanical and thermodynamic descriptions across the thioredoxin protein family, Proteins, in press.

[24] Livesay, D. R., Huynh, D. H., Dallakyan, S. and Jacobs, D. J. (2008) Hydrogen bond networks determine emergent mechanical and thermodynamic properties across a protein family, Chemistry Central Journal 2:17 1-20

[25] Vorov, O. K., Livesay, D. R. and Jacobs, D. J. (2008) Conformational entropy of an ideal cross-linking polymer chain. Entropy, 10, 285-308

[26] Jacobs, D. J., Livesay, D. R., J. Hules, J. and Tasayco M. L. (2006) Elucidating quantitative stability-flexibility relationships within thioredoxin and its fragments using a distance constraint model. Journal of Molecular Biology. 358, 882-904

[27] Livesay, D. R. and Jacobs, D. J. (2006) Conserved quantitative stability/flexibility relationships (QSFR) in an orthologous RNase H pair. Proteins 62, 130-43

The invention claimed is:

1. A computerized method of implementing a Distance Constraint Model on a body-bar multigraph representing constraints on a molecular structure, the method comprising:
using a computer to execute the steps Of a topography processor, the steps comprising:
assigning a rank to each bar in the multigraph to facilitate an ordered placement of bars in a constraint topology reconstruction, wherein said rank is based on an entropy value;
grouping all bars that connect each respective pair of vertices and have a same rank into a respective bundle of bars;
assigning a probability (P) that one of said bars within each bundle is present, wherein P is any real number ranging from 0 to 1;
calculating a capacity of a first bundle of bars to remove at least a partial degree of freedom within the multigraph by adding the values of P for each bar in the first bundle; and
identifying average network rigidity properties by reconstructing the body-bar multigraph via the topography processor through recursive addition of bundles of bars to remove degrees of freedom, wherein degrees of freedom may be represented by any real number;
calculating a molecular partition function with the known values for solvent entropy, solvent enthalpy and conformational enthalpy and with a lowest upper bound estimate for molecular conformational entropy, wherein the lowest upper bound estimate for molecular conformational entropy comprises conformational entropy contributions of independent constraints covering the degrees of freedom within the multigraph, as calculated for at least one selected primary order parameter.

2. The computerized method of claim 1, further comprising:
identifying said independent constraints on the degrees of freedom in the molecular structure, wherein the degrees of freedom and the capacity of the independent constraints to cover degrees of freedom in the molecular structure are respectively represented by any real number greater than or equal to zero.

3. The computerized method according to claim 2, comprising the steps of:
selecting a template that represents the atomic configuration of the molecular structure as a group of vertices;
determining the conformational interaction types affecting the mechanical linkage properties within the template;
determining the number of constraints that will model each of the interaction types and the number of bars that will model each constraint affecting the conformational entropy of the molecular structure; and
assigning initial conformational entropy and enthalpy values to each bar.

4. The computerized method according to claim 3, comprising the steps of:
rank ordering the entropy values associated with all bars modeling all conformational interaction types;
bundling the bars having the same conformational entropy value that connect the same two vertices within the template; and
recursively building a body-bar multigraph for the molecular structure by placing bundles of bars between the appropriate vertices in the template, wherein the placement of the bars depends upon the interaction type between vertices, and wherein the bundles of bars are placed in an order such that bundles with the lowest conformational entropy are placed first.

5. The computerized method according to claim 4, comprising the steps of:
assigning six pebbles to each vertex in the body-bar multigraph, wherein the pebbles represent degrees of freedom; and
covering bundles of bars with pebbles to denote the number of degrees of freedom that a bar constrains within the molecular structure.

6. The computerized method according to claim 5, comprising the step of assigning an initial value of any real number between zero and one to variable Q, wherein Q is defined as the ratio of the number of degree(s) of freedom a bundle of bars actually restricts divided by the bundle's maximum pebble capacity.

7. The computerized method according to claim 6, wherein the step of identifying independent constraints comprises playing the virtual pebble game with the following steps:
(i) assigning the initial value to Q, which is the conditional probability of a constraint being an independent constraint;
(ii) calculating the probability P that the restraint is present;
(iii) adding the values of P for each bar in a bundle to determine the bundle capacity
(iv) updating the value of Q depending upon the value of P by iterating through the interaction types in the molecular structure and modifying the pebble coverage according to new capacities for each bundle of bars; and (v) repeating steps (i) to (iv) until P and Q converge to respective constant values within a specified tolerance.

8. The computerized method according to claim 7, wherein the virtual pebble game comprises holding, the maximum number of degrees of freedom on one vertex within an interaction and collecting the maximum available degrees of freedom on the other incident, vertex of the bundle of bars in the interaction to fill the capacity of the bundle of bars to the maximum extent possible.

9. The computerized method according to claim 8, wherein the virtual pebble game iterates through all of the interactions in the template so that each bundle of bars in each interaction type is covered by the number of pebbles associated with the degrees of freedom available to that bar.

10. The computerized method according to claim 9, comprising the step of condensing all merged Laman subgraphs to a single vertex.

11. The computerized method according, to claim 10, wherein:
for Q=0, the bar is a redundant constraint; and
for Q=1, the bar is an independent constraint.

12. The computerized method according to claim 11, comprising the step of calculating the values of P and Q for multiple templates.

13. A computerized method of implementing a Distance Constraint Model on a body-bar multigraph representing constraints on a molecular structure to plot a free energy landscape for the molecular structure in a macrostate having known values for solvent entropy, solvent enthalpy and conformational enthalpy, the method comprising:
using a computer to execute the steps of a topography processor, the steps comprising:
assigning a rank to each bar in the multigraph to facilitate an ordered placement of bars in a constraint topology reconstruction, wherein said rank is based at least in part on an assigned conformational entropy value;
grouping all bars that connect each respective pair of vertices and have a same rank into a respective bundle of bars;
assigning a probability (P) that one of said bars within each bundle is present, wherein P is any real number ranging from 0 to 1;
calculating a capacity of a first bundle of bars to remove at least a partial degree of freedom within the multigraph by adding the values of P for each bar in the first bundle; and
reconstructing the body-bar multigraph via the topography processor through recursive addition of bundles of bars to remove degrees of freedom, wherein degrees of freedom may be represented by any real number;
calculating a molecular partition function with the known values for solvent entropy, solvent enthalpy and conformational enthalpy and with a lowest upper bound estimate for conformational entropy,
wherein the lowest upper bound estimate for conformational entropy comprises conformational entropy contributions of independent constraints within the multigraph that are ranked with respectively lowest conformational entropy value as calculated for at least one primary order parameter, at least one constraint topology, at least one proximity configuration, and at least one template structure.

14. A computerized method according to claim 13, wherein each order parameter is discretized into a respective node.

15. A computerized method of plotting a free energy landscape for a molecular structure in a macrostate having known values for solvent entropy, solvent enthalpy and conformational enthalpy, the method comprising:
using a computer to execute the steps of a topography processor, the steps comprising:
assigning a rank to each bar in the multigraph to facilitate an ordered placement of bars in a constraint topology reconstruction, wherein said rank is based on an assigned conformational entropy value;
grouping all bars that connect each respective pair of vertices and have the same rank into a respective bundle of bars;
assigning a probability (P) that one of said bars within each bundle is present, wherein P is any real number ranging from 0 to 1;
calculating a capacity of a first bundle of bars to remove at least a partial degree of freedom within the multigraph by adding the values of P for each bar in the first bundle; and
reconstructing the body-bar multigraph via the topography processor through recursive addition of bundles of bars to remove degrees of freedom, wherein degrees of freedom may be represented by any real number;
calculating a molecular partition function with the known values for solvent entropy, solvent enthalpy and conformational enthalpy and with a lowest upper bound estimate for conformational entropy, wherein the lowest upper bound estimate for conformational entropy comprises conformational entropy contributions of independent constraints within the multigraph as calculated for at least one node in the molecular structure;
displaying a graph on a computer of the free energy landscape of the molecular structure by plotting the molecular partition function calculation for at least one node in the molecular structure.

16. A computer program according to claim 15, wherein a node value is determined as a discretized approximation of an order parameter value.

17. A computerized method implementing a Distance Constraint Model on a body-bar multigraph representing constraints on a molecular structure, the method comprising:
using a computer to execute the steps of a topography processor, the steps comprising:
assigning a rank to each bar in the multigraph to facilitate an ordered placement of bars in a constraint topology reconstruction, wherein said rank is based on an assigned conformational entropy value;
grouping all bars that connect each respective pair of vertices and have a same rank into a respective bundle of bars;
reconstructing the body-bar multigraph via the topography processor through recursive addition of bundles of bars to remove degrees of freedom,
calculating a molecular partition function with the known values for solvent entropy, solvent enthalpy and conformational enthalpy and with a lowest upper bound estimate for molecular conformational entropy, wherein the lowest upper bound estimate for molecular conformational entropy comprises conformational entropy contributions of independent constraints covering the degrees of freedom within the multigraph, and
wherein said lowest upper bound estimate is calculated by:
assigning a probability (Q) and calculating a component conformational entropy for said each bar, wherein probability (Q) is a probability ranging from 0 to 1 that said each bar is an independent constraint on a degree of freedom within the molecular structure;

calculating, in an iterative loop, respective probabilities ($P_b$) that said bars in each bundle of bars are present, and further in the iterative loop, using one of said respective probabilities ($P_b$) to calculate an updated probability ($Q_b$), and further in the iterative loop, recalculating said component conformational entropy for said updated probability ($Q_b$);

converging said component conformational entropy values for each bar toward a node conformational entropy value for at least one node in the multigraph for the molecular structure;

and identifying a lowest upper bound estimate of molecular conformational entropy for said node.

18. The method of claim 17, further comprising the step of calculating, a molecular partition function for at least one primary order parameter, at least one constraint topology, at least one proximity configuration, and at least one template structure.

19. A computerized method according to claim 17, wherein assigning a rank to each bar in the multigraph comprises ranking said bars according to entropy values.

20. A computerized method according to claim 17, wherein said node is a discrete value for a selected order parameter, and further comprising the step of graphing a free energy landscape of the molecular structure by plotting the free energy versus nodes on respective axes.

* * * * *